United States Patent
Albaugh et al.

(10) Patent No.: US 7,405,305 B2
(45) Date of Patent: Jul. 29, 2008

(54) PYRROLE-2, 5DIONE DERIVATIVES AND THEIR USED AS GSK-3 INHIBITORS

(75) Inventors: Pamela Ann Albaugh, Carlsbad, CA (US); Jochen Ammenn, Hamburg (DE); Timothy Paul Burkholder, Carmel, IN (US); Joshua Ryan Clayton, Cicero, IN (US); Scott Eugene Conner, Indianapolis, IN (US); Brian Eugene Cunningham, Martinsville, IN (US); Thomas Albert Engler, Indianapolis, IN (US); Kelly Wayne Furness, Avon, IN (US); James Robert Henry, Indianapolis, IN (US); Sushant Malhotra, Indianapolis, IN (US); Mark Joseph Tebbe, Indianapolis, IN (US); Guoxin Zhu, Noblesville, IN (US); YiHong Li, Carmel, IN (US); Brian Raymond Berridge, Greenfield, IN (US); Charles Edward Ruegg, Indianapolis, IN (US); John Morris Sullivan, Greenfield, IN (US)

(73) Assignee: Eli Lilly and Company, Indianapolis, IN (US)

( * ) Notice: Subject to any disclaimer, the term of this patent is extended or adjusted under 35 U.S.C. 154(b) by 104 days.

(21) Appl. No.: 10/506,029

(22) PCT Filed: Mar. 5, 2003

(86) PCT No.: PCT/US03/05052

§ 371 (c)(1),
(2), (4) Date: May 19, 2005

(87) PCT Pub. No.: WO03/076398

PCT Pub. Date: Sep. 18, 2003

(65) Prior Publication Data

US 2005/0288321 A1    Dec. 29, 2005

Related U.S. Application Data

(60) Provisional application No. 60/369,433, filed on Apr. 2, 2002, provisional application No. 60/363,375, filed on Mar. 8, 2002.

(51) Int. Cl.
*C07D 209/12* (2006.01)
*C07D 207/24* (2006.01)
*C07D 211/06* (2006.01)

(52) U.S. Cl. .......... 548/469; 548/547; 546/184
(58) Field of Classification Search ........ 548/469, 548/547

See application file for complete search history.

(56) References Cited

U.S. PATENT DOCUMENTS

| 5,057,614 | A |   | 10/1991 | Davis et al. |   |
|---|---|---|---|---|---|
| 5,721,245 | A |   | 2/1998 | Davis et al. |   |
| 6,153,641 | A | * | 11/2000 | Bergstrand et al. | .......... 514/414 |
| 2005/0090483 | A1 | * | 4/2005 | Engler et al. | .......... 514/214.03 |

FOREIGN PATENT DOCUMENTS

| WO | WO98/16528 | 4/1998 |
| WO | WO 00/38675 | 7/2000 |
| WO | WO01/44235 | 6/2001 |
| WO | WO01/44247 | 6/2001 |
| WO | WO 02/10158 | 2/2002 |
| WO | WO02/46183 | 6/2002 |
| WO | WO02/46197 | 6/2002 |

OTHER PUBLICATIONS

FDA mulls drug to slow late-stage Alzheimer's [online],[retrieved on Sep. 23, 2003].Retrieved from the Internet, URL; http://www.cnn.com/2003/HEALTH/conditions/09/24/alzheimers.drug.ap/indexhtml>.*
Cecil Textbook of Medicine, 20th edition (1996), vol. 2, pp. 1992-1996.*
Cecil Textbook of Medicine, 20th edition (1996), vol. 2, pp. 2050-2057.*

* cited by examiner

*Primary Examiner*—Joseph McKane
*Assistant Examiner*—Shawquia Young
(74) *Attorney, Agent, or Firm*—Robert D. Titus

(57) ABSTRACT

The present invention provides kinase inhibitors of Formula (I)

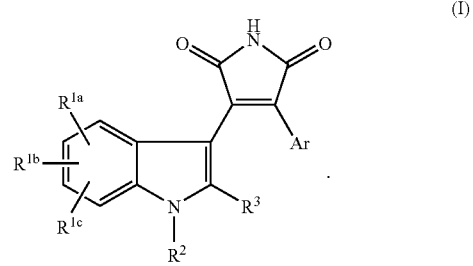

9 Claims, No Drawings

PYRROLE-2, 5DIONE DERIVATIVES AND THEIR USED AS GSK-3 INHIBITORS

This is the national phase application, under 35 USC 371, for PCT/US03/05052, filed 05 Mar. 2003, which, claims the benefit, under 35 USC 119(e), of U.S. provisional application 60/363,375 filed 08 Mar. 2002, and 60/369,433, filed 02 Apr. 2002.

Glycogen synthase kinase-3 (GSK-3) is a serine/threonine protein kinase first discovered as one of a number of kinases capable of phosphorylating and inactivating glycogen synthase, the regulatory enzyme of glycogen synthesis in mammals (Embi, et al., *Eur. J. Biochem.*, 107, 519-527 (1980)). Existing in two isoforms, GSK-3α and GSK-3β, GSK-3 phosphorylates a wide variety of proteins in vitro. The diversity of these proteins suggests a role for GSK-3 in the control of cellular metabolism, growth, and development.

Type I diabetes is characterized by a lack of insulin resulting from the destruction of insulin producing cells in the pancreas. Type II diabetes is characterized by defective insulin secretion and action. The binding of insulin to its receptor initiates a cascade of events resulting in the phosphorylation and inhibition of GSK-3, contributing to the insulin-induced stimulation of glycogen and protein synthesis. Inhibitors of GSK-3 have been shown to mimic the actions of insulin (Coghlan, et al., *Chem. Biol.*, 7, 793-803 (2000)), including the ability to lower blood glucose levels in vivo (Norman, *Drug News Perspect.*, 14, 242-247 (2001)). These recent discoveries suggest that inhibitors of GSK-3 have a potential role in the treatment of diabetes.

Alzheimer's disease is characterized by the micro-tubule-associated protein Tau existing in an abnormally hyperphosphorylated state (Cohen and Frame, *Nature Reviews: Molecular Cell Biology*, 2, 769-776 (October 2001) <www.nature.com/reviews/molcellbio>). GSK-3 phosphorylates many of the hyperphosphorylated sites on Tau in vitro, preventing it from binding to microtubules, making it available to undergo the aberrant filament assembly that may underlie the neuronal degeneration observed in Alzheimer's disease and other neurological disorders. Inhibitors of GSK-3, such as insulin and lithium ions, have been shown to induce a partial dephosphorylation of Tau in neuronal cells (Cross, et al., *J. Neurochem.*, 77, 94-102 (2001)). These discoveries suggest that inhibitors of GSK-3 have a potential role in the treatment of degenerative neurological disorders such as Alzheimer's disease.

WO 98/16528 describes purine derivatives, WO 99/65897 describes pyrimidine and pyridine derivatives, WO 00/38675 describes maleimides, and WO 01/56567 describes diaminothia-zole derivatives that are taught to be inhibitors of GSK-3. Additional GSK-3 inhibitors are necessary to provide treatments for GSK-3 mediated endocrine and neurological disorders. The present invention provides inhibitors of GSK-3.

The present invention provides compounds of Formula I:

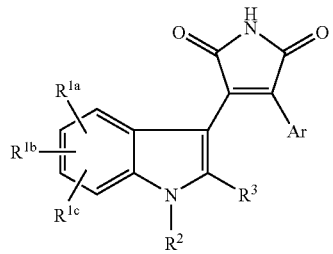

I where:

Ar is benzofur-7-yl optionally substituted in the phenyl ring with $R^8$ and $R^9$, 1-($R^7$)-indol-4-yl, benzofur-4-yl, quinolin-5-yl, quinolin-7-yl, isoquinolin-5-yl, isoquinolin-3-yl, imidazo[1,2-a]pyridin-3-yl, imidazo[1,2-a]pyridin-5-yl, furo[3,2-c]pyridin-7-yl, benzo[1,3]dioxol-4-yl, 2,2-difluorobenzo[1,3]dioxol-4-yl, or 2,3-dihydrobenzofur-7-yl optionally substituted in the phenyl ring with $R^8$ and $R^9$ and in the dihydrofuryl ring with $C_1$-$C_4$ alkyl;

$R^{1a}$ is hydrogen, $C_1$-$C_4$ alkoxy, —$(CH_2)_m$-G, —O—$(CH_2)_m$-G, —halo, $C_1$-$C_4$ alkyl optionally substituted with one to three halo, piperazin-1-yl optionally substituted 1-2 times with —$(CO_2)_n$—$(C_1$-$C_4$ alkyl), or —$(CH_2)$—O—$(CH_2)$—O—$(CH_3)$;

$R^{1b}$ is hydrogen or halo;

$R^{1c}$ is hydrogen or halo;

G is independently at each occurrence hydroxy, $NR^{11}R^{12}$, or piperidin-4-yl;

$R^2$ is hydrogen, $C_1$-$C_4$ alkyl, —$(CH_2)_m$-G, tetrahydropyran-4-yl, 4-($NR^4R^5$)cyclohex-1-yl, 4-hydroxycyclohex-1-yl, 2-azabicyclo[3.2.1]oct-5-yl, the moiety

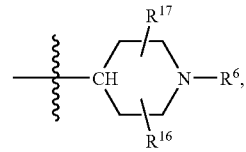

the moiety

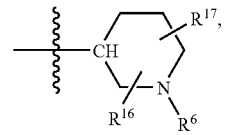

cyclohexan-1-on-4-yl, pyridin-4-yl; and $R^3$ is hydrogen, halo, $C_1$-$C_4$ alkyl, or cyclopropyl; or $R^2$ and $R^3$ taken together represent

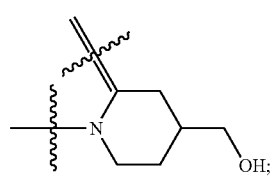

$R^4$ is hydrogen and $R^5$ is hydrogen or $C_1$-$C_4$ alkyl, or $R^4$ and $R^5$ taken together with nitrogen to which they are attached form a pyrrolidine ring;

$R^6$ is hydrogen, benzyl, —$CO_2(C_1$-$C_4$ alkyl), —C(O)—$(C_1$-$C_4$ alkyl)$_n$-$NR^{14}R^{15}$, —C(O)tetrahydropyran-4-yl, —C(O)morpholin-4-yl, —$CH_2$-tetrahydropyran-4-yl, an amino acid residue, —C(O)pyridin-2-yl, —C(O)pyridin-3-yl, —C(O)pyridinyl-4-yl, —C(O)pyrimidin-5-yl, $C_1$-$C_4$ alkyl, —C(O)pyrazin-2-yl, or —$CO_2$—$(C_1$-$C_4$ alkyl)-$(C_1$-$C_4$ alkoxy);

$R^7$ is hydrogen, $C_1$-$C_4$ alkyl, or —$(CH_2)_m$-G;

$R^8$ is —$NHCO_2(C_1\text{-}C_4$ alkyl), —$NHSO_2(C_1\text{-}C_4$ alkyl), halo, amino, —O—$(CH_2)_m$-G, —$NHC(O)(C_1\text{-}C_4$ alkyl), $C_1\text{-}C_4$ alkoxy, hydroxy, —O—$R^{10}$, $C_1\text{-}C_4$ alkyl, $C_1\text{-}C_4$ alkylthio, or —$(CH_2)_m$-G;

$R^9$ is halo;

$R^{10}$ is piperidin-3-yl, piperidin-4-yl, or pyrrolidin-3-yl;

$R^{11}$ and $R^{12}$ are independently selected from the group consisting of hydrogen, $C_1\text{-}C_4$ alkyl, cyclopropylmethyl, benzyl, or, taken together with the nitrogen to which they are attached form a piperidine, 4-hydroxypiperidine, 4-$(C_1\text{-}C_4$ alkyl)piperidine, N—$(R^{13})$-piperazine, or morpholine ring;

$R^{13}$ is hydrogen, C(O)—$(C_1\text{-}C_4$ alkyl), or $C_1\text{-}C_4$ alkyl;

$R^{14}$ and $R^{15}$ are independently hydrogen or $C_1\text{-}C_4$ alkyl;

$R^{16}$ is independently at each occurrence hydrogen, geminal dimethyl, geminal diethyl, a spiro-fused $C_3\text{-}C_6$ cycloalkyl, or $C_1\text{-}C_4$ alkyl optionally substituted with hydroxy; and $R^{17}$ represents hydrogen, $C_1\text{-}C_4$ alkyl, or geminal dimethyl, provided that the total number of carbon atoms between $R^{16}$ and $R^{17}$ does not exceed five;

m is independently at each occurrence 2, 3, 4, or 5;

n is independently at each occurrence 0 or 1; or pharmaceutically acceptable salt thereof, subject to the following provisos:

i) when G is hydroxy, no more than two of $R^{1a}$, $R^2$, $R^7$, or $R^8$ may be —$(CH_2)_m$-G, or —O—$(CH_2)_m$-G; and ii) when G is $NR^{11}R^{12}$, no more than one of $R^{1a}$, $R^2$, $R^7$, or $R^8$ may be —$(CH_2)_m$-G, or —O—$(CH_2)_m$-G.

The present invention also provides a method of treating diabetes in a mammal comprising administering to a mammal in need of such treatment an effective amount of a compound of Formula I.

The present invention also provides a method of treating Alzheimer's disease in a mammal comprising administering to a mammal in need of such treatment an effective amount of a compound of Formula I.

The present invention further provides a method of inhibiting GSK-3 in a mammal comprising administering to a mammal in need of such treatment an effective amount of a compound of Formula I.

The present invention also provides a pharmaceutical formulation comprising a compound of Formula I, in combination with a pharmaceutically acceptable carrier, diluent or excipient.

The present invention further provides a method of stimulating bone deposition in a mammal comprising administering to a mammal in need of such treatment an effective amount of a GSK-3 inhibitor.

The present invention also provides a method of stimulating bone deposition in a mammal comprising administering to a mammal in need of such treatment an effective amount of a compound of Formula I.

Furthermore, this invention provides the use of a compound of Formula I for the manufacture of a medicament for the treatment of diabetes. This invention also provides the use of a compound of Formula I for the manufacture of a medicament for the treatment of Alzheimer's disease. This invention also provides the use of a compound of Formula I for the manufacture of a medicament for the inhibition of GSK-3.

This invention also provides the use of a compound of Formula I for the manufacture of a medicament for the inhibition of GSK-3. Additionally, this invention provides a pharmaceutical formulation adapted for the treatment of diabetes containing a compound of Formula I. Furthermore, this invention provides the use of a compound of Formula I for the manufacture of a medicament for the treatment of diabetes. This invention also provides the use of a compound of Formula I for the manufacture of a medicament for the treatment of Alzheimer's disease. The present invention also provides a formulation adapted for stimulating bone deposition in mammals containing a compound of Formula. The present invention further provides the use of a compound of Formula I for the manufacture of a medicament for stimulating bone deposition.

The following definitions are to set forth the meaning and scope of the various terms used herein. The general terms used herein have their usual meanings.

The term "GSK-3" refers to GSK-3α and/or GSK-3β.

The term "diabetes" is taken to mean Type I and/or Type II diabetes.

The term "effective amount" as used in "an effective amount of a compound of Formula I," for example, refers to an amount of a compound of the present invention that is capable of inhibiting GSK-3.

The general chemical terms used herein have their usual meanings. For example, as used herein, the term "$C_1\text{-}C_4$ alkyl," alone or in combination, denotes a straight-chain or branched-chain $C_1\text{-}C_4$ alkyl group consisting of carbon and hydrogen atoms, examples of which are methyl, ethyl, propyl, isopropyl, butyl, sec-butyl, tert-butyl, and the like. The term "geminal dimethyl" represents two methyl groups attached at the same substitution position. The term "$C_3\text{-}C_6$ cycloalkyl" refers to cyclopropyl, cyclobutyl, cyclopentyl, and cyclohexyl. The term "spiro-fused $C_3\text{-}C_6$ cycloalkyl" refers to a $C_3\text{-}C_6$ cycloalkyl group as defined above bonded to a carbon atom through a spiro linkage.

The term "$C_1\text{-}C_4$ alkoxy," alone or in combination, denotes an alkyl group as defined earlier which is attached via an oxygen atom, such as, for example, methoxy, ethoxy, propoxy, isopropoxy, butoxy, tert-butoxy, and the like. The term "$C_1\text{-}C_4$ alkylthio," alone or in combination, denotes an alkyl group as defined earlier which is attached via a sulfur atom, and includes methylthio, ethylthio, isobutylthio, and the like.

The term "hydroxy," alone or in combination, represents an —OH moiety. As used herein, the term "halo" or "halogen" represents fluorine, chlorine, bromine, or iodine.

The term "amino acid residue" is taken to mean an amino acid moiety selected from the group consisting of alanyl, arginyl, asparaginyl, aspartyl, cysteinyl, glutaminyl, glutamyl, glycyl, histidyl, isoleucyl, leucyl, lysyl, methionyl, phenylalanyl, phenylglycyl, prolyl, seryl, threonyl, tryptophanyl, tyrosyl, and valyl bonded through an acid carbonyl.

It will be understood by the skilled reader that most or all of the compounds of the present invention are capable of forming salts. In all cases, the pharmaceutically acceptable salts of all of the compounds are included in the names of them. The compounds of the present invention are amines, and accordingly react with any of a number of inorganic and organic acids to form pharmaceutically acceptable acid addition salts. Preferred pharmaceutically acceptable salts are those formed with hydrochloric acid.

Although all of the compounds of Formula I are useful GSK-3 inhibitors, certain compounds are preferred. The following paragraphs define preferred classes.

a) Ar is benzofur-7-yl.

b) Ar is 2,3-dihydrobenzofur-7-yl optionally substituted in the phenyl ring with halo.

c) Ar is 2,3-dihydro-6-fluorobenzofur-7-yl.

d) Ar is imidazo[1,2-a]pyridin-3-yl.

e) $R^{1a}$ is —$(CH_2)_m$-G.

f) $R^{1a}$ is —O—$(CH_2)_m$-G.

g) $R^{1b}$ is hydrogen.

h) $R^{1b}$ is fluoro.

i) $R^{1c}$ is hydrogen.

j) $R^{1c}$ is fluoro.

k) G is hydroxy.
l) G is $NR^{11}R^{12}$
m) G is piperidin-4-yl.
n) $R^2$ is —$(CH_2)_m$-G.
o) $R^2$ is 1-($R^6$)-piperidin-4-yl.
p) $R^2$ is 1-($R^6$)-piperidin-4-yl further substituted with methyl.
q) $R^3$ is halo.
r) $R^2$ and $R^3$ taken together represent

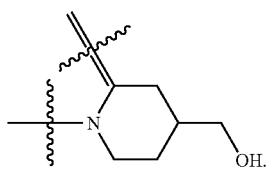

s) $R^6$ is hydrogen.
t) $R^6$ is —C(O)morpholin-4-yl.
u) $R^6$ is —C(O)pyrazin-2-yl.
v) $R^7$ is methyl.
w) $R^7$ is —$(CH_2)_m$-G.
x) $R^8$ is —O—$(CH_2)_m$-G.
y) $R^8$ is halo.
z) $R^8$ is fluoro.
aa) $R^9$ is methoxy.
bb) $R^8$ is hydroxy.
cc) $R^9$ is fluoro.
dd) $R^9$ is chloro.
ee) $R^{11}$ is hydrogen.
ff) $R^{11}$ is methyl.
gg) $R^{11}$ is ethyl.
hh) $R^{12}$ is hydrogen.
ii) $R^{12}$ is methyl.
jj) $R^{12}$ is ethyl.
kk) $R^{13}$ is hydrogen.
ll) $R^{14}$ and $R^{15}$ both are hydrogen.
mm) $R^{14}$ is hydrogen and $R^{15}$ is methyl.
nn) $R^6$ is methyl.
oo) $R^{16}$ is geminal dimethyl.
pp) $R^{17}$ is geminal dimethyl.
qq) The compound is a free base.
rr) The compound is a salt.
ss) The compound is the hydrochloride salt.

The preceding paragraphs may be combined to define additional preferred classes of compounds.

The compounds of Formula I are inhibitors of GSK-3. Thus, the present invention also provides a method of inhibiting GSK-3 in a mammal that comprises administering to a mammal in need of said treatment a GSK-3 inhibiting amount of a compound of Formula I. The present compounds are believed to be useful in treating Type I and/or Type II diabetes. Furthermore, the compounds of the present invention are believed to be useful in the treatment of neurological disorders such as dementias, especially dementia of the Alzheimer's type. The compounds of the present invention are also believed to be useful for the treatment of bipolar disorder.

A further embodiment of the present invention is the use of inhibitors of GSK-3 for rapid bone deposition. This ability to stimulate rapid bone deposition provides a new means to treat a variety of disease states and conditions where it would be beneficial to grow new bone. These disease states include osteoporosis and fraility as well as bone loss due to periodontal disease. Compounds exhibiting this activity will also be useful in promoting wound healing and bone fracture repair.

It is also contemplated that GSK-3 inhibitor mediated bone deposition will improve patient outcomes in joint replacement surgeries by enhancing the attachment of a joint prosthesis to the patient's bone. The use of the compounds of the present invention for the induction of rapid bone deposition is preferred. It is preferred that the mammal to be treated by the administration of the compounds of Formula I is human.

The skilled artisan will appreciate that the introduction of certain substituents will create asymmetry in the compounds of Formula I. The present invention contemplates all enantiomers and mixtures of enantiomers, including racemates. It is preferred that the compounds of the invention containing chiral centers are single enantiomers.

The compounds of the present invention can be prepared by a variety of procedures, some of which are illustrated in the Schemes below. It will be recognized by one of skill in the art that the individual steps in the following schemes may be varied to provide the compounds of Formula I. The particular order of steps required to produce the compounds of Formula I is dependent upon the particular compound being synthesized, the starting compound, and the relative lability of the substituted moieties. Some substituents—such as $R^{1a}$, $R^{1b}$, and $R^{1c}$—have been eliminated in the following schemes for the sake of clarity and are not intended to limit the teaching of the schemes in any way.

Scheme I

Method A

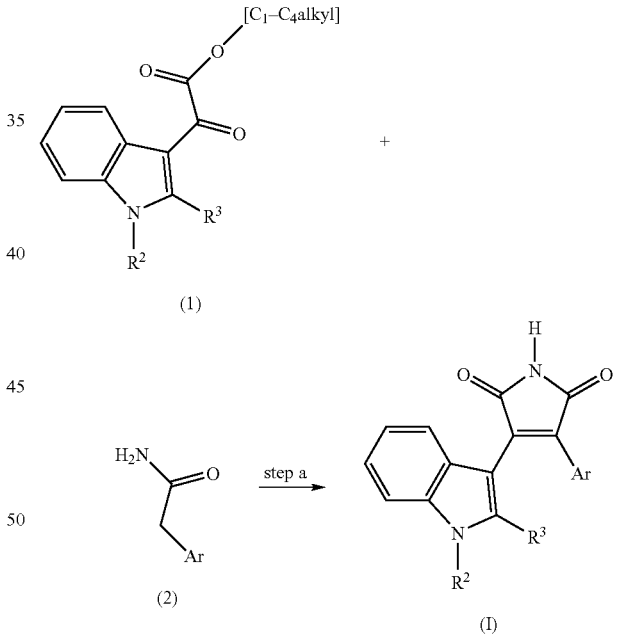

Method B

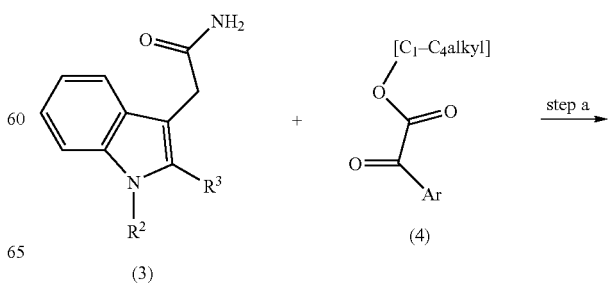

-continued

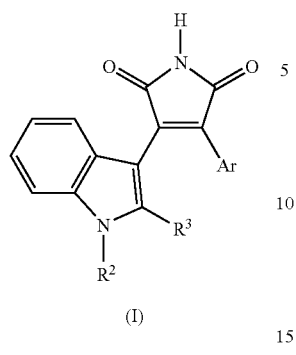

(I)

Scheme I depicts synthetic methods for the formation of the bisarylmaleimides of Formula I via Methods A and B. This reaction is well known in the art. See, for example, Faul, et al., *J. Org. Chem.* 63, 6053-6058 (1998). The oxoacetic acid esters of formula (1) or (4), are reacted with the acetamides of formula (2) or (3), respectively, in a suitable solvent, such as dimethylformamide or tetrahydrofuran, in the presence of a suitable base, such as sodium hydride or preferably potassium tert-butoxide. The reaction is conducted at 0° C. to room temperature, and the reactants are stirred for 1-24 hours. The reaction mixture is treated with a suitable acid, such as hydrochloric acid, after which the mixture is stirred at about ambient temperature for 1-24 hours. The resulting maleimides of Formula I may be isolated by standard techniques, and purified by crystallization or chromatography as necessary or desired.

The requisite oxoacetic acid esters of formulae (1) and (4) can be prepared from appropriately substituted indoles and aryl groups. The formation of oxoacetic acid esters is depicted in Schemes IIa and IIb.

Scheme IIa

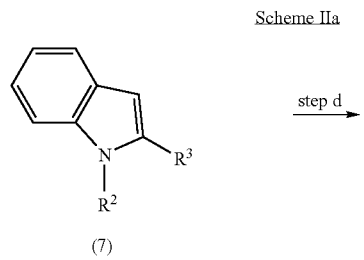

(7)

-continued

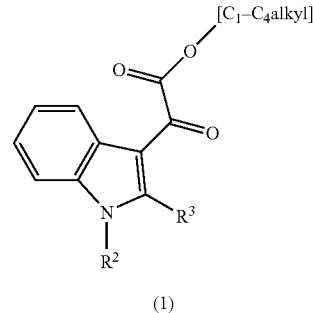

(1)

Scheme IIb

Ar—X $\xrightarrow{\text{step d}}$ Ar
(11)                              (4)

The 3-indolyloxoacetic acid esters of formula (1) are either commercially available or may be prepared as depicted in Scheme IIa. An appropriately substituted indole is reacted with an oxalyl halide, such as oxalyl chloride, in the presence of an organic base, such as 2,6-lutidine or triethylamine, in an appropriate solvent, such as dichloromethane or diethyl ether, to give a compound of formula (1). The reaction is performed at low temperatures, and the mixture is stirred for 1-24 hrs. When an oxalyl halide is used, the mixture is further cooled to about −78° C. and an alkoxide source, such as sodium methoxide, is added in with an appropriate solvent, such as methanol. The resulting oxoacetic acid ester may be isolated by standard techniques and purified by crystallization or chromatography as necessary or desired. The formation of formula (1) in Scheme II is well known in the art; see, for example, Faul, et al., *J. Org. Chem.* 63, 6053-6058 (1998).

In Scheme IIb, compounds of formula (4) are prepared from appropriately substituted halogenated-aryls of formula (11) where X is halo. A compound of formula (11) is subjected to a lithium-halogen exchange, following which the lithium anion is quenched by an oxalate, such as a dialkyl oxalate, as described in Scheme IIa, to give compounds of formula (4). The skilled artisan would also recognize the use of a Grignard reagent quenched with the oxalate at low temperatures as an alternate synthetic method The formation of acetamides is depicted in Scheme III.

Scheme IIIa

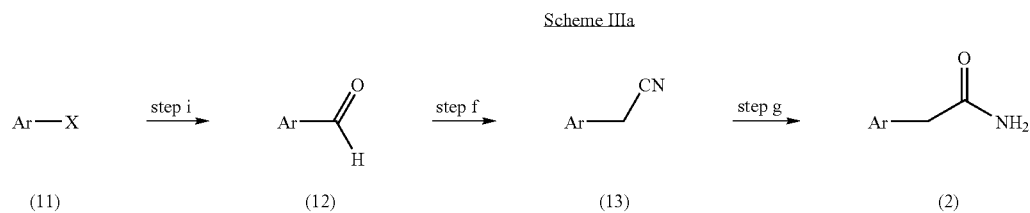

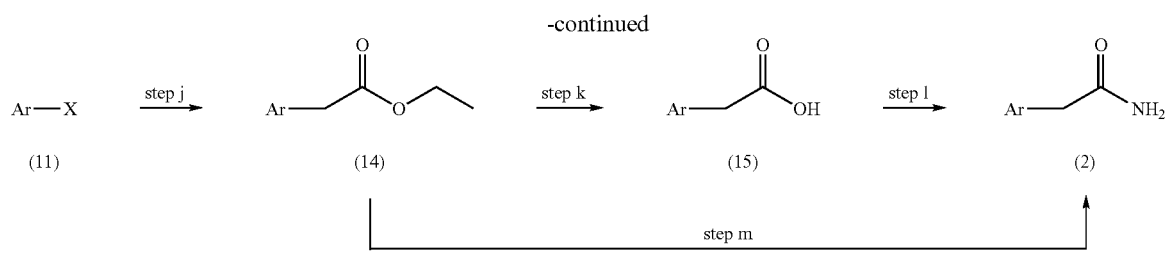

Scheme IIIb

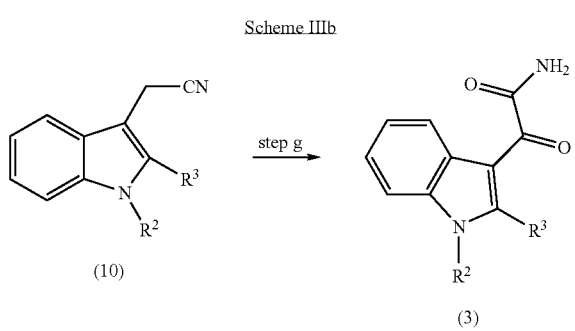

In Scheme IIIa, the compounds of formula (11) are converted to compounds of formula (12) in step i by lithium-halogen exchange, followed by quenching with N,N-dimethylformamide. Compounds of formula (13) are formed in step f, via a phosphorylated cyanohydrin formed in situ from reaction of compounds of formula (12), diethylcyanophosphonate, and lithium cyanide in a suitable solvent, such as tetrahydrofuran. For similar examples of this conversion see, Yoneda, et al, *Tetrahedron Lett.* 30, 3681-3684 (1989); Yoneda, et al., *J. Org. Chem.*, 56, 1827-1832 (1991). Base hydrolysis of the acetonitrile group, step g, gives the acetamides of formula (3).

Also, the skilled artisan would appreciate, as an alternative method, the use of 2-ethoxy-2-oxoethylzinc bromide, with a palladium catalyst, in a suitable solvent, such as tetrahydrofuran, to give compounds of formula (14) via step j. Compounds of formula (14) can then be subjected to base hydrolysis conditions in step k to give compounds of formula (15). Compounds of formula (15) are converted to compounds of formula (2) in step l under standard coupling conditions in the presence of a ammonium source, such as ammonium hydroxide or ammonia gas. Suitable coupling reagents include N,N'-carbonyldiimidazole (CDI), N,N'-dicyclohexylcarbodiimide (DCC), 1-(3-dimethylaminopropyl)-3-ethylcarbodiimide hydrochloride (EDC), and 1-(3-(1-pyrrolidinyl)propyl)-3-ethylcarbodiimide (PEPC). Suitable optional catalysts for the coupling reaction include N,N-[dimethyl]-4-aminopyridine (DMAP). All of the reagents are combined in a suitable solvent—typically dichloromethane, chloroform, tetrahydrofuran, dioxane, or diethyl ether—and are stirred for from 1 to 72 hours at a temperature of from ambient to about the reflux temperature of the solvent. The desired product may be isolated by standard extractive and crystallization techniques, and purified by chromatography or crystallization as necessary or desired.

Alternatively, in step m, the skilled artisan would appreciate that compounds of formula (14) may be reacted to form compounds of formula (2) directly. A compound of formula (14) in a suitable solvent, such as methanol, that has been saturated with ammonia gas, is placed in a sealed container and reacted at elevated temperatures to form compounds of formula (2).

The requisite aryl intermediates for the formation of formula (2) or (4) are commercially available or can be synthetically prepared as described herein.

Conversions of compounds of formula (10) to compounds of formula (3)—involving base hydrolysis of an appropriately substituted indole acetonitrile, similar to step g of Scheme IIIa—are well known and appreciated in the art; see, for example, Larock, *Comprehensive Organic Transformations*, 2$^{nd}$ Ed., John Wiley & Sons, New York, pg. 1988-1989 (1999). The resulting 3-indolylacetamide of formula (3) can be isolated by standard techniques and may be purified by crystallization or chromatography as necessary or desired. This reaction produces appropriately 3-substituted-indoles.

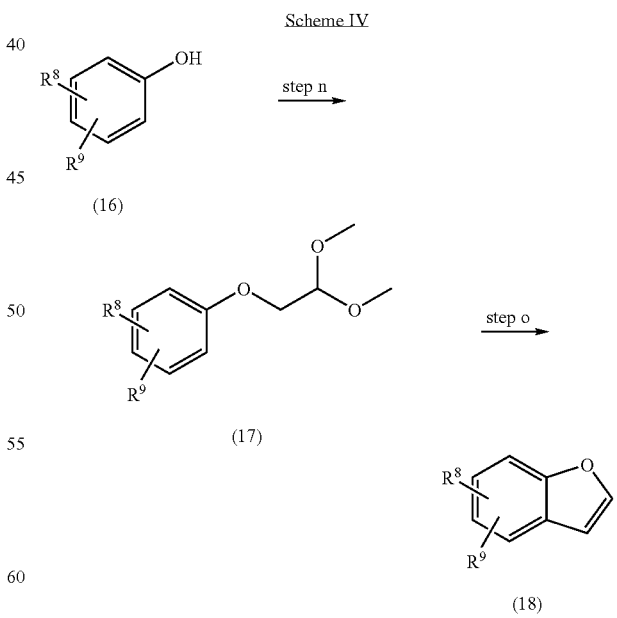

Benzofurans of formula (18) may be derived from compounds of formula (16). As shown in step n, appropriately substituted phenols are O-alkylated with bromoacetaldehyde and a suitable base, such as potassium carbonate. Cyclization is accomplished in a suitable solvent, in which water can be an azeotrope, such as chlorobenzene at refluxing temperatures in step o.

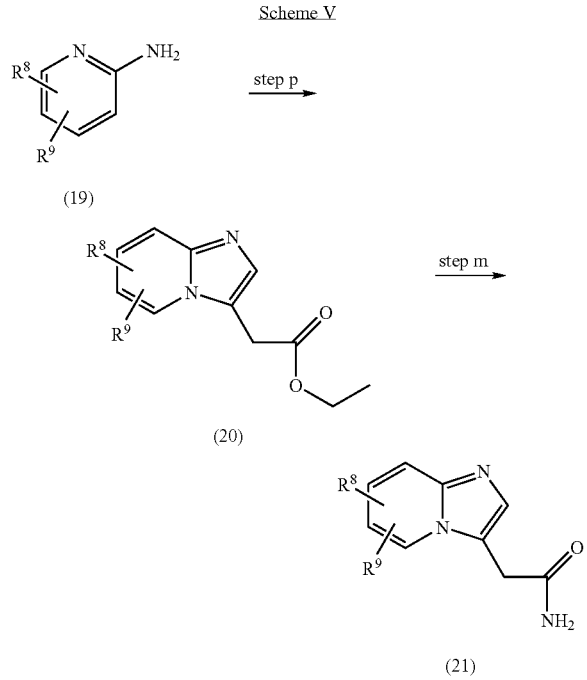

Compounds of formula (21) may be formed as shown in Scheme V. Step p depicts a [2+3] cyclization of optionally substituted 2-aminopyridine with ethyl oxybutenoate in acetonitrile under reflux conditions to afford compounds of formula (20). Formula (20) can be transformed to the acetamide, formula (21), as previously described in step m.

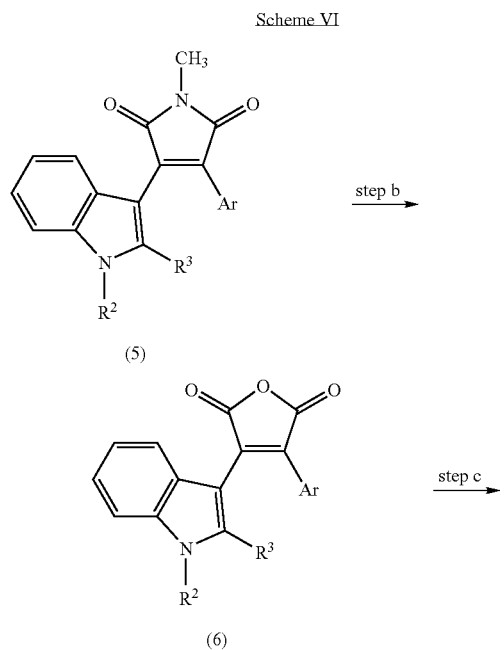

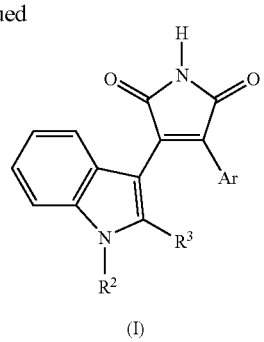

The procedure of Scheme VI is a conversion of N-methyl-pyrrole-2,5-diones, formula (5), to the corresponding furan-2,5-dione, formula (6). This reaction, as shown in step b, can be performed by a suitable base in which both formulae (5) and (6) are synthetic stable intermediates used for the manipulation of the R substituent groups. The furan-diones of formula (6) can be converted into the 1H-pyrrole-2,5-diones of Formula (I) in step c by the use of an alkyl-disilazane reagent. Conversions of this type are well known in the art; see, for example, Davis, et al., *Tetrahedron Lett.*, 31(36), 5201-5204 (1990); and Mayer, et al., *Tetrahedron Lett.*, 37(26), 4483-4486 (1996).

The requisite indoles for Schemes IIa and IIIb are either commercially available or may be prepared by methods well known in the art. Indole syntheses are described in Robinson, *The Fischer Indole Synthesis*, John Wiley & Sons, New York (1983); Hamel, et al., *J. Org. Chem.*, 59, 6372 (1994); and Russell, et al., *Org. Prep. and Procedures Intl.*, 17, 391 (1985).

Many of the compounds of the present invention are not only inhibitors of GSK-3, but are also useful intermediates for the preparation of additional compounds of the present invention. For example, secondary amines may be acylated, alkylated or coupled with simple carboxylic acids or amino acids under standard conditions. Furthermore, ester moieties may be reduced to the corresponding alcohols. These alcohols may then be activated and displaced by a number of nucleophiles to provide other compounds of the invention.

A skilled artisan would recognize several other transformations that can be applied to the synthetic process for production of useful and reactive intermediates for the preparation of additional compounds of the present invention. Such transformations include but are not limited to nucleophilic displacement of halogen with an appropriate amine (see Larock, *Comprehensive Organic Transformation*, 2$^{nd}$ Ed., John Wiley & Sons, New York, pg. 779-780 (1999)), alkylation or acylations of the appropriate amine, O-alkylation of the hydroxy intermediates, or hydroxy-halogen exchange (Larock, *Comprehensive Organic Transformations*, 2$^{nd}$ Ed, John Wiley & Sons, New York, pg. 689-697 (1999)). Further, compounds may be reacted with an appropriate reagent to introduce a suitable amino protecting group such as a formyl group, acetyl group, or preferably a tert-butoxycarbonyl moeity. Techniques for the introduction of these groups are well known to the skilled artisan.

Additionally, in order to substitute alcohol derivatives with a corresponding amine, the skilled artisan would appreciate that necessary intermediates would incorporate certain appropriate leaving groups. Such leaving groups include but are not limited to halides, oxonium ions, alkyl perchlorates, ammonioalkaesulfonate esters, alkyl fluorosulfonates, nonaflates, tresylates, triflates, and sulfonic esters, preferably the mesylate or tosylate. Techniques for the introduction of these groups are also well known to the skilled artisan; see, for example, March, *Advanced Organic Chemistry*, 5th Ed., John Wiley and Sons, New York, pg. 445-449 (2001). The skilled artisan will appreciate that the nitrogen-protecting groups may be removed at any convenient point in the synthesis of the compounds of the present invention. Methods of formation and removal of an amino-protecting group are well known in the art; see, for example, Greene and Wuts, *Protective Groups in Organic Synthesis*, 3rd Ed., John Wiley and Sons, New York, Chapter 7 (1999).

The skilled artisan will also appreciate that not all of the substituents in the compounds of Formula I will tolerate certain reaction conditions employed to synthesize the compounds. These moieties may be introduced at a convenient point in the synthesis, or may be protected and then deprotected as necessary or desired. Furthermore, the skilled artisan will appreciate that in many circumstances, the order in which moieties are introduced is not critical. The particular order of steps required to produce the compounds of Formula I is dependent upon the particular compound being synthesized, the starting compound, and the relative lability of the substituted moieties.

The following preparations and examples further illustrate the preparation of compounds of the present invention and should not be interpreted in any way as to limit the scope. Those skilled in the art will recognize that various modifications may be made while not departing from the spirit and scope of the invention. All publications mentioned in the specification are indicative of the level of those skilled in the art to which this invention pertains.

The terms and abbreviations used in the instant Preparations and Examples have their normal meanings unless otherwise designated. For example "° C.", "N", "mmol", "g", "mL", "M", "HPLC", "IR", "MS(FD)", "MS(IS)", "MS (FIA)", "MS(FAB)", "MS(EI)", "MS(ES)", "UV", and "$^1$H NMR", refer to degrees Celsius, normal or normality, millimole or millimoles, gram or grams, milliliter or milliliters, molar or molarity, high performance liquid chromatography, infra red spectrometry, field desorption mass spectrometry, ion spray mass spectrometry, flow injection analysis mass spectrometry, fast atom bombardment mass spectrometry, electron impact mass spectrometry, electron spray mass spectrometry, ultraviolet spectrometry, and proton nuclear magnetic resonance spectrometry respectively. In addition, the absorption maxima listed for the IR spectra are only those of interest and not all of the maxima observed.

Preparation of Oxoacetic Acid Methyl Ester Intermediates:

PREPARATION 1

2-(1H-Indol-7-yl)-ethanol a) 2-(2-nitrophenyl)-1-(tert-butyldimethylsilyloxy) ethane Add 2-nitrophenethyl alcohol (20 g, 120 mmol) and imidazole (11.4 g, 167 mmol) to dichloromethane (200 mL). Cooled to 0° C. and add solid tert-butyldimethylsilyl chloride (23.4 g, 155 mmol). Stir the mixture at 20° C. for 2 hours and dilute with 1:1 ethyl acetate:diethyl ether. Wash with distilled water, aqueous 3% acetic acid, aqueous 0.5 molar sodium hydrogen carbonate, and saturated sodium chloride. Dry over anhydrous magnesium sulfate, filter, and concentrate under reduced pressure to give 32.4 g (96%) of the title compound as a light yellow oil. $^1$H NMR (400 MHz, CDCl$_3$) δ 7.89 (dd, 1H, J=8.0, 1.2 Hz), 7.50 (dt, 1H, J=7.2, 1.6 Hz), 7.37 (m, 2H), 3.89 (t, 2H, J=6.4 Hz), 3.12 (t, 2H, J=6.4 Hz), 0.83 (s, 9H), 0.06 (s, 6H).

b) 2-(1H-Indol-7-yl)ethanol

Slowly add a 1.0 molar solution of vinylmagnesium bromide in tetrahydrofuran (430 mL, 430 mmol) to a stirred solution of 2-(2-nitrophenyl)-1-(tert-butyldimethylsilyloxy) ethane (27.4, 97.3 mmol) in anhydrous tetrahydrofuran (300 mL) under nitrogen, maintaining the internal temperature of the reaction between −48° C. and −43° C. Stir at −45° C. for 45 minutes. Pour into 1.5 liters of stirring aqueous saturated ammonium chloride and extract with 50% hexane, 50% diethyl ether. Dry over anhydrous magnesium sulfate, filter, and concentrate under reduced pressure. Chromatography on flash silica using a gradient from neat hexane to 7% ethyl acetate in hexane gives 14.4 g of a brown oil, which is a mixture of the tert-butyldimethylsilyl protected product and starting material.

Dissolve the brown oil in tetrahydrofuran (500 mL), add distilled water (100 mL), and cool the mixture to 15° C. Add 1M aqueous hydrochloric acid (100 mL), then stir at 15° C. for 2 hours. Add solid sodium hydrogen carbonate until the reaction mixture is basic, and saturate by adding solid sodium chloride. Separate, filter, and concentrate under reduced pressure to obtain 9.3 of a brown oil, which is a mixture of the title compound and 2-nitrophenethyl alcohol.

Dissolve the brown oil in tetrahydrofuran (100 mL), add absolute ethanol (50 mL), then add 10% palladium on carbon, and stir the mixture under hydrogen (1 atm) at 20° C., for 2 hours. Dilute the mixture with ethyl acetate and filter through a pad of Celite®. Wash with 0.2M aqueous hydrochloric acid, aqueous saturated sodium hydrogen carbonate, and saturated sodium chloride. Dry over anhydrous magnesium sulfate, filter, concentrate under reduced pressure. Chromatography on flash silica using ethyl acetate, hexane gives 6.9 g (44%) of the title compound as an off-white solid. HRMS(M+H)=162.0924.

PREPARATION 2

1-(1,4-Dioxa-spiro[4.5]dec-8-yl)-4-fluoro-1H-indole a) N-(endo-8-Carbethoxy-azabicyclo[3.2.1]octan-3-yl)-indole Dissolve N-Carbethoxy-4-tropinone (11.97 g, 60.71 mmol) and 2-(2,2-dimethoxyethyl)phenylamine (10.0 g, 55.19 mmol) in acetic acid (60 mL) and treat with sodium triacetoxyborhydride (17.54 g, 82.78 mmol). Stir for 4 days at room temperature and than at 70° C. for 6 h. Wash with water (400 mL) and sodium hydroxide, extracting with ethyl acetate. Dry the organic layer over sodium sulphate and evaporate. Purified the remaining oil by flash chromatography (dichloromethane/ethanol 95:5) to afford 13.36 g (34%) of the title compound as white crystals. MS: 299.1 M$^+$+1.

b) 1-(1,4-Dioxa-spiro[4.5]dec-8-yl)-4-fluoro-1H-indole

Dissolve 2-(2',2'-dimethoxyethyl)-3-fluorophenylamine (10 g, 50.2 mmol) and 1,4-cyclohexanedione monoketal (8.62 g, 55.2 mmol) in glacial acetic acid (100 mL), add sodium triacetoxyborohydride (15.96 g, 75.3 mmol) and heat the mixture to 70° C. for 20 h. Cool the reaction mixture in an ice bath and made basic with 5N sodium hydroxide solution. Extract the mixture with methylene chloride, wash with water, brine and dry over sodium sulphate to yield a yellow brown oil (14 g). Flash chromatography using a gradient of ethyl acetate in hexanes yields the pure product as a solid (11.14 g, 77.14%). ESMS m/z (relative intensity) 276.2 (M$^+$+1, 100).

PREPARATION 3

1-(2,2-Dimethoxyethyl)-3-methyl-2-nitrobenzene

Combine 2-nitro-meta-xylene (5 mL, 0.037 mol), N,N-dimethylformamide dimethylacetal (5.4 mL, 1.1 eq) and N,N-dimethylformamide (60 mL) in a flask and reflux under nitrogen for 2 days. Let cool to room temperature then concentrate to approximately one-half volume. Add methanol (40 mL) and trimethylsilylchloride (6.6 mL, 1.4 eq). Reflux overnight. Dilute with ethyl acetate after cooling to room temperature then extract with saturated sodium bicarbonate followed by brine. Dry over magnesium sulfate, filter and concentrate. Purification by column chromatography (9:1 Hexanes:ethyl acetate) gives 1.15 g (14%) product as a light yellow oil. $^1$H NMR (400 MHz, DMSO-d$_6$) δ 2.23 (s, 3H), 2.80 (d, J=5.36 Hz, 2H), 3.19 (s, 6H), 4.45 (m, 1H), 7.32 (m, 2H), 7.42 (m, 1H).

PREPARATION 4

2-(2,2-Dimethoxyethyl)-6-methylaniline

Add to a round bottomed flask containing 1-(2,2-dimethoxyethyl)-3-methyl-2-nitrobenzene (1.1 g) in methanol (50 mL), 10% palladium on carbon (0.13 g). Purge with nitrogen then place under a hydrogen atmosphere using a balloon of hydrogen. Stir overnight at room temperature. Filter through Celite, wash with methanol. Concentrate to give product (0.98 g, 103%) as a clear oil. $^1$H NMR (400 MHz, DMSO-d$_6$) δ 2.05 (s, 3H), 2.71 (d, J=5.36 Hz, 2H), 3.23 (s, 6H), 4.52 (m, 3H), 6.42 (m, 1H), 6.80 (d, J=7.31 Hz, 2H).

PREPARATION 5

1-ethoxy-2-oxoethylzinc bromide

Mix acid washed zinc dust (3.28 g, 50.06 mmol) and cuprous chloride (0.5 g, 5.06 mmol) in anhydrous tetrahydrofuran (10 mL) and reflux for 40 min. Warm to room temperature and add ethyl bromoacetate (2.09 g, 1.4 mL, 12.52 mmol). Stir mixture for 1 h and let stand (without stirring) overnight to facilitate settling of the zinc. Filter the reagent solution before use.

PREPARATION 6

5-Methyl-1H-indole-7-carboxaldehyde a) 5-Methyl-2-nitrobenzaldehyde

Dissolve (5-methyl-2-nitrophenyl)methanol (10 g, 59.88 mmol) in dichloromethane (210 mL). Add 3 Å molecular sieves (54 g) and pyridinium dichromate (22.53 g, 59.88 mmol). Stir at room temperature for 6 hours. Pass the crude reaction mixture through a short silica gel column, and remove under reduced pressure. Purification of the residue by flash chromatography (silica gel, 10-20% ethyl acetate:hexane) gives 7.84 g (79%) of title compound as colorless oil. $^1$H NMR (CDCl$_3$) δ 10.41 (m, 1H), 8.02 (m, 1H), 7.69 (s, 1H), 7.53 (d, 1H), 2.51 (s, 3H).

b) 2-Dibutoxymethyl-4-methyl-1-nitrobenzene

Dissolve 5-methyl-2-nitrobenzaldehyde (7.84 g, 47.52 mmol), 1-butanol (10.55 g, 142.6 mmol) and toluene-4-sulfonic acid (0.5 g) in toluene (200 mL). Heat to reflux, and remove the water using a Dean-Stark apparatus. Heat for 3 hours. Add water, and extract the aqueous layer with ethyl acetate. Combine the organic layers, dry over sodium sulfate, filter, concentrate under reduced pressure, and purify by flash chromatography (1% v/v triethylamine buffered silica gel, 5% ethyl acetate/hexane) to give 14 g (99%) of the title compound as colorless oil.

c) 5-Methyl-1H-indole-7-carboxaldehyde

Dissolve 2-dibutoxymethyl-4-methyl-1-nitrobenzene (13.957 g, 47.373 mmol) in anhydrous tetrahydrofuran (474 mL) under nitrogen, and cool to −40° C. Add vinylmagnesium bromide (190 mL, 190 mmol, 1.0 M in tetrahydrofuran) at −40° C. with stirring. Stir for 40 minutes and add saturated aqueous ammonium chloride. Extract the aqueous layer is extracted with ethyl acetate. Combine the organic layers, dry over sodium sulfate, filter, and concentrate. The crude product is taken on the next step without purification.

Dissolve the crude product from above in tetahydrofuran (160 mL) and cool to 0° C. Add aqueous 0.5 molar hydrochloric acid (20 mL) and stir the mixture at 0° C. for 1 hour. Add saturated aqueous sodium hydrogen carbonate (200 mL) and extract the aqueous layer with ethyl acetate (3×200 mL). Combine the organic layers, dry over anhydrous sodium sulfate, filter, concentrate under reduced pressure, and purify by flash column chromatography (silica gel, 5% ethyl acetate/hexane) to give 4.04 g (54% for 2 steps) of the title compound as a white solid. $^1$H NMR (CDCl$_3$) δ 10.10 (s, 1H), 10.06 (s, 1H), 7.72 (s, 1H), 7.40 (s, 1H), 7.28 (m, 1H), 6.54 (m, 1H), 2.50 (s, 3H).

PREPARATION 7

(5-hydroxybenzofur-7-yl)acetonitrile

Dissolve [5-(tetrahydropyran-2-yloxy)benzofur-7-yl]acetonitrile (3.89 g, 0.015 mol) in methanol (100 mL) and add para-toluene sulfonic acid monohydrate (0.288 g, 0.1 equivalent). After 20 minutes extract with ethyl acetate against water, then wash with brine. Concentration in vacuo affords 2.5 g (95.5%) of the title compound as an off-white solid. HRMS(m/z): Calcd 173.0465 Found 173.0477.

PREPARATION 8

5-Bromoimidazo[1,2-a]pyridine

Add 2-bromo-1,1-diethoxyethane (3.64 g, 18.48 mmol) to a solution of 6-bromopyridin-2-ylamine (1.0 g, 5.77 mmol) in n-butanol (40 ml). Reflux overnight and cool. Filtration of the reaction mixture gives 1.3 g (81%) of 5-bromoimidazo[1,2-a]pyridine hydrobromide as a white solid. ESMS (M++1): 198.9 m/z.

Add saturated sodium bicarbonate (300 ml) to a suspension of 5-bromoimidazo[1,2-a]pyridine hydrobromide (13.0 g, 46.96 mmol) in ethyl acetate. Separate the organic layer, wash with saturated sodium bicarbonate, dry over magnesium sulfate, and concentrate under reduced pressure to give 9.7 g (100%) of the title compound as a white solid.

PREPARATION 9

2-{4-[2-(Tetrahydropyran-2-yloxy)ethoxy]benzofur-7-yl}acetamide a) 7-Bromo-4-[2-(tetrahydropyran-2-yloxy)ethoxy]benzofuran

Potassium carbonate (6.399 g, 46.299 mmol) is added to a solution of 7-bromobenzofur-4-ol (3.266 g, 15.331 mmol) in DMF (30 ml) under nitrogen. 2-(2-bromoethoxy)tetrahydropyran (2.22 mL, 18.386 mmol) is introduced and refluxed at 80° C. for 16 hours. The mixture is diluted with ethyl acetate, washed with water and brine, dried over sodium sulfate, filtered, and concentrated. Purification by flash chromatography and eluting with hexane: ethyl acetate gives 3.538 g (68%) of the title compound as an oil. MS(ES)(m/z) 211 (M+−1-129), 255 (M$^+$−1-85).

b) {4-[2-(Tetrahydropyran-2-yloxy)ethoxy]benzofur-7-yl}acetic acid ethyl ester Combine 7-Bromo-4-[2-(tetrahydropyran-2-yloxy)ethoxy]benzofuran (2.598 g, 7.61 mmol), bis(dibenzylideneacetone) palladium (0.461 g, 0.802 mmol), and 2-dicyclohexylphosphino-2-(N,N-dimethylamino)biphenyl (0.308 g, 0.783 mmol) in tetrahydrofuran (15 ml) under nitrogen. Add bromo(2-ethoxy-2-oxoethyl)zinc (2 equiv.), and heat the mixture at 80° C. for 16 hours. (Knochel, P.; Honed, P.; Eds. Organozinc Reagents: A Practical Approach; Oxford University Press, Inc: London, 1999). Cool the mixture to room temperature, filter through a silica plug eluting with ethyl ether, and concentrate. Purify by flash chromatography and elute with hexane:ethyl acetate to give 1.422 g (54%) of the title compound as an oil. Mass spectrum: electrospray (m/z) 265 (M$^+$+1-85).

c) {4-[2-(Tetrahydropyran-2-yloxy)ethoxy]benzofur-7-yl}acetic acid

Add to a cooled solution (0° C.) of {4-[2-(tetrahydropyran-2-yloxy)ethoxy]-benzofur-7-yl}acetic acid ethyl ester (1.363 g, 3.912 mmol) in dimethylformamide (20 ml) 2M aqueous sodium hydroxide (10 ml), and stir the mixture for 1½ hours at room temperature. Dilute the mixture with ethyl acetate and extract with water. Dilute with methylene chloride (50 ml) and neutralize using 0.1M aqueous hydrochloric acid (100 ml). Separate the layers are separated and extract the water layer with methylene chloride. Combine the methylene chloride layers, dry over sodium sulfate, filter, and concentrate to obtain 0.920 g (68%) of the title compound as an oil. Mass spectrum: electrospray (m/z) 319 (M−1).

d) 2-{4-[2-(Tetrahydropyran-2-yloxy)ethoxy]benzofur-7-yl}acetamide

Combine {4-[2-(Tetrahydropyran-2-yloxy)ethoxy]benzofur-7-yl}acetic acid (0.920 g, 2.872 mmol), and 1,1-carbonyldiimidazole (2.365 g, 14.585 mmol) in tetrahydrofuran (15 ml), and stir for 1 hour under nitrogen. Cool the mixture to 0° C., and add concentrated aqueous ammonium hydroxide (2 ml). Remove the ice bath, and stir the mixture at room temperature for 16 hours. Dilute the mixture with ethyl acetate, wash with water and brine, dry over sodium sulfate, filter, and concentrate. Purification using flash chromatography and eluting with hexane:ethyl acetate gives 0.732 g (80%) of the title product as a white solid. Mass spectrum: electrospray (m/z) 236 (M$^+$+1-85).

PREPARATION 10

2-(Benzofur-4-yl)acetamide

Add 1,1'-carbonyldiimidazole (2.3 g, 14.2 mmol) to a solution of benzofur-4-ylacetic acid (2.5 g, 14.2 mmol) in anhydrous tetrahydrofuran (12 mL) under nitrogen and stir at 20° C. for 4 hours. Bubble anhydrous ammonia through the solution, dilute with anhydrous tetrahydrofuran (10 mL), and stir at 20° C. for 18 hours. Concentrate under reduced pressure, and wash the solid with aqueous sodium hydrogen sulfate and distilled water. Dry under vacuum to obtain 2.3 g (93%) of the title compound as a pale yellow solid. Mass spectrum (ES, m/z) (M+H)=176.1.

PREPARATION 11

N-(7-Cyanomethylbenzofur-4-yl)acetamide a) 2-(2,2-Dimethoxyethoxy)-1-methyl-4-nitrobenzene

Add bromoacetaldehyde dimethylacetal (30.3 g, 179 mmol) to 2-methyl-5-nitrophenol (25 g, 163 mmol) and potassium carbonate (50 g, 362 mmol) in dimethylformamide (200 mL). Stir the mixture and reflux under nitrogen for 2.5 hours. Cool the mixture to 20° C. and add aqueous sodium hydroxide (200 mL, 1 M). Dilute the mixture with hexane and diethyl ether (1:1), then wash with 0.2M aqueous sodium hydroxide and aqueous saturated sodium chloride. Dry over anhydrous magnesium sulfate, filter, and concentrate under reduced pressure. Precipitation of the product from hexane gives 30.6 g (77%) of the title compound, as a tan colored solid. $^1$H NMR (400 MHz, CDCl$_3$) δ 7.78 (dd, 1 H, J=8.4, 2.4 Hz), 7.66 (d, 1 H, J=2.4 Hz), 7.26 (dd, 1 H, J=8.4, 0.8 Hz), 4.76 (t, 1 H, J=4.8 Hz), 4.09 (d, 2 H, J=35.2 Hz), 3.48 (s, 6 H), 2.32 (s, 3 H).

b) 7-Methyl-4-nitrobenzofuran

Add Amberlyst® 15 ion-exchange resin (36 g) to chlorobenzene (700 mL), and heat the mixture to reflux and azeotrope out water, to dry the resin. Dissolve 2-(2,2-dimethoxyethoxy)-1-methyl-4-nitrobenzene (34.8 g, 144 mmol) in chlorobenzene (125 mL), and add this mixture dropwise to the stirring, refluxing reaction mixture under nitrogen over a 15 minute period. Continue refluxing for 1.5 hours, then cool to room temperature. Filter to remove the resin and concentrate under reduced pressure. Dissolve the residue in hexane and diethyl ether (1:1), then wash with 0.5M aqueous sodium hydroxide and aqueous saturated sodium chloride. Dry over anhydrous magnesium sulfate, filter, and concentrate under reduced pressure. Chromatography on flash silica using hexane and ethyl acetate (9:1) and precipitation from hexane and toluene (1:1) yielded 9.7 g (42%) of the title compound as a yellow solid (42%). $^1$H NMR (400 MHz, DMSO-d$_6$) δ 8.36 (d, 1 H, J=2.0 Hz), 8.12 (d, 1 H, J=8.4 Hz), 7.44 (d, 1 H, J=2.4 Hz), 7.38 (d, 1 H, J=8.8 Hz), 2.59 (s, 3 H).

c) Dimethyl[2-(4-nitrobenzofur-7-yl)vinyl]amine

Add 7-methyl-4-nitrobenzofuran (3.5 g, 19.7 mmol) to tert-butoxybis(dimethylamino)methane (10.3 g, 59.1 mmol), and reflux the mixture under nitrogen for 40 minutes. Concentrate under reduced pressure, dissolve in xylenes (50 mL), concentrate under reduced pressure, and dry under vacuum to obtain 4.9 g (100%) of the title compound as a deep red-brown solid. HRMS (M+H)=233.0928.

d) (4-Nitrobenzofur-7-yl)acetonitrile

Add dimethyl[2-(4-nitrobenzofur-7-yl)vinyl]amine (4.8 g, 20.6 mmol) and hydroxylamine-O-sulfonic acid (4.6 g, 40.6 mmol) to dimethylformamide (45 mL) and stir at room temperature for 15 minutes. Heat at 100° C. under nitrogen for 1 hour, cool to room temperature, dilute with diethyl ether, and wash with water and aqueous saturated sodium chloride. Dry over anhydrous magnesium sulfate, filter, and concentrate under reduced pressure. Chromatography on flash silica using 85% hexane, 15% ethyl acetate gives 2.9 g (64%) of the title compound as a light brown solid. Mass spectrum (ES, m/z) (M−1)=200.9.

d) N-(7-Cyanomethylbenzofur-4-yl)acetamide

Add (4-nitrobenzofur-7-yl)acetonitrile (600 mg, 2.96 mmol), acetic anhydride (600 mg, 5.88 mmol), and 5% palladium on carbon (300 mg) to tetrahydrofuran (25 mL). Stir under hydrogen (1 atm) for 45 minutes. Dilute with ethyl acetate, filter through a pad of Celite®, and concentrate under reduced pressure. Chromatograph on flash silica using 75% ethyl acetate, 25% hexane gives 430 mg (67%) of the title compound as an off-white solid. HRMS (M+H)=215.0816.

Oxoacetic Acid Formation:

PREPARATION 12

{5-[3-(tert-Butyldimethylsilyloxy)propoxy]-1-isopropyl-1H-indol-3-yl}oxoacetic acid methyl ester Dissolve 5-[3-(tert-butyldimethyl-silyloxy)propoxy]-1-isopropyl-1H-indole (0.43 g, 1.124 mmol) in tetrahydrofuran (40 mL). Add 2,6-lutidine (0.43 mL, 3 eq) and cool to 0° C. Add oxalyl chloride dropwise and stir for 1.5 hours then cool to −78° C., add methanol (0.1 mL, 2 eq) and treated with sodium methoxide (25% w/w in methanol, 22.5 mL). Stir for 1 hour then dilute with ethyl acetate and extract with saturated sodium bicarbanate then brine. Dry over magnesium sulfate, filter and concentrate. Purification by column chromatography (4:1 hexanes:ethyl acetate) affords the title compound as a light yellow oil. MS (ES, m/z): 434.3 (M+1).

The following compounds are prepared in a similar manner:

| PREP. # | Product | Physical Data |
|---|---|---|
| 13 | {7-[3-(tert-Butyldimethyl-silyloxy)propyl]-1-isopropyl-1H-indol-3-yl}oxoacetic acid methyl ester | MS(ES, m/z): (M+1) 418.2 |
| 14 | (2-cyclopropyl-1H-indol-3-yl)oxoacetic acid methyl ester | MS(ES, m/z): (M+1) 244.0 |
| 15 | (2-isopropyl-1H-indol-3-yl)oxoacetic acid methyl ester | MS(ES, m/z): (M+1) 246 |
| 16 | [N-(endo-8-Carbethoxy-azabicyclo[3.2.1]octan-3-yl)-indol-3-yl]oxoacetic acid methyl ester | MS(ES, m/z): (M+1) 384 |
| 17 | [1-(1,4-Dioxa-spiro[4.5]dec-8-yl)-4-fluoro-1H-indol-3-yl]oxoacetic acid methyl ester | $^1$H NMR(DMSO-d6) δ 8.44(s, 1H), 7.62(d, J=8.07Hz, 1H), 7.33(m, 1H), 7.06(m, 1H), 4.64(m, 1H), 3.94~3.88(m, 4H), 3.87(s, 3H), 2.00(m, 4H), 1.80(m, 4H) |
| 18 | [1-(1,4-Dioxa-spiro[4.5]dec-8-yl)-1H-indol-3-yl]oxoacetic acid methyl ester | MS(ES, m/z): 344.17(M$^+$+1) |
| 19 | [5-(2-tert-butoxyethoxy)-N-methylindol-3-yl]oxoacetic acid methyl ester | MS(ES, m/z): 278(M$^+$+1-56). |
| 20 | 4-(3-Methoxyoxalylindol-1-yl)-2-methylpiperidine-1-carboxylic acid tert-butyl ester | MS(ES, m/z): (M+1) 401.2 |
| 21 | Cis 4-(3-Methoxyoxalyl-indol-1-yl)-3-methylpiperidine-1-carboxylic acid tert-butyl ester | ES(M+1): 401.2 |
| 22 | (Imidazo[1,2-a]pyridin-3-yl)oxoacetic acid methyl ester | ESMS(M$^+$+1): 204.9 m/z. |

PREPARATION 23

(5-fluorobenzofur-7-yl)oxoacetic acid ethyl ester

Dissolve 7-bromo-5-fluorobenzofuran (2 g, 9.3 mmol) in 5 ml tetrahydrofuran under nitrogen. Add magnesium turnings (0.25 g, 1.1 equivalents) and heat to reflux to facilitate Grignard formation. In a separate flask place diethyl oxalate (1.3 mL, 2 equivalents) in 3 mL tetrahydrofuran, and cool to 0° C. under nitrogen. When Grignard formulation is complete, add via canula to the diethyl oxalate solution. Stir the reaction for 2-4 hours while slowly warming to 20° C. Extract with diethyl ether. Wash organic layer with brine. Dry over magnesium sulfate, filter and concentrate to a light yellow oil. Purifacation by column chromatography (4:1 hexanes:ethyl acetate) affords 1.74 g (79%) of an oil which solidifies upon standing. MS (ES, m/z): 237.0 (M+1).

The following compounds may be prepared in a similar manner:

| PREP. # | Product | Physical Data |
|---|---|---|
| 24 | (Benzofur-7-yl)oxoacetic acid methyl ester | ES(M+1) 218.9 |
| 25 | (4-Methoxybenzofur-7-yl)-oxoacetic acid ethyl ester | ES(M+1) 248.9 |
| 26 | (5-Methoxybenzofur-7-yl)-oxoacetic acid ethyl ester | ES(M+1) 249.0 |
| 27 | (6-Methoxybenzofur-7-yl)-oxoacetic acid ethyl ester | 1H NMR(400MHz, CDCl3) δ 1.41(t, J=7.31Hz, 3H), 4.40(m, 2H), 6.74(d, J=1.95Hz, 1H), 6.94(d, J=8.78Hz, 1H), 7.68(d, J=2.44Hz, 1H), 7.78(d, J=8.23Hz, 1H) |
| 28 | (Benzofur-7-yl)oxoacetic acid methyl ester | ES(M+1) 218.9 |
| 29 | (4-Methoxybenzofur-7-yl)-oxoacetic acid ethyl ester | ES(M+1) 248.9 |
| 30 | (5-Methoxybenzofur-7-yl)-oxoacetic acid ethyl ester | ES(M +1) 249.0 |
| 31 | (6-Methoxybenzofur-7-yl)-oxoacetic acid ethyl ester | 1H NMR(400MHz, CDCl3) δ 1.41(t, J=7.31Hz, 3H), 4.40(m, 2H), 6.74(d, J=1.95Hz, 1H), 6.94(d, J=8.78Hz, 1H), 7.68(d, J=2.44Hz, 1H), 7.78(d, J=8.23Hz, 1H) |

-continued

| PREP. # | Product | Physical Data |
|---|---|---|
| 32 | Imidazo[1,2-a]pyridin-5-yloxoacetic acid ethyl ester | |

PREPARATION 33

{1-[3-(tert-Butyldimethyl-silyloxy)propyl]-1H-indol-4-yl}-oxoacetic acid methyl ester Add tert-butyl lithium (88.1 ml, 149.8 mmol, 1.7 M in hexane) to a solution of 4-Bromo-1-[3-(tert-butyldimethylsilyloxy)propyl]-1H-indole (22.0 g, 59.92 mmol) in anhydrous tetrahydrofuran (100 ml) at −78° C. Stir the reaction at −78° C. for 20 min. Transfer the mixture into a solution of dimethyl oxalate (24.8 g, 209.72 mmol) in tetrahydrofuran (400 ml) at −40° C. via a dry-ice cooled cannula. Upon complete addition, stir the reaction at −78° C. for 15 minutes and slowly warm to room temperature. Quench the reaction with saturated aqueous ammonium chloride and extract into ethyl acetate. Combine the organic layers, dry over magnesium sulfate, and concentrate under reduced pressure. Purification by flash chromatography and eluting with ethyl acetate:hexane gradient (100% hexane to 15% ethyl acetate: hexane over 90 minutes) gives the title compound (16.89 g, 75%), as a light brown oil. ESMS (M$^+$+1): 376.2 m/z.

Using a similar method as above the following compounds may be prepared and isolated:

| PREP. # | Product | Physical Data |
|---|---|---|
| 34 | (1-Methyl-1H-indol-4-yl)oxoacetic acid methyl ester | HRMS(M+H): 218.0826 |
| 35 | {1-[2-(tert-Butyl-dimethyl-silyloxy)-ethyl]-6-methoxy-1H-indol-3-yl}oxoacetic acid methyl ester | ESMS(M$^+$+1) 392.1 m/z. |
| 36 | (Benzofur-7-yl)oxoacetic acid methyl ester | HRMS(M+H): 205.0501 |
| 37 | 4-(Methoxybenzofur-7-yl)oxoacetic acid ethyl ester | HRMS(M+Na): 271.0570 |
| 38 | 5-(Methoxybenzofur-7-yl)oxoacetic acid ethyl ester | ES(m/z)(M+1)=249.0 |
| 39 | (5-Benzyloxybenzofur-7-yl)oxoacetic acid methyl ester | HRMS(ES+): 325.12 |

PREPARATION 40

(Isoquinolin-5-yl)oxoacetic acid methyl ester

5-Aminoisoquinoline (20 g, 139 mmol) is dissolved in hydrobromic acid (48%, 100 mL) in a 500 ml round bottom flask, and then a solution of sodium nitrite (9.6 g, 139 mmol) in water (50 mL) added cautiously at 0° C. The white slurry turns bright red upon complete addition of the salt, and then this solution is transferred to another 500 mL vessel containing CuBr (25 g, 174 mmol) stirring in hydrobromic acid (48%, 200 mL) at 75° C. This transfer is performed slowly and carefully. After complete addition, the mixture is allowed to stir at 75° C. for one hour, then cooled to room temperature, and kept stirring overnight. The mixture is then placed onto an ice bath and some ice added to the solution, then basified using sodium hydroxide aqueous solution (20%, 250 mL) solution. Then slurry is filtered and then filtrate is extracted with diethyl ether. The solid and the extract are then combined and sonicated for one hour in chloroform. This sludge is filtered through a plug of Celite, and the chloroform removed by rotovap. The final compound is obtained in pure form by column chromatography in chloroform with 36% yield, 10.4 g (50 mmol) of 5-Bromo-isoquinoline. MS (ES, m/z): 208.0 (M$^+$($^{79}$Br)+1), 210.0 (M$^+$($^{81}$Br)+1).

Tert-BuLi (1.7 M pentane, 27.2 mL, 46.3 mmol) is added to dry THF (195 mL) at −78° C., after few minutes, a solution of 5-bromo-isoquinoline (6.42 g, 30.86 mmol) in THF (5 mL) is added via syringe dropwise. The resulting solution is allowed to stir at −78° C. for 45 minutes, then dimethyl oxalate (11 g, 93 mmol) is added in one portion. After 30 min at −78° C., the reaction is quenched using saturated ammonium chloride solution, diluted with 200 mL EtOAc, and then the TB is removed by rotovap. The residue is diluted with saturated ammonium chloride solution extracted with EtOAc (2×200 mL). The organic layers are combined and washed with 1×75 mL water and 1×75 mL brine, dried over anhydrous sodium sulfate, then concentrated. The material is then purified using flash column chromatography, 20% EtOAC/Hexanes, to yield 3.91 g, 59% of isoquinolin-5-yloxoacetic acid methyl ester. MS (ES, m/z): (M$^+$30 1) 216.1

PREPARATION 42

(5-Methoxybenzofur-7-yl)acetic acid ethyl ester

Dissolve 7-bromo-5-methoxybenzofuran (6.0 g, 26.43 mmol), bis(dibenzylideneacetone)palladium (1.32 g, 2.3 mmol) and 2-dicyclohexylphosphino-2'-(N,N-dimethylamino)biphenyl (2.7 g, 6.86 mmol) in anhydrous tetrahydrofuran (36 mL), add freshly prepared 2-ethoxy-2-oxoethylzinc bromide in tetrahydrofuran (66 mL). Heat at 50-60° C. for 5 h. Cool and filter mixture through celite and evaporate to a thick red-brown oil (30 g). Purify by flash chromatography using a gradient of ethyl acetate in hexanes yields the pure compound as a thick yellow oil (6.2 g, quant). ESMS m/z (relative intensity) 235.2 (M++H+, 10), 161.1 (M+−CO2Et+H+, 100).

Acetamide Formation:

PREPARATION 43

4,5-Difluorobenzofur-7-carboxaldehyde

Dissolve 7-Bromo-4,5-difluorobenzofuran (5.0 g, 23.5 mmol) in anhydrous tetrahydrofuran (15 mL) under nitrogen and add magnesium metal turnings (712 mg, 29.3 mmol). Stir and warm the reaction to 50° C. to initiate the Grignard reagent formation. After the exothermic reaction subsides, reflux for 30 minutes. Dilute the solution with tetrahydrofuran (15 ml) and cool to 25° C. Add the Grignard reagent dropwise via cannula to a stirring solution of N,N-dimethylformamide (10.2 g, 139 mmol) in tetrahydrofuran (25 mL) at −78° C. under nitrogen. Stir the reaction at 0° C. for 1 hour and quench with aqueous saturated ammonium chloride. Dilute with diethyl ether, wash with distilled water, and aqueous saturated sodium chloride. Dry the organic phase over anhydrous magnesium sulfate, filter, and concentrate under reduced pressure. Chromatograph on flash silica using a gradient from neat hexane to 50% ethyl acetate in hexane to obtain 2.65 g (69%) of the title compound as an off-white solid. HRMS (M+)=182.0179.

Using similar procedures the following aldehydes may be prepared and isolated:

| PREP. # | Product | Physical Data |
|---|---|---|
| 44 | (4-Methoxybenzofur-7-yl)carboxaldehyde | 1H NMR(400MHz, DMSO-$d_d$)10.1(s, 1H), 8.06(s, 1H), 7.85(d, J=9Hz, 1H), 7.04(m, 2H, 4.0(s, 2H) |
| 45 | (5-Methoxybenzofur-7-yl)carboxaldehyde | |
| 46 | (4-Fluorobenzofur-7-yl)carboxaldehyde | 1H NMR(400MHz, DMSO-$d_d$) 10.21(s, 1H), 8.21(d, J=2Hz, 1H), 7.89(dd, J=8, 8Hz, 1H), 7.28(dd, J=8, 8Hz, 1H), 7.2(d, J=2Hz, 1H) |
| 47 | Benzofur-7-carboxaldehyde | HRMS(M)=146.0364 |
| 48 | 5-[(tetrahydropyran-2-yloxy)benzofur-7-yl]carboxaldehyde | MS(ES, m/z): 246.9(M+1). |

PREPARATION 49

1-[3-(tert-Butyldimethylsilyloxy)propyl]-1H-indole-4-carboxaldehyde

Add tert-butyl lithium (27.07 ml, 46.03 mmol, 1.7 M in pentane) to a solution of 4-Bromo-1-[3-(tert-butyldimethylsilyloxy)propyl]-1H-indole (6.76 g, 18.41 mmol) in anhydrous tetrahydrofuran (100 ml) at −78° C. Stir the reaction at −78° C. for 30 min, quench with N,N-dimethylformamide (4.7 ml, 64.45 mmol), warm to 0° C., quench with pH7 buffer, and extract into ethyl acetate. Combine the organic layers, dry over magnesium sulfate, and concentrate under reduced pressure. Purification by flash chromatography and eluting with ethyl acetate:hexane gradient (100% hexane to 50% ethyl acetate:hexane over 45 minutes) gives the title compound, (4.81 g, 82%) as a clear oil. ESMS (M++1): 318.2 m/z.

Using similar procedures the following aldehydes may be prepared and isolated:

| PREP. # | Product | Physical Data |
|---|---|---|
| 50 | 1-[3-(tert-Butyldimethylsilyloxy)propyl]-1H-indole-4-carboxaldehyde | ESMS(M++1): 318.2 m/z |
| 51 | 1-Methyl-1H-indole-4-carboxaldehyde | HRMS(M+H)=160.0760 |
| 52 | (4,5-Difluorobenzofur-7-yl)carboxaldehyde | HRMS(M+)=182.0179. |
| 53 | (5-Fluorobenzofur-7-yl)carboxaldehyde | 1H NMR(400MHz, DMSO-dd) 10.25(s, 1H), 8.25(d, J=2Hz, 1H), 7.87(dd, J=8, 3Hz), 7.65(J=8, 3Hz), 7.1(d, J=2, 1H). |
| 54 | (5,6-Difluorobenzofur-7-yl)carboxaldehyde | HRMS(M+) 182.0179 |
| 55 | (6-Fluorobenzofur-7-yl)carboxaldehyde | ESMS(M++) 165.0 |

PREPARATION 56

{1-[3-(tert-Butyldimethylsilyloxy)propyl]-1H-indol-4-yl}acetonitrile

Add 1-[3-(tert-Butyldimethylsilyloxy)propyl]-1H-indole-4-carboxaldehyde (2.34 g, 14.4 mmol) and lithium cyanide tetrahydrofuran complex (LiCN*1.5 THF, 204 mg, 1.44 mmol) to tetrahydrofuran (40 mL) under nitrogen. Add dropwise neat diethyl cyanophosphonate (2.8 mL, 18.4 mmol) to the stirring reaction mixture. Stir at room temp under nitrogen for 60 hours. Add 2-methyl-2-propanol (1.4 mL, 14.6 mmol). Add the reaction mixture via cannula to a stirred 0.1 molar solution of samarium(II) iodide in tetrahydrofuran (360 mL, 36.0 mmol) at 25° C. under nitrogen. If the resulting reaction mixture is not deep blue add additional samarium(II) iodide solution until deep blue color persists. Stir the reaction at 25° C. for 1 hour. Concentrate under reduced pressure, dilute with ethyl acetate, diethyl ether (1:1), wash with aqueous 0.1 molar hydrochloric acid, and aqueous saturated sodium chloride. Dry the organic phase over anhydrous magnesium sulfate, filter, and concentrate under reduced pressure. Chromatograph on flash silica using a gradient from neat hexane to 25% ethyl acetate in hexane to obtain 2.1 g (84%) of the title compound as an off-white solid. 1H NMR (400 MHz, DMSO-$d_d$) 7.43 (d, J=8 Hz, 1H), 7.38 (m, 1H), 7.14 (m, 1H), 7.0 (d, J=8 Hz, 1H), 6.54 (m, 1H), 4.23 (t, J=7, 2H), 4.18 (s, 3H), 3.5 (t, J=7 z, 2H), 1.9 (m, 2H), 0.85 (s, 9H), 0.0 (s, 6H).

Using similar method as above the following nitriles may be prepared and isolated:

| PREP. # | Product | Physical Data |
|---|---|---|
| 57 | (1-Methyl-1H-indol-4-yl)acetonitrile | HRMS(M+H)=171.0939 |
| 58 | (1H-Indol-7-yl)acetonitrile | HRMS(M+)=156.0687 |
| 59 | (4-Methoxybenzofur-7-yl)acetonitrile | 1H NMR(400MHz, DMSO-$d_d$) 7.99(d, J=2Hz, 1H), 7.23(d, J=8Hz, 1H), 6.98(d, J=2Hz, 1H) 6.8(d, J=8Hz, 1H), 4.16(s, 2H), 3.88(s, 3H) |
| 60 | (5-Methoxybenzofur-7-yl)acetonitrile | 1H NMR(400MHz, DMSO-$d_d$) 8.02(d, J=2.2Hz, 1H), 7.17(d, J=2.2Hz, 1H), 6.9(m, 2H), 4.24(s, 3H) |
| 61 | (4-Fluorobenzofur-7-yl)acetonitrile | 1H NMR(400MHz, DMSO-$d_d$) 8.15(d, J=2.2Hz, 1H), 7.33(m, 1H), 7.17-7.1(m, 2H), 4.26(s, 2H) |
| 62 | (4,5-Difluorobenzofur-7-yl)acetonitrile | 1H NMR(400MHz, DMSO-$d_d$) 8.2(d, J<1Hz, 1H), 7.42(m, 1H), 7.22(d, J<1Hz, 1H), 4.28(s, 2H)(carried further without purification) |
| 63 | (5-Fluorobenzofur-7-yl)acetonitrile | 1H NMR(400MHz, DMSO-$d_d$) 8.15(d, J=2Hz, 1H), 7.47(dd, J=8, 2Hz, 1H), 7.18(dd, J=8, 2Hz, 1H), 7.01(d, J=2Hz, 1H), 4.3(s, 2H) |
| 64 | (5,6-Difluorobenzofur-7-yl)acetonitrile | ESMS(M−1): 192.3 |
| 65 | (6-Fluorobenzofur-7-yl)acetonitrile | 1H NMR(400MHz, CDCl$_3$-d6) 7.62(d, J=2.44Hz, 1H), 7.47(m, 1H), 7.00(m, 1H), 6.72(d, J=2.44Hz, 1H), 3.91(s, 2H) |
| 66 | (Benzofur-7-yl)acetonitrile | HRMS(M)=157.0524 |
| 67 | [5-(tetrahydro-pyran-2-yloxy)benzofur-7-yl]acetonitrile | 1H NMR(400MHz, CDCl3) δ 1.70(m, 6H), 3.54(m, 1H), 3.88(m, 1H), 3.91(s, 2H), 5.34(t, J=3.17Hz, 1H), 6.67(d, J=2.20Hz, 1H), 7.01(d, J=1.95Hz, 1H), 7.20(d, J=2.44Hz, 1H), 7.55(d, J=2.20Hz, 1H). |

PREPARATION 68

2-{1-[3-(tert-Butyldimethylsilyloxy)propyl]-1H-indol-4-yl}acetamide

Add {1-[3-(tert-Butyldimethylsilyloxy)propyl]-1H-indol-4-yl}acetonitrile (1.9 g, 11.0 mmol) to 2-methyl-2-propanol (20 mL). Heat to reflux under nitrogen and add potassium hydroxide pellets (7.4 g, 132 mmol). Stir and reflux under nitrogen for 30 minutes. Pour solution off of the excess potassium hydroxide and dilute with ethyl acetate. Wash with a 1:1 mixture of aqueous saturated sodium chloride, aqueous saturated sodium hydrogen carbonate. Dry the organic phase over anhydrous magnesium sulfate, filter, and concentrate under reduced pressure. Rinse the solid with cold diethyl ether and dry under vacuum to obtain 1.62 g (77%) of the title compound as an off-white solid. ESMS ($M^++1$): 347.2.

Using similar methods as above the following acetamides are prepared and isolated:

| PREP. # | Product | Physical Data |
|---|---|---|
| 69 | 2-(1-Methyl-1H-indol-4-yl)acetamide | HRMS(M+H)=189.1028 |
| 70 | 2-(1H-Indol-7-yl)acetamide | 1H NMR(400MHz, DMSO-d$_d$) 10.9(bs, 1H), 7.44-7.37(m, 2H), 7.32(dd, J=2, <1), 6.98-6.91(m 3H), 6.41(m, 1H), 3.62(s, 2H) |
| 71 | 2-(4-Methoxybenzofur-7-yl)acetamide | ESMS($M^++1$) 206.0 |
| 72 | 2-(5-Methoxybenzofur-7-yl)acetamide | 1H NMR(400MHz, DMSO-d$_d$) 7.91(d, J=2Hz, 1H), 7.5(bs, 1H), 7.1(d, J=2Hz, 1H), 6.96(bs, 1H), 6.85(d, J=2HZ, 1H) 6.8(d, J=2Hz, 1H), 3.74(s, 3H), 3.61(s, 2H) |
| 73 | 2-(4-Fluorobenzofur-7-yl)acetamide | HRMS(M+1)=194.0617 |
| 74 | 2-(4,5-Difluorobenzofur-7-yl)acetamide | 1H NMR(400MHz, DMSO-d$_d$) 8.1(d, J=2Hz, 1H), 7.55(bs, 1H), 7.27(m, 2H), 7.14(d, J=2Hz, 1H), 7.01(bs, 1H), 3.65(s, 2H) |
| 75 | 2-(5-Fluorobenzofur-7-yl)acetamide | ESMS($M^++1$): 194.1 |
| 76 | 2-(5,6-Difluorobenzofur-7-yl)acetamide | 1H NMR(400MHZ, DMSO-d$_d$) 8.08(d, J=2.2, 1H), 7.63(bs, 1H), 7.59(dd, J=8, 8Hz, 2H), 7.09(bs, 1H), 6.9(d, J=2.2Hz, d), 3.75(s, 3H). |
| 77 | 2-(6-Fluorobenzofur-7-yl)acetamide | ESMS($M^++1$): 194.0 |
| 78 | 2-(Benzofur-7-yl)acetamide | HRMS(M+H)=176.0717 |
| 79 | 2-(Furo[3,2-c]pyridin-7-yl)acetamide | ESMS: (M++1): 177.1 m/z. |
| 80 | 2-(4-Acetylaminobenzofur-7-yl)acetamide | HRMS(M+H)=255.0733 |
| 81 | 2-[5-(1-benzylpiperidin-4-yloxy)benzofur-7-yl]acetamide | MS(ES, m/z): 365.1(M+1) |
| 82 | 1-(3-Hydroxypropyl)indole-3-acetamide | HRMS(M+H)=233.1291. |
| 83 | 1-(tert-butoxycarbonyl)-4-(7-carbamoyl-methylbenzofur-5-yloxy)piperidine | MS(ES, m/z): 275.1(product minus Boc), (M+1) |

PREPARATION 84

2-(8-Hydroxymethyl-6,7,8,9-tetrahydropyrido[1,2-a] indol 10-yl)acetamide

Dissolve the indole (3.54 mmol) and N,N,-dimethylmethyleneammonium chloride (0.372 g, 4.00 mmol) in dichloromethane (15 mL), stir the mixture is at room temperature for 24~72 h. under nitrogen. Wash with water (5 mL), follow by addition of base to neutralize the acid (3.6 mL, 1M NaOH). Extract with ethyl acetate (2×100 mL), wash with saturated NaCl, then dry over anhydrous magnesium sulfate. Remove the solvent in vacuo to give (1H-Indol-3-ylmethyl)-dimethylamine.

Dissolve a mixture of the (1H-Indol-3-ylmethyl)-dimethylamine (3.54 mmol), sodium cyanide (0.500 g, 10.62 mmol), and ethyl acetate (1.7 mL, 17.7 mmol) in dry dimethyl sulfoxide (12 mL) and heat to 80° C. under nitrogen for 3 h. Cool the reaction mixture to room temperature, dilute with ethyl acetate (150 mL), and wash with water (50 mL), Dry the organic layer over anhydrous magnesium sulfate, and remove the solvent in vacuo to yield (1H-indol-3-yl)-acetonitrile 0.850 g (96%).

Dissolve (1H-indol-3-yl)acetonitrile (3.40 mmol) in dry dimethyl sulfoxide (3.0 mL), cool in an ice bath, combine with anhydrous potassium carbonate (0.200 g) and 30% hydrogen peroxide (0.6 mL), keeping the reaction temperature below 20° C. Warm to room temperature, add water (10 mL) and filter the resulting solid, dry under vacuum.

MS (ES, m/z): 257.3(M+−1).

PREPARATION 85

2-(Imidazo[1,2-a]pyridin-3-yl)acetamide a) Imidazo[1,2-a]pyridin-3-ylacetic acid ethyl ester Add ethyl(E)oxybutenoate (14.3 g, 111.66 mmol) to 2-amino pyridine (10.0 g, 106.4 mmol) in acetonitrile (270 ml). Heat the reaction at 80° C. for 6 hours. Concentrate the reaction mixture under reduced pressure. Purification of the resulting oil by flash chromatography and eluting with a gradient from 100% hexane to 95% ethyl acetate:methanol gives the title compound, Imidazo[1,2-a]pyridin-3-ylacetic acid ethyl ester (10.95 g, 50.0%—determined by NMR) and 2-aminopyridine (co-elution), as a brown solid. 1H NMR (400 MHz, DMSO-d$_6$) 83 (m, 1H), 7.53 (m, 1H), 7.46 (s, 1H), 6.9 (m, 1H), 6.42 (m, 1H), 4.1 (q, J=7 Hz, 211), 1.15 (t, J=7 Hz, 3H).

b) 2-(Imidazo[1,2-a]pyridin-3-yl)acetamide

Bubble ammonia through a solution of (Imidazo[1,2-a]pyridin-3-yl)acetic acid ethyl ester (10.0 g, 48.96 mmol) in methanol (30 ml) at 0° C. Heat the reaction mixture in a sealed tube at 100° C. for 2 hours. Concentrate the reaction mixture under reduced pressure. Tituration in ethyl acetate to gives the title compound (5.0 g, 58.2%), as a white solid. ESMS ($M^++1$): 176.1 m/z.

PREPARATION 86

(R)-2-[5-(1-Benzylpyrrolidin-3-yloxy)benzofur-7-yl] acetamidea) (R)-2-[5-(1-Benzylpyrrolidin-3-yloxy) benzofur-7-yl]acetamide Add to dry ammonium chloride (0.26 g, 4.87 mmol) in anhydrous toluene (3 mL) at −5 to −10° C. a solution of 2.0 M trimethylaluminum in toluene (2.4 mL) and allow the mixture to warm to ambient temperature. When the reaction mixture becomes clear, add (R)-[5-(1-Benzylpyrrolidin-3-yloxy)benzofur-7-yl]acetic acid ethyl ester (0.51 g, 1.34 mmol) in toluene (6 mL) and heat to 50° C. for 3 h. Pour the reaction mixture into a mixture of concentrated hydrochloric acid (1 mL) and water (3 mL), made basic with 5 N sodium hydroxide solution and extract with ethyl acetate. Wash the organic extracts with water, brine, dried and evaporate to dryness to yield the product (0.42 g, 90%), which is used without further purification.

b) 2-[4-(2-Hydroxyethoxy)benzofur-7-yl]acetamide

Add to a solution of 2-{4-[2-(tetrahydropyran-2-yloxy]benzofur-7-yl}acetamide (0.216 g, 0.676 mmol) in methyl alcohol (7 ml) p-toluenesulfonic acid mono-hydrate (catalytic amount), and stir the mixture for 1 hour. Dilute the mixture with ethyl acetate, wash with 1N aqueous sodium bicarbonate, water, and brine, dry over sodium sulfate, filter, and concentrate to give 0.05 g (31%) of the title compound as a off-white solid. Mass Spectrum: electrospray (e/z) 236 ($M^+$+1).

PREPARATION 87

2-[1-(1-Benzylpiperidin-4-yl)-1H-indol-3-yl]-2-hydroxyacetamide

Dissolve [1-(1-benzylpiperidin-4-yl)-1H-indol-3-yl]oxoacetic acid methyl ester (1.29 g, 3.43 mmol) in 2 M ammonia: methanol (35 mL) and stir at room temperature under nitrogen for 1.5 hours. Concentrate to a white solid and slurry into absolute ethanol (40 mL). Add sodium borohydride (0.65 g, 5 equiv) and stir 3 hours at room temperature under nitrogen. Concentrate then dilute with ethyl acetate and quench with water. Wash organic layer with brine. Dry over magnesium sulfate, filter and concentrate to give crude product (1.28 g, 103%). MS (ES, m/z): 364.2 (M+1).

Synthetic Transformation of Intermediates:

O-Alkylations:

PREPARATION 88

5-(2-(tert-butoxy)ethoxy)-1H-indole

Add triphenylphosphine (600 mg, 2.29 mmol) to a solution of diethyl azodicarboxylate (0.36 mL, 2.29 mmol) in methylene chloride (10 ml) at 0° C. followed by ethylene glycol mono-t-butyl ether (0.30 mL, 2.29 mmol), and stir the mixture for 20 minutes at 0° C. Add 5-hydroxyindole (200 mg, 1.5 mmol), remove the cold bath, and stir for 5 hours. Add water (2 mL), transfer the resultant mixture to a separatory funnel, and separate the layers. Wash the organic layer with 0.1 N aqueous HCl and brine, then dry over sodium sulfate, filter, and concentrate. Purification by flash chromatography and eluting with hexane:ethyl acetate gives 127 mg (36%) of the title compound as a light yellow solid. Mass spectrum: electrospray (m/z) 232 ($M^-$−1).

Using similar methods as above the following compounds may be prepared and isolated:

| PREP. # | Product | Physical Data |
|---|---|---|
| 89 | 4-(1H-Indol-5-yloxymethyl)-piperidine-1-carboxylic acid tert-butyl ester | MS(ES, m/z): 329.3(M−1). |
| 90 | 4-(7-cyanomethylbenzofur-5-yloxy)piperidine-1-carboxylic acid tert-butyl ester) | MS(ES, m/z): 301.1(product minus t-Bu), 257.0(product minus -Boc)(M+1) |
| 91 | [5-(1-benzylpiperidin-4-yloxy)benzofur-7-yl]acetonitrile | MS(ES, m/z): 347.1(M+1) |
| 92 | (R)-[5-(1-Benzylpyrrolidin-3-yloxy)benzofur-7-yl]acetic acid ethyl ester | ESMS m/z(relative intensity) 380.2(M++H+, 100) |

PREPARATION 93

4-Bromo-1-[3-(tert-butyldimethylsilyloxy)propyl]-1H-indole

Add sodium hydride (4.89 g, 122.4 mmol, 60% dispersion in mineral oil) to a solution of 4-Bromo-1H-indole (12 g, 61.2 mmol) in dimethylformamide (100 ml). Cool the reaction to 0° C. and add (2-bromoethoxy)-tert-butyldimethylsilane (17.04 g, 67.32 mmol). Stir the reaction for 1 hour at room temperature, quench with aqueous saturated sodium bicarbonate, and extract into ethyl acetate. Combine the organic layers and wash with saturated aqueous sodium chloride, dry over magnesium sulfate. Concentrate under reduced pressure to obtain the title compound, (22.45 g, 100%), as a clear oil. 1H NMR (400 MHz, DMSO-d6) 7.48 (d, J=8, 1H), 7.4 (d, J=3 Hz, 1H), 7.22 (d, J=8 Hz, 1H), 7.05 (dd, J=8, 1 Hz, 1H), 6.4 (d, J=3 Hz, 1H), 4.25 (t, J=7 Hz, 2H), 3.49 (t, J=7 Hz, 2H), 1.9 (quintuplet, 2H), 0.82 (s, 9H), 0.0 (s, 6H).

Using the method above, the following compounds may be prepared and isolated.

| PREP. # | Product | Physical Data |
|---|---|---|
| 94 | 4-Bromo-1-[3-(tert-butyldimethyl-silyloxy)propyl]-1H-indole | 1H NMR(400MHz, DMSO-d6) 7.48(d, J=8, 1H), 7.4(d, J=3Hz, 1H), 7.22(d, J=8Hz, 1H), 7.05(dd, J=8, 1Hz, 1H), 6.4(d, J=3Hz, 1H), 4.25(t, J=7Hz, 2H), 3.49(t, J=7Hz, 2H), 1.9(quintuplet, 2H), 0.82(s, 9H), 0.0(s, 6H) |
| 95 | 4-Bromo-1-methyl-1H-indole | 1H NMR(400MHz, CDCl3) 7.29-7.25(m, 2H), 7.10(d, J=3.2Hz, 1H), 7.07(d, J=8Hz, 1H), 6.53(d, J=2.4Hz, 1H), 3.79(s, 3H) |
| 96 | 1-[2-(tert-Butyldimethylsilyloxy)-ethyl]-6-methoxy-1H-indole | HRMS($M^+$+1): 306.1882 |
| 97 | 5-(2-tert-butoxyethoxy)-N-methylindole | MS(ES, m/z) 248($M^+$+1) |
| 98 | 1-(1-Hydroxybutyl)indole-3-acetamide | MS(FD) m/z(M+1) 247(100%). Anal. Calc'd for $C_{14}H_{18}N_2O_2$ C, 68.27, H, 7.37, N, 11.37. Found 68.29, H, 7.52, N, 11.49. |
| 99 | 1-(1-Hydroxypropyl)indole-3-acetamide | HRMS Calcd 233.1290. Found 233.1291 |
| 100 | 5-[3-(tert-Butyldimethylsilyloxy)-propoxy]-1H-indole | MS(ES, m/z): 306.3(M+1), 304.2(M−1) |
| 101 | 5-[4-(tert-Butyldimethylsilyloxy)-butoxy]-1H-indole | |
| 102 | 7-[3-(tert-Butyldimethylsilyloxy)-propyl]-2,3-dihydro-1H-indole | MS(ES, m/z): 292.2(M+1) |

-continued

| PREP. # | Product | Physical Data |
|---|---|---|
| 103 | 7-bromo-5-(tetrahydropyran-2-yloxy)benzofuran | $^1$H NMR(400MHz, CDCl3) δ 1.70(m, 6H), 3.57(m, 1H), 3.86(m, 1H), 5.31(t, J=3.17Hz, 1H), 6.69(d, J=2.20Hz, 1H), 7.19(m, 2H), 7.58(d, J=2.20Hz, 1H) |
| 104 | 5-Benzyloxy-7-bromobenzofuran | |
| 105 | {4-[3-(tert-Butyldimethylsilyloxy)-propoxy]benzofur-7-yl}acetonitrile | |

Alcohol Conversion to a Bromide:

PREPARATION 106

3-[1-(4-bromobutyl)-1H-indol-3-yl]-4-(4-methoxybenzofur-7-yl)pyrrole-2,5-dione Dissolve 3-[1-(4-hydroxybutyl)-1H-indol-3-yl]-4-(4-methoxybenzofur-7-yl)pyrrole-2,5-dione (0.1 g, 0.232 mmol) in 10 mL dichloromethane. Add carbon tetrabromide (0.077 g, 1 equivalent) and triphenyl phosphine (0.061 g, 1 equivalent). Stir for 10 min, add another equivalent of both reagents. Stir 10 min then dilute with dichloromethane and wash with water followed by brine. Dry over magnesium sulfate then filter and concentrate. Purification by column chromatography (2% methanol: dichloromethane) affords the title compound. MS (ES, m/z): 493.0 (M−1).

The following compounds are prepared in a similar manner:

| PREP. # | Product | Physical Data |
|---|---|---|
| 107 | 3-[4-(3-Bromopropoxy)benzofur-7-yl]-4-(5,6-dihydro-4H-pyrrolo[3,2,1-ij]quinolin-1-yl)pyrrole-2,5-dione | ES(M+1) 505.1 |
| 108 | 3-(Benzofur-7-yl)-4-[7-(3-bromopropyl)-1H-indol-3-yl]pyrrole-2,5-dione | ES(M+1) 451.1 |
| 109 | 3-(Benzofur-7-yl)-4-[7-(3-bromopropyl)-1-methyl-1H-indol-3-yl]pyrrole-2,5-dione | ES(M+1) 463.1 |
| 110 | 3-(4-Methoxybenzofur-7-yl)-4-[1-(4-bromobutyl)-1H-indol-3-yl]pyrrole-2,5-dione | ES(M−1) 493.0 |
| 111 | 3-(5-Methoxybenzofur-7-yl)-4-[1-(3-bromopropyl)-1H-indol-3-yl]pyrrole-2,5-dione | |
| 112 | 3-(5-Methoxybenzofur-7-yl)-4-[1-(2-bromoethyl)-1H-indol-3-yl]pyrrole-2,5-dione | ES(M−1) 464.9 |
| 113 | 3-(Benzofur-7-yl)-4-[5-(3-bromopropoxy)-1-isopropyl-1H-indol-3-yl]pyrrole-2,5-dione | ES(M+1) 509.0 |
| 114 | 3-(Benzofur-7-yl)-4-[7-(3-bromopropyl)-1-isopropyl-1H-indol-3-yl]pyrrole-2,5-dione | ES(M+1) 493.1 |
| 115 | 3-(Benzofur-7-yl)-4-[5-(4-bromobutoxy)-1-isopropyl-1H-indol-3-yl]pyrrole-2,5-dione | ES(M+1) 523.1 |
| 116 | 3-(5-Fluorobenzofur-7-yl)-4-[5-(4-bromobutoxy)-1-isopropyl-1H-indol-3-yl]pyrrole-2,5-dione | ES(M+1) 541.1 |
| 117 | 3-(5,6-Difluorobenzofur-7-yl)-4-[5-(4-bromobutoxy)-1-isopropyl-1H-indol-3-yl]pyrrole-2,5-dione | ES(M+1) 559.1 |
| 118 | 3-(6-fluorobenzofur-7-yl)-4-[5-(4-bromobutoxy)-1-isopropyl-1H-indol-3-yl]pyrrole-2,5-dione | ES(M+1) 541.1 |
| 119 | 3-(Imidazo[1,2-a]pyridin-3-yl)-4-[5-(3-bromopropoxy)-1-isopropyl-1H-indol-3-yl]pyrrole-2,5-dione | |
| 120 | 3-(Benzofur-7-yl)-4-[5-(2-bromoethoxy)-1-methyl-1H-indole-3-yl]pyrrole-2,5-dione | ES(M+1) 465 |
| 121 | 2-[4-(2-Bromoethoxy)benzofur-7-yl]acetamide | ES 296 (M$^+$−1) |

Reactive Amination:

PREPARATION 122

1-(1-Benzylpiperidin-4-lyl)-7-methyl-1H-indole

Dissolve 2-(2,2-dimethoxyethyl)-6-methylphenylamine (0.95 g, 4.9 mmol) in acetic acid (20 mL) and add 1-benzylpiperidin-4-one (1 mL, 1.1 eq). Stir for 5 minutes then add sodium triacetoxyborohydride (1.55 g, 1.5 eq) and stir at room temperature for 45 minutes. Attach a reflux condenser and heat to reflux for 2.5 hours. Let cool to room temperature then dilute with ethyl acetate. Wash with 5 N sodium hydroxide followed by brine. Dry over magnesium sulfate, filter and concentrate. Purification by column chromatography (1:1 hexanes:ethyl acetate) affords 1.26 g product (85%) as a clear oil. MS (ES, m/z): 305.2 (M+1).

Using a similar method the following compounds may be prepared:

| PREP. # | Product | Physical Data |
|---|---|---|
| 123 | 1-(2,2,6,6-Tetramethylpiperidin-4-yl)-1H-indole | ES(M + 1)257.2 |
| 124 | 1-(1-Benzylpiperidin-3-yl)-1H-indole | ES(M + 1): 291.0 |
| 125 | 1-(tert-butoxycarbonyl)-2-methyl-4-indol-1-yl)piperidine | ES(M + 1): 259.1 |
| 126 | 4-(6-Chloro-2,3-dihydroindol-1-yl)piperidine-1-carboxylic acid tert-butyl ester | MS (ES, m/z): 281.1 |
| 127 | 1-(tert-butoxycarbonyl)-4-(5-Chloro-2,3-dihydroindol-1-yl)piperidine | ES(M + 1)281.1 |
| 128 | 1-(tert-butoxycarbonyl)-4-(5-Methyl-2,3-dihydroindol-1-yl)piperidine | ES(M + 1)317.2 |
| 129 | 1-(tert-butoxycarbonyl)-4-(6-Methyl-2,3-dihydroindol-1-yl)piperidine | ES(M + 1)317.2 |
| 130 | 1-(tert-butoxycarbonyl)-4-(5-Chloro-2,3-dihydroindol-1-yl)-2-methylpiperidine | ES(M + 1)295.1 |
| 131 | 1-(tert-butoxycarbonyl)-4-(5-Trifluoromethyl-2,3-dihydroindol-1-yl)piperidine | ES(M + 1)315.1 |
| 132 | 1-(tert-butoxycarbonyl)-4-(2,3-Dihydroindol-1-yl)-3-methylpiperidine | ES(M + 1): 403.2 |

-continued

| PREP. # | Product | Physical Data |
|---|---|---|
| 133 | 3-(6-Fluorobenzofur-7-yl)-4-[1-(1-isopropylpiperidin-4-yl)-1H-indol-3-yl]pyrrole-2,5-dione | ES(M + 1): 472.2 |

N-Alkylation:

PREPARATION 134

5-[3-(tert-Butyldimethylsilyloxy)propoxy]-1-isopropyl-1H-indole

Dissolve 5-[3-(tert-butyldimethylsilyloxy)propoxy]-1H-indole (1.0 g, 0.327 mmol) in N,N-dimethylformamide (20 mL) under nitrogen. Add 3.6 mL potassium tert-butoxide (1M solution in THF, 1.1 equiv) and stir 10 minutes, then add 2-iodopropane (0.36 mL, 1.1 eq) and stir for 30 minutes. Dilute with ethyl acetate and wash with water then brine. Dry over magnesium sulfate, filter and concentrate. Purification by column chromography (hexanes to 4:1 hexanes:ethyl acetate) affords 0.43 g product (38%) as a clear oil. $^1$H NMR (400 MHz, DMSO-$d_6$) δ 0.00 (s, 6H), 0.83 (s, 9H), 1.40 (d, J=6.83 Hz, 6H), 1.86 (m, 2H), 3.74 (m, 2H), 3.98 (m, 2H), 4.64 (m, 1H), 6.29 (d, J=2.93 Hz, 1H), 6.71 (m, 1H), 6.99 (d, J=1.95 Hz, 1H), 7.36 (m, 2H).

Using a similar method the following compounds may be made:

| PREP. # | Product | Data |
|---|---|---|
| 135 | 7-[3-(tert-Butyldimethylsilyloxy)propyl]-1-isopropyl-2,3-dihydro-1H-indole | MS(ES, m/z): 334.3(M + 1) |
| 136 | 1-(acetoxypropyl)-3-indolyl acetonitrile | |
| 137 | 2-{1-[3-(tert-Butyldimethylsilyloxy)propyl]-1H-indol-3-yl}acetamide | HRMS(ES+): 347.2155. |
| 138 | 2-(1-Isopropyl-1H-indol-3-yl)acetamide | |
| 139 | 2-[1-(2-hydroxyethyl)-1H-indol-3-yl]acetamide | MS(ES, m/z): 218.9(M + 1) |
| 140 | (4-Fluoro-1-isopropyl-1H-indol-3-yl)oxoacetic acid methyl ester | MS(ES, m/z) 264(M$^+$ + 1) |
| 141 | (1-Ethyl-4-fluoro-1H-indol-3-yl)oxoacetic acid methyl ester | MS(ES, m/z) 250(M$^+$ + 1) |

Reduction of Indoles to Indolines:

PREPARATION 142

6-Chloro-2,3-dihydro-1H-indole

Dissolve 6-chloro-1H-indole (2 g, 0.013 mol) in acetic acid (10 mL) under nitrogen. Add sodium cyanoborohydride (1.24 g, 1.5 eq) and stir 20 minutes at room temperature. Dilute with ethyl acetate and extract with sodium hydroxide (5 N aqueous). Dry over magnesium sulfate, filter and concentrate to give 2.35 g (116%) crude product. MS (ES, m/z): 154.0 (M+1).

Using a similar method the following compounds may be made:

| PREP. # | Product | Physical Data |
|---|---|---|
| 143 | 5-Chloro-2,3-dihydro-1H-indole | ES(M + 1)154.1 |
| 144 | 5-Methyl-2,3-dihydro-1H-indole | ES(M + 1)134.1 |
| 145 | 6-Methyl-2,3-dihydro-1H-indole | ES(M + 1)134.1 |
| 146 | 5-Trifluoromethyl-2,3-dihydro-1H-indole | ES(M + 1)188.0 |
| 147 | 3-(2,3-Dihydro-1H-indol-7-yl)propan-1-ol | MS(ES, m/z): 178.1(M + 1) |

Oxidation of Indolines to Indoles:

PREPARATION 148

4-(6-Chloroindol-1-yl)piperidine-1-carboxylic acid tert-butyl ester

Dissolve 4-(6-chloro-2,3-dihydroindol-1-yl)-piperidine-1-carboxylic acid tert-butyl ester (3.1 g, 9.2 mmol) in tetrahydrofuran (50 mL) and cool to 0° C. under nitrogen. Dissolve DDQ (2.1 g, 1 eq) in tetrahydrofuran (25 mL) and add dropwise to the reaction over 15 minutes. Stir for 30 minutes at 0° C. Dilute with ethyl acetate then wash with saturated sodium bicarbonate followed by brine. Dry over magnesium sulfate, filter and concentrate to give 3.15 g (102%) crude product. MS (ES, m/z): 279.1 (M+1, product—tert butyl).

Using a similar method described above, the following compounds may be made:

| PREP. # | Product | Physical Data |
|---|---|---|
| 149 | 4-(5-Chloroindol-1-yl)piperidine-1-carboxylic acid tert-butyl ester | ES(M + 1) 335.1 |
| 150 | 4-(5-Methylindol-1-yl)piperidine-1-carboxylic acid tert-butyl ester | ES(M + 1) 259.1 |
| 151 | 4-(6-Methylindol-1-yl)piperidine-1-carboxylic acid tert-butyl ester | ES(M + 1) 259.1 |
| 152 | 4-(5-Chloroindol-1-yl)-2-methylpiperidine-1-carboxylic acid tert-butyl ester | |
| 153 | 4-(5-Trifluoromethylindol-1-yl)piperidine-1-carboxylic acid tert-butyl ester | ES(M + 1) 313.1 |
| 154 | Cis 4-Indol-1-yl-3-methylpiperidine-1-carboxylic acid tert-butyl ester | ES(M + 1) 403.1 |
| 155 | 7-[3-(tert-Butyldimethylsilyloxy)propyl]-1-isopropyl-1H-indole | MS(ES, m/z): 332.3(M + 1) |

General Transformations:

PREPARATION 156

(5-hydroxybenzofur-7-yl)acetic acid ethyl ester

Dissolve 5-methoxybenzofur-7-yl)acetic acid ethyl ester (0.20 g, 0.86 mmol) in methylene chloride (10 mL) at −78° C., add boron tribromide (1.08 g, 0.41 mL, 4.3 mmol) and allow to warm to ambient temperature. After 3 h, pour the reaction mixture onto a mixture of ice and water and extract with methylene chloride. Wash the organic extracts with water, brine, dry over sodium sulphate, filter and evaporate to dryness to yield the product (188 mg, quant). ESMS m/z (relative intensity) 221.0 ($M^+$+H+85).

PREPARATION 157

2-[1-(1-Benzylpiperidin-4-yl)-1H-indol-3-yl]acetamide

Dissolve trimethylsilyl chloride (2.1 mL, 6 eq) and sodium iodide (2.5 g, 6 eq) in acetronitrile (15 mL) and cool to 0° C. while under nitrogen. Dissolve 2-[1-(1-benzylpiperidin-4-yl)-1H-indol-3-yl]-2-hydroxyacetamide (1.0 g, 2.75 mmol) in acetonitrile (10 mL) and add dropwise to the reaction. Let stir overnight and gradually warm to room temperature. Extract with 5% $NaHSO_3$ against ethyl acetate then wash with brine. Basify aqueous layer with saturated sodium bicarbonate and wash with ethyl acetate once more. Combine organic layers and dry over magnesium sulfate. Filter and concentrate. Triturate from hot diethyl ether to afford product (0.64 g, 67%) as a white solid. MS (ES, m/z): 348.0 (M+1).

PREPARATION 158

2-[4-(2-Diethylaminoethoxy)benzofur-7-yl]acetamide

Combine 2-[4-(2-Bromoethoxy)benzofur-7-yl]acetamide (0.102 g, 0.342 mmol) with neat diethyl amine (3 ml, excess), and heat at 55° C. for 18 hours. Dilute the mixture with ethyl acetate and wash with water and brine. Dry over sodium sulfate, filter, and concentrate to give 0.098 g (99%) of the title compound as a brown solid. Mass spectrum: electrospray (m/z) 264 ($M^+$+1).

PREPARATION 159

3-(5-Benzyloxybenzofur-7-yl)-4-[1-(3-pyrrolidin-1-ylpropyl)-1H-indol-3-yl]pyrrole-2,5-dione Dissolve methanesulfonic acid 3-{3-[4-(5-benzyloxybenzofur-7-yl)-2,5-dioxo-2,5-dihydro-1H-pyrrol-3-yl]indol-1-yl}propyl ester (220 mg, 0.39 mmol) and pyrrolidine (411 mg, 5.78 mmol) in 1-methylpyrrolidine (6 ml) and heat to 55° C. for 5 hours. Allow the reaction to cool to room temperature and stir overnight. Dilute the reaction in ethyl acetate, wash with water and brine, and dry with magnesium sulfate. Purification by flash chromatography gives the title compound (200 mg, 95%). MS($ES^+$): 546.13.

PREPARATION 160

3-(Benzofur-7-yl-4-[1-(1,4-doxa-spiro[4.5]dec-8-yl)-4-fluoro-1H-indol-3-yl]pyrrole-2,5-dione Dissolve 2-(benzofur-7-yl)acetamide (632 mg, 3.61 mmol) in anhydrous dimethylformamide (DMF) (7.0 mL) and stir under nitrogen. Add [1-(1,4-Dioxa-spiro[4.5]dec-8-yl)-4-fluoro-1H-indol-3-yl]oxoacetic acid methyl ester (1.56 g, 4.33 mmol) in one portion as a solid. After the mixture becomes homogenous, add potassium tert-butoxide in tetrahydrofuran (i) (1.0 M, 14.4 mL) in one portion (bolus addition). Warm the reaction to 60° C., and the reaction turns a deep red. Heat the reaction at 60° C. for 1 h, allow to cool to room temperature. The reaction is monitored by HPLC and TLC, dilute with 200 mL ethyl acetate, wash with saturated sodium bicarbonate solution (1×100 mL), water (1×50 mL), and brine (1×50 mL), dry over anhydrous magnesium sulfate. Remove the ethyl acetate by rotovap, and the concentrate. Purify by using flash column chromatography (ethyl acetate/ hexanes) to yield 1.49 g (85%) of the title compound. MS (ES, m/z): 487.12 ($M^+$+1), 485.08($M^+$−1).

The following compounds are prepared in a similar manner:

| PREP. # | Product | Physical Data |
|---|---|---|
| 161 | (R)-3-[5-(1-Benzylpyrrolidin-3-yloxy)benzofur-7-yl]-4-(1-methyl-1H-indol-3-yl)pyrrole-2,5-dione | |
| 162 | 3-(5-Benzyloxybenzofur-7-yl)-4-[1-(3-hydroxypropyl)-1H-indol-3-yl]pyrrole-2,5-dione | HRMS(ES+): 493.22 |

PREPARATION 163

3-(benzofur-7-yl)-4-{1-[1-[N-(tert-butoxycarbonyl)alanyl]piperidin-4-yl]indol-3-yl}pyrrole-2,5-dione Dissolve the hydrochloride salt of 3-(benzofur-7-yl)-4-(1-piperidin-4-yl-1H-indol-3-yl)pyrrole-2,5-dione (0.179 g, 0.36 mmol) in 7.2 mL N,N-dimethylformamide under nitrogen. Add EDCI (0.104 g, 1.5 equivalents), HOBT (0.073 g, 1.5 equivalents), L-Boc-Ala-OH (0.068 g, 1 equivalent), and triethyl amine (0.15 mL, 3 eq) and stir the reaction at 20° C. for 3 hours. Extract with ethyl acetate, wash with 1N hydrochloric acid, saturated sodium bicarbonate, then brine. Dry over magnesium sulfate, then filter and concentrate to give 0.21 g (100%) the title compound as an orange solid. MS (ES, m/z): 583.1 (M+1), 581.2 (M−1).

Transformation of N-methylpyrrolodiones to Benzofuryl:

PREPARATION 164

3-(trifluoro-methanesulfonic acid benzofur-7-yl ester)-4-[1-methyl-1H-indol-3-yl]-1-methylpyrrole-2,5-dione Add to a stirred solution of 7-[4-(1-methylindol-3-yl)-2,5-dioxo-3-pyrrolin-3-yl]benzo[b]fur-4-yl (trifluoromethyl)sulfonate (400 mg, 0.82 mmol) in anhydrous N,N-dimethylformamide (10 ml), potassium carbonate (420 mg) and then iodomethane (0.2 ml, 3.0 mmol). Heat the reaction to 70° C. for 15 minutes. Diluted with ethyl acetate, wash with water, brine, dry over magnesium sulfate, filter and concentrate to afford the title compound (404 mg, 98%) as a yellow solid. MS($ES^+$): 505.0

PREPARATION 165

3-(trifluoro-methanesulfonic acid benzofur-4-yl ester)-4-[1-methyl-1H-indol-3-yl]pyrrole-2,5-dione Prepare from 7-[4-(1-methylindol-3-yl)-2,5-dioxo-3-pyrrolin-3-yl]benzo[b]fur-4-yl (trifluoromethyl)sulfonate according to the Preparation 164. ES(M+1): 491.1.

PREPARATION 166

3-(5-Methoxybenzofur-7-yl)-1-methyl-4-(1-methyl-1H-indol-3-yl)pyrrole-2,5-dione

Prepare from 3-(5-methoxybenzofur-7-yl)-4-(1-methyl-1H-indol-3-yl)pyrrole-2,5-dione (6.9 g, 18.6 mmol) according to the Preparation 164. HRMS: calculated 387.1345 found 387.1344.

PREPARATION 167

3-[4-(Benzhydrylideneamino)benzofur-7-yl]-1-methyl-4-(1-methyl-1H-indol-3-yl)pyrrole-2,5-dione Heat a mixture of 7-[1-methyl-4-(1-methylindol-3-yl)-2,5-dioxo-3-pyrrolin-3-yl]benzo[b]fur-4-yl (trifluoromethyl)sulfonate (100 mg, 0.2 mmol), benzophenone imine (0.037 ml, 0.22 mmol), tris-(benzylideneacetone)-dipalladium(0)(9 mg, 0.01 mmol), racemic 2,2'-bis(diphenylphosphino)-1,1'-binaphthyl (19 mg, 0.03 mmol), and cesium carbonate (91 mg, 0.28 mmol) in anhydrous toluene (1 ml) to 80° C. for 19 hours under a nitrogen atmosphere. Allow the reaction to cool to room temperature, dilute with diethyl ether, and filter through Celite. Wash the filtrate with water, brine, dry over magnesium sulfate, filter and concentrate. Flash chromatography over silica gel (ethyl acetate: hexanes) affords the title compound as a red oil. MS(ES$^+$): 536.1.

PREPARATION 168

3-[5-(2-hydroxyethoxy)benzofur-7-yl]-1-methyl-4-(1-methyl-1H-indol-3-yl)pyrrole-2,5-dione Add to a mixture of 3-(5-hydroxybenzofur-7-yl)-1-methyl-4-(1-methyl-1H-indol-3-yl)pyrrole-2,5-dione (2.5 g, 6.7 mmol) and potassium carbonate (2.78 g, 20.1 mmol) in N,N-dimethylformamide (40 ml), 2-(2-bromoethoxy)tetrahydropyran (3.04 ml, 20.1 mmol). Heat the mixture to 80° C. under nitrogen atmosphere for overnight. Diluted with ethyl acetate, wash with water, brine, dry over magnesium sulfate, filter and concentrate to red solid. Dissolve the solid in methanol (40 ml), add p-toluenesulfonic acid (3 g), stir for 20 minutes. Diluted with ethyl acetate, wash with water, brine, dry over magnesium sulfate, filter and concentrate to afford the title compound (1.88 g, 67%) as a red solid. HRMS: calculated 417.1450 found 417.1462.

Using the method described above the following compounds are made in a substantially similar manner:

| PREP. # | Product | Physical Data |
|---|---|---|
| 169 | 3-[4-(2-Hydroxyethoxy)benzofur-7-yl]-4-(1-iso-propyl-1H-indol-3-yl)-1-methylpyrrole-2,5-dione | ES(M + 1): 445.3 |

PREPARATION 170

3-[5-(2-bromoethoxy)benzofur-7-yl]-1-methyl-4-(1-methyl-1H-indol-3-yl)pyrrole-2,5-dione Add to a solution of 3-[5-(2-hydroxyethoxy)benzofur-7-yl]-1-methyl-4-(1-methyl-1H-indol-3-yl)pyrrole-2,5-dione (1.87 g, 4.49 mmol) in dichloromethane (30 ml), triphenylphosphine (1.41 g, 5.39 mmol) and carbon tetrabromide (1.79 g, 5.39 mmol). Stir the reaction for 15 minutes under nitrogen atmosphere. Add another 2.2 mmol of triphenylphosphine and 2.2 mmol of carbon tetrabromide and stir for 15 more minutes. Diluted with dichloromethane, wash with water, brine, dry over magnesium sulfate, filter and concentrate. Flash chromatography over silica gel (1% methanol:dichloromethane) affords the title compound as an orange solid. MS(ES+): 479.0, 481.0.

Using the method described above the following compounds may be made in a substantially similar manner:

| PREP. # | Product | Physical Data |
|---|---|---|
| 171 | 3-[4-(2-Bromoethoxy)benzofur-7-yl]-4-(1-isopropyl-1H-indol-3-yl)-1-methylpyrrole-2,5-dione | ES(M$^+$, M$^+$ + 2): 507.2, 509.2 |
| 172 | 3-[4-(3-Bromopropoxy)benzofur-7-yl]-4-(1-isopropyl-1H-indol-3-yl)-1-methylpyrrole-2,5-dione | ES(M+): 521.2 |

PREPARATION 173

3-[5-(2-diethylaminoethoxy)benzofur-7-yl]-1-methyl-4-(1-methyl-1H-indol-3-yl)pyrrole-2,5-dione Add to a solution of 3-[5-(2-bromoethoxy)benzofur-7-yl]-1-methyl-4-(1-methyl-1H-indol-3-yl)pyrrole-2,5-dione (600 mg, 1.25 mmol) in 1-methylpyrrolidine (8 ml), diethylamine (0.65 ml, 6.28 mmol). Stir overnight under nitrogen atmosphere. Heat the reaction to 60° C. for 4 hours. Dilute with ethyl acetate, wash with water, brine, dry over magnesium sulfate, filter and concentrate to red oil. Flash chromatography through SCX column affords the title compound as a red oil. MS(ES$^+$): 472.1; HRMS: calculated 472.2236 found 472.2235.

Using the method described above the following compounds may be made in a substantially similar manner:

| PREP. # | Product | Physical Data |
|---|---|---|
| 174 | 1-Methyl-3-(1-methyl-1H-indol-3-yl)-4-[5-(2-morpholin-4-yl-ethoxy)benzofur-7-yl]pyrrole-2,5-dione | ES(M + 1): 486.1 |
| 175 | 3-[4-(2-Diethylaminoethoxy)benzofur-7-yl]-4-(1-isopropyl-1H-indol-3-yl)-1-methylpyrrole-2,5-dione | ES(M + 1): 500.3 |
| 176 | 3-[4-(3-Diethylaminopropoxy)benzofur-7-yl]-4-(1-isopropyl-1H-indol-3-yl)-1-methylpyrrole-2,5-dione | ES(M + 1): 500.3 |

PREPARATION 177

3-(1-(3-methanesulfonyloxyprop-1-yl)indol-3-yl)-4-(5-benzyloxybenzofur-7-yl)pyrrole-2,5-dione Dissolve 3-(5-Benzyloxybenzofur-7-yl)-4-[1-(3-hydroxypropyl)-1H-indol-3-yl]pyrrole-2,5-dione (380 mg, 0.77 mmol) and triethylamine (0.43 ml, 3.1 mmol) in tetrahydrofuran (15 ml) and cool in an ice bath. Add methanesulfonyl chloride (0.066 ml, 0.85 mmol) dropwise, and stir for four hours. Dilute the reaction in ethyl acetate, wash with water and brine, dry with magnesium sulfate, and concentrate to give the title compound (440 mg, 100%). MS(ES$^+$): 571.14.

PREPARATION 178

3-[5-(2-diethylaminoethoxy)benzofur-7-yl]-4-(1-methyl-1H-indol-3-yl)fur-2,5-dione Heat a mixture of 3-[5-(2-diethylaminoethoxy)benzofur-7-yl]-1-methyl-4-(1-methyl-1H-indol-3-yl)pyrrole-2,5-dione (525 mg, 1.12 mmol) and potassium hydroxide pellets (625 mg, 11.2 mmol) in absolute ethanol (20 ml) to 60° C. for 5 hours. Cool reaction, dilute with ethyl acetate and water, and the separate layers. Acidify the aqueous layer with 1N hydrochloric acid, concentrate to an orange solid. Dissolve the solid in dichloromethane, wash with water, brine, dry over sodium sulfate, filter and concentrate to afford the title compound (500 mg, 98%) as an orange foam. MS(ES+): 491.3.

Using the method described above the following compounds may be made in a substantially similar manner:

| PREP. # | Product | Physical Data |
|---|---|---|
| 179 | 3-(1-Methyl-1H-indol-3-yl)-4-[5-(2-morpholin-4-ylethoxy)benzofur-7-yl]fur-2,5-dione | |
| 180 | 3-[4-(2-Diethylaminoethoxy)benzofur-7-yl]-4-(1-isopropyl-1H-indol-3-yl)fur-2,5-dione | ES(M + 1): 487.3 |
| 181 | 3-[4-(3-Diethylaminopropoxy)benzofur-7-yl]-4-(1-isopropyl-1H-indol-3-yl)fur-2,5-dione | ES(M + 1): 501.3 |

PREPARATION 182

N-{7-[4-(1-Methyl-1H-indol-3-yl)-2,5-dioxo-2,5-dihydrofur-3-yl]benzofur-4-yl}acetamide a) 3-(4-Aminobenzofur-7-yl)-4-(1-methyl-1H-indol-3-yl)fur-2,5-dione Heat a mixture of 7-[1-methyl-4-(1-methylindol-3-yl)-2,5-dioxo-3-pyrrolin-3-yl]benzo[b]fur-4-yl (trifluoromethyl)sulfonate (60 mg, 0.11 mmol) and potassium hydroxide pellets (62 mg, 1.1 mmol) in absolute ethanol (2 ml) to 70° C. for 3 hours. Dilute the reaction with dichloromethane, acidify with 1N hydrochloric acid, wash with water, brine, dry over magnesium sulfate, filter and concentrate to red solid. Dissolve the crude solid in tetrahydrofuran (~5 ml) and add concentrated hydrochloric acid (2 drops). Stir the reaction for 5 minutes, concentrate to oil. Purify by flash chromatography over silica gel affords the title compound (40 mg, 100%) as a dark red solid. MS(ES+): 359.0.

b) N-{7-[4-(1-Methyl-1H-indol-3-yl)-2,5-dioxo-2,5-dihydrofur-3-yl]benzofur-4-yl}acetamide Add to a solution of 3-(4-aminobenzofur-7-yl)-4-(1-methyl-1H-indol-3-yl)fur-2,5-dione (40 mg, 0.11 mmol) in dichloromethane (1 ml), triethylamine (0.046 ml, 0.34 mmol), and then acetyl chloride (0.016 ml, 0.22 mmol). Stir the reaction under nitrogen atmosphere for 10 minutes, dilute with dichloromethane, wash with 1N hydrochloric acid, brine, dry over magnesium sulfate, filter and concentrate to afford the title compound (40 mg, 90%) as a red solid. MS(ES+): 401.0.

PREPARATION 183

10-Oxo-7-aza-spiro[4.5]decane-7-carboxylic acid tert-butyl ester

Dissolve 7-aza-spiro[4.5]decan-10-one (0.43 g, 0.124 mmol) in tetrahydrofuran (40 mL). Add sodium hydrogencarbonate (5 mL, saturated solution) and di-tert-butyldicarbonate (0.50 g, 0.30 mmol), and stir overnight at room temperature. Wash the solution with water and brine, extracting with ethyl acetate (3×25 mL). Dry over magnesium sulfate, filter and concentrate to afford the title compound. ES(M++H):198.

PREPARATION 184

1-(1-tert-Butoxycarbonyl-3-ethyl-piperidin-4-yl)-1H-indole

Dissolve 1H-Indole (10 g, 50.2 mmol) and 2,6-Dimethyl-4-oxo-piperidine-1-carboxylic acid tert-butyl ester (8.62 g, 55.2 mmol) in glacial acetic acid (100 mL), add sodium triacetoxyborohydride (15.96 g, 75.3 mmol) and heat the mixture to 70° C. for 20 h. Cool the reaction mixture in an ice bath and made basic with 5N sodium hydroxide solution. Extract the mixture with methylene chloride, wash with water, brine and dry over sodium sulphate to yield the title compound. Flash chromatography using a gradient of ethyl acetate in hexanes yields the pure product. ESMS m/z (relative intensity) ES(M++H): 329.1.

Using the method described above the following compounds are made in a substantially similar manner:

| PREP. # | Product | Physical Data |
|---|---|---|
| 185 | 10-Indol-1-yl-7-aza-spiro[4.5]decane-7-carboxylic acid tert-butyl ester | |
| 186 | 4-(5-Chloroindol-1-yl)-3,3-dimethylpiperidine-1-carboxylic acid tert-butyl ester | ES(M+ + H): 441.2 |
| 187 | 4-Indol-1-ylpiperidine-1,3-dicarboxylic acid 1-tert-butyl ester 3-ethyl ester | ES(M+ + H): 317.1 |

PREPARATION 188

4-(3-Methoxyoxalylindol-1-yl)-2,6-dimethylpiperidine-1-carboxylic acid tert-butyl ester Dissolve 4-Indol-1-yl-2,6-dimethylpiperidine-1-carboxylic acid tert-butyl ester (0.43 g, 0.124 mmol) in tetrahydrofuran (40 mL). Add 2,6-lutidine (0.43 mL, 3 eq) and cool to 0° C. Add oxalyl chloride dropwise and stir for 1.5 hours then cool to −78° C., add methanol (0.1 mL, 2 eq) and treated with sodium methoxide (25% w/w in methanol, 22.5 mL). Stir for 1 hour then dilute with ethyl acetate and extract with saturated sodium bicarbonate then brine. Dry over magnesium sulfate, filter and concentrate. Purification by column chromatography (4:1 hexanes:ethyl acetate) affords the title compound as the title compound. MS ES(M++H): 415.2.

Using the method described above the following compounds may be made in a substantially similar manner:

| PREP. # | Product | Physical Data |
|---|---|---|
| 189 | 10-(3-Methoxyoxalylindol-1-yl)-7-aza-spiro[4.5]decane-7-carboxylic acid tert-butyl ester | ES(M+ + H): 441.2 |
| 190 | 4-(5-Chloro-3-methoxyoxalylindol-1-yl)-3,3-dimethylpiperidine-1-carboxylic acid tert-butyl ester | ES(M+ + H): 441.2 |
| 191 | 3-Hydroxymethyl-4-(3-methoxyoxalylindol-1-yl)piperidine-1-carboxylic acid tert-butyl ester | ES(M+ + H): 361.1 |

PREPARATION 192

10-Oxo-7-aza-spiro[4.5]decane-7-carboxylic acid tert-butyl ester

Dissolve 7-aza-spiro[4.5]decan-10-one (0.43 g, 0.124 mmol) in tetrahydrofuran (40 mL). Add sodium hydrogencarbonate (5 mL, saturated solution) and di-tert-butyldicarbonate (0.50 g, 0.30 mmol), and stir overnight at room temperature. Wash the solution with water and brine, extracting with ethyl acetate (3×25 mL). Dry over magnesium sulfate, filter and concentrate to afford the title compound. ES(M$^+$+H):198.

PREPARATION 193

4-Chloro-2-(2,2-dimethoxyethyl)-1-nitrobenzene

Slurry (methoxymethyl)triphenylphosphonium chloride (32.3 g, 93.7 mmol) in tetrahydrofuran (350 ml) and cool in an ice-water bath. Add 1.0M KOtBu (94 ml, 94 mmol) in tetrahydrofuran solution to the reaction dropwise via an addition funnel. Stir reaction for one hour, then add 5-chloro-2-nitrobenzaldehyde (14.5 g, 78.1 mmol) dropwise as a solution in 100 ml tetrahydrofuran. Continue to stir in the ice bath for 20 minutes, then let warm to ambient temperature. Quench with 0.1 N HCl, extract with ethyl acetate, wash organics with water and brine. Dry with sodium sulfate, filter, concentrate to a brown oil. Purify by flash chromatography (1% EtOAc:Hexanes) to give a crude mix of three spots. Dissolve the crude oil in methanol (200 ml), cool in an ice bath, add 4N HCl in dioxane (30 ml), stir overnight, warming to ambient temperature. Concentrate to brown oil. Purify by flash chromatography, elute with hexanes to 3% EtOAc:hexanes gradient. Yields the title compound (3.7 g, 15.1 mmol, 19%).

PREPARATION 194

3-Hydroxymethyl-4-indol-1-ylpiperidine-1-carboxylic acid tert-butyl ester

Dissolve 1-(1-tert-Butoxycarbonyl-3-ethyl-piperidin-4-yl)-1H-indole (2.86 g, 7.7 mmol) in TIP (25 ml) and stir at ambient temperature. Add a 1M solution of lithium aluminum hydride in THF (8.5 ml, 8.5 mmol) dropwise via syringe. Stir for two hours, then quench with 0.34 ml water, 0.26 ml 5N sodium hydroxide, and 1.2 ml water. Filter through a pad of Celite®, concentrate to an oil. Purify by flash chromatography to yield the title compound (1.15 g, 45%). ES (M$^+$+1): 275.1

PREPARATION 195

3-(tert-Butyldimethylsilyloxymethyl)-4-indol-1-ylpiperidine-1-carboxylic acid tert-butyl ester Dissolve 3-Hydroxymethyl-4-indol-1-ylpiperidine-1-carboxylic acid tert-butyl ester (1.1 g, 3.3 mmol) in dichloromethane (20 ml). Add imidazole (340 mg, 5.0 mmol) and tert-butyldimethylsilyl chloride (754 mg, 5.0 mmol) and stir at ambient temperature for 72 hours. Dilute with dichloromethane, wash with 1N HCl, water, brine. Dry with sodium sulfate, filter, and concentrate to an oil. Purify by flash chromatography (10% ethyl acetate:hexanes) to yield the title compound (1.48 g, 100%). ES (M$^+$+1): 389.2

PREPARATION 196

{7-[Benzyl-(tert-butoxycarbonyl)aminomethyl]-1-(pyridin-4-yl)-1H-indol-3-ylmethyl}oxoacetic acid methyl ester a) Benzyl-(1H-indol-7-ylmethyl)amine Add benzyl amine (7.5 g, 69.7 mmol), sodium triacetoxyborohydride (20.7 g, 97.5 mmol) and acetic acid (6.0 mL, 104.6 mmol) to a solution of 1H-indole-7-carboxaldehyde (10.1 g, 69.7 mmol) in 1,2-dichloroethane (100 mL). Stir at ambient temperature for 24 hours. Dilute with dichloromethane and wash the organic layer with water. Dry with magnesium sulfate and concentrate. Purify by chromatography (silica gel; ethyl acetate/methanol; 10:0.3 to 10:1) to yield a light yellow solid (13.5 g, 82%). MS (ESI) m/z 237 (M+H)$^+$.

b) Benzyl-(1H-indol-7-ylmethyl)carbamic acid tert-butyl ester

Add triethylamine (24 mL, 172 mmol), di-tert-butyl dicarbonate (12.4 g, 57.2 mmol) and 4-dimethylaminopyridine (0.7 g, 5.7 mmol) to a solution of benzyl-(1H-indol-7-ylmethyl)amine (13.5 g, 57.2 mmol) in dichloromethane. Stir at ambient temperature for 2 hours. Evaporate the solvent and purify the residue by chromatography (silica gel; hexane/ethyl acetate; 1:0 to 1:1) to yield a solid (10.0 g, 52%). MS ESI) m/z 337 (M+H)$^+$.

c) Benzyl-(2,3-dihydro-1H-indol-7-ylmethyl)carbamic acid tert-butyl ester

Add sodium cyanoborohydride (3.0 g, 47.6 mmol) to a solution of benzyl-(1H-indol-7-ylmethyl)carbamic acid tert-butyl ester (10.0 g, 29.8 mmol) in acetic acid. Stir the mixture at ambient temperature for 3 hours. Dilute with ethyl acetate and cool in an ice bath. Wash the mixture with aqueous 3.0 N sodium hydroxide until pH is 8. Dry the organic layer with magnesium sulfate and concentrate. Purify by chromatography (silica gel; hexane/ethyl acetate; 3:1 to 0:1) to afford a solid as the title compound (5.0 g, 50%). MS (ESI) m/z 339 (M+H)$^+$.

d) Benzyl-[1-(pyridinyl)-2,3-dihydro-1H-indol-7-ylmethyl]carbamic acid tert-butyl ester Bubble nitrogen through benzyl-(2,3-dihydro-1H-indol-7-ylmethyl)carbamic acid tert-butyl ester (3.7 g, 10.9 mmol) in 1,4-dioxane (50 mL) in a sealed tube. Mix with 4-bromopyridine hydrochloride (4.3 g, 21.9 mmol), palladium diacetate (0.5 g, 2.18 mmol), 2-(dicyclohexylphosphino)biphenyl (0.76 g, 2.18 mmol) and sodium tert-butoxide (3.1 g, 32.7 mmol). Stir the mixture 110° C. for 16 hours. Cool and filter, then concentrate the filtrate. Purify by chromatography (silica gel; hexane/ethyl acetate; 3:1 to 0:1) to isolate a solid as the title compound (1.5 g, 33%). MS (ESI) m/z 416 (M+H)$^+$.

e) Benzyl-[1-(pyridin-4-yl)-1H-indol-7-ylmethyl] carbamic acid tert-butyl ester

Add active manganese dioxide (0.8 g, 9.0 mmol) to a solution of benzyl-[1-(pyridin-4-yl)-2,3-dihydro-1H-indol-7-ylmethyl]carbamic acid tert-butyl ester (0.39 mg, 0.94 mmol) in toluene. Stir the mixture at 90° C. for 16 hours. Cool and filter, then concentrate the filtrate. Purify by chromatography (silica gel; hexane/ethyl acetate; 3:1 to 0:1) to isolate a solid as the title compound (200 mg, 50%). MS (ESI) m/z 414 (M+H)$^+$.

f) {7-[Benzyl-(tert-butoxycarbonyl)aminomethyl]-1-(pyridin-4-yl)-1H-indol-3-ylmethyl}oxoacetic acid methyl ester Add five drops of dichloromethane to benzyl-[1-(pyridin-4-yl)-1H-indol-7-ylmethyl]carbamic acid tert-butyl ester (700 mg, 1.7 mmol), then cool to −10° C. Add oxalyl chloride (4.0 mL, 46.6 mmol) slowly to the mixture. Stir the mixture at ambient temperature for 4 hours. Dilute with dichloromethane and cool to −78° C. Add triethylamine (16.3 mL, 0.12 mol) and methanol (15 mL) carefully. Wash the organic layer with water, dry with magnesium sulfate, and concentrate. Purify by chromatography (silica gel; hexane/ethyl acetate; 1:1 to 0:1) to isolate a solid as the title product (0.36 mg, 42%). MS (ESI) m/z 500 (M+H)$^+$.

PREPARATION 197

4-(7-Methoxymethoxymethyl-3-methoxyoxalylindol-1-yl)piperidine-1-carboxylic acid tert-butyl ester a) 3-(3,3-Dimethoxypropyl)-2-nitrobenzoic acid methyl ester Beginning with 3-methyl-2-nitrobenzoic acid methyl ester, the title compound is prepared essentially as Preparation 3. ES (M$^+$+1) 270.

b) 4-(7-Hydroxymethylindol-1-yl)piperidine-1-carboxylic acid tert-butyl ester

Hydrogenate 3-(3,3-dimethoxypropyl)-2-nitrobenzoic acid methyl ester (7.8 g, 0.029 mol) in 100 mL of tetrahydrofuran with 0.743 g 5% Pd/C at 60 psi for 24 hours. Filter and concentrate. Dissolve the resulting product in 30 mL of tetrahydrofuran, and add it dropwise to a suspension of lithium aluminum hydride (2.2 g, 0.058 mol) in 100 mL of tetrahydrofuran at 0° C. Allow the reaction to warm to room temperature, and stir for 2 hours. Quench the mixture with saturated Rochelle salt and extract with ethyl acetate. Dry and concentrate. Dissolve the product in in 30 mL of acetic acid and add 4-oxopiperidine-1-carboxylic acid tert-butyl ester (6.3 g, 0.032 mol). After 10 minutes, add sodium cyanoborohydride (9.2 g, 0.032 mol) and stir the mixture for 1 hour. Heat the mixture at 100° C. for 3 hours, cool, and pour into water. Neutralize the solution with potassium carbonate and extract with ethyl acetate. Dry and concentrate. Dissolve the crude mixture in 100 mL of methanol and treat with 20 mL of 1N sodium hydroxide for 3 hours. Remove the methanol in vacuo, and extract the mixture with ethyl acetate. Dry and concentrate. Purify by flash chromatography using 4:1 hexanes/ethyl acetate to give 4.1 g of 4-(7-hydroxymethylindol-1-yl)piperidine-1-carboxylic acid tert-butyl ester. FAB MS 330.

c) 4-(7-Methoxymethoxymethyl-indol-1-yl)piperidine-1-carboxylic acid tert-butyl ester Dissolve 4-(7-hydroxymethylindol-1-yl)piperidine-1-carboxylic acid tert-butyl ester (0.25 g, 0.76 mmol) in 5 mL of tetrahydrofuran and add sodium hydride (36 mg, 1.5 mmol) at room temperature. After 40 minutes, add methoxymethyl chloride (0.11 mL, 1.5 mmol) and stir the mixture for 4 hours. Concentrate the reaction and subject it to flash chromatography using 5:1 hexanes:ethyl acetate to give 0.23 g product. FAB MS 374.

d) 4-(7-Methoxymethoxymethyl-3-methoxyoxalylindol-1-yl)piperidine-1-carboxylic acid tert-butyl ester Dissolve 4-(7-methoxymethoxymethyl-indol-1-yl)-piperidine-1-carboxylic acid tert-butyl ester (0.36 g, 0.96 mmol) in 20 mL of methylene chloride, cool to 0° C. and add oxalyl chloride (0.093 mL, 1.1 mmol). After 1 hour, add 5 mL of methanol and triethyl amine (0.38 g, 4 mmol) and stir overnight. Flash chromatography using 2:1 hexanes:ethyl acetate gives 0.30 g of the title compound.

EXAMPLE 1

3-(1-Methyl-1H-indol-4-yl)-4-[1-(3-hydroxypropyl)-1H-indol-3-yl]pyrrole-2,5-dione Add potassium tert-butoxide (4.1 ml, 4.1 mmol, 1M in tetrahydrofuran) to a suspension of 2-[1-(3-hydroxypropyl)-1H-indol-3-yl]acetamide (0.32 g, 1.38 mmol) and (1-methyl-1H-indol-4-yl)oxoacetic acid methyl ester (0.30 g, 1.38 mmol) in dimethylformamide (10 ml). Stir the reaction at room temperature for 12 hours, quench with 1N HCl, and extract into ethyl acetate. Wash the organic extract with 5% aqueous lithium chloride and saturated aqueous sodium chloride, dry over magnesium sulfate, filter, and concentrate under reduced pressure. Chromatograph on flash silica using a gradient from neat hexanes to 100% ethyl acetate:hexane to obtain the title compound (0.3 g, 54%) as a red solid. ES(M$^+$+1)400.2 ES(M$^-$−1)398.6.

The following compounds may be prepared essentially as described in EXAMPLE 1:

| EXAMPLE # | Product Name | Physical Data |
|---|---|---|
| 2 | 3-(1-Methyl-1H-indol-4-yl)-4-[1-(3-hydroxypropyl)-6-methoxy-1H-indol-3-yl]pyrrole-2,5-dione | ES(M$^+$ + 1) 430.2; ES(M$^-$ − 1) 428.2 |
| 3 | 3-[1-(3-Hydroxypropyl)-1H-indol-4-yl]-4-(1H-indol-3-yl)pyrrole-2,5-dione | ES(M$^+$ + 1) 386.2; ES(M$^-$ − 1) 384.6 |
| 4 | 3-[1-(3-Hydroxypropyl)-1H-indol-4-yl]-4-[1-(3-hydroxypropyl)-1H-indol-3-yl]pyrrole-2,5-dione | ES(M$^+$ + 1) 444.2; ES(M$^-$ − 1) 442.6 |
| 5 | 3-(Imidazo[1,2-a]pyridin-5-yl)-4-[1-(3-hydroxypropyl)-1H-indol-3-yl]pyrrole-2,5-dione hydrochloride | ES(M$^+$ + 1) 387.1; ES(M$^-$ − 1) 385.0 |
| 6 | 3-(Imidazo[1,2-a]pyridin-3-yl)-4-[1-(3-hydroxypropyl)-1H-indol-3-yl]pyrrole-2,5-dione hydrochloride | ES(M$^+$ + 1) 387.2 |
| 7 | 3-(Imidazo[1,2-a]pyridin-3-yl)-4-(1-piperidin-4-yl-1H-indol-3-yl)pyrrole-2,5-dione hydrochloride | ES(M$^+$ + 1) 412.2; ES(M$^-$ − 1) 410.3 |
| 8 | 3-(Benzofur-7-yl)-4-[5-(2-tert-butoxyethoxy)-1-methyl-1H-indole-3-yl]pyrrole-2,5-dione | ES(M$^-$ + 1) 257 |
| 9 | 3-[4-(2-Hydroxyethoxy)benzofur-7-yl]-4-(1H-indol-3-yl)pyrrole-2,5-dione | EI(M$^-$ − 1) 287.2 |

-continued

| EXAMPLE # | Product Name | Physical Data |
|---|---|---|
| 10 | 3-[4-(2-Diethylaminoethoxy)benzofur-7-yl]-4-(4-fluoro-1-isopropyl-1H-indol-3-yl)pyrrole-2,5-dione hydrochloride | ES($M^+$ + 1) 504.3 |
| 11 | 3-[4-(2-Diethylaminoethoxy)benzofur-7-yl]-4-(1-ethyl-4-fluoro-1H-indol-3-yl)pyrrole-2,5-dione hydrochloride | ES($M^+$ + 1) 490.2 |
| 12 | 3-(4-Methoxybenzofur-7-yl)-4-(1-methyl-1H-indol-3-yl)pyrrole-2,5-dione | HRMS (m/z): 373.1188. |
| 13 | 3-(5-Methoxybenzofur-7-yl)-4-(1-ethyl-1H-indol-3-yl)pyrrole-2,5-dione | ES($M^+$ + 1) 387.1 |
| 14 | 3-(5-Methoxybenzofur-7-yl)-4-(1-isopropyl-1H-indol-3-yl)pyrrole-2,5-dione | ES($M^+$ + 1) 401.2 |
| 15 | 3-(Benzofur-7-yl)-4-(2-isopropyl-1H-indol-3-yl)pyrrole-2,5-dione | ES($M^+$ + 1) 371 |
| 16 | 3-(Benzofur-7-yl)-4-(2-cyclopropyl-1H-indol-3-yl)pyrrole-2,5-dione | ES($M^+$ + 1) 369 |
| 17 | 3-(Benzofur-7-yl)-4-(8-hydroxymethyl-6,7,8,9-tetrahydropyrido[1,2-a]indol-10-yl)pyrrole-2,5-dione | MS(ES, m/z) 413.29($M^+$ + 1) |
| 18 | 3-(5-Methoxybenzofur-7-yl)-4-(8-hydroxymethyl-6,7,8,9-tetrahydropyrido[1,2-a]indol-10-yl)pyrrole-2,5-dione | MS(ES, m/z) 443.27($M^+$ + 1) 441.40($M^-$ − 1) |
| 19 | 3-(5-Fluoro-4-propylbenzofur-7-yl)-4-[1-(piperidine-1-carboxylic acid tert-butyl ester)indol-3-yl]pyrrole-2,5-dione | ES($M^+$ + 1) 572.3 |
| 20 | 3-(4-Methoxybenzofur-7-yl)-4-[1-(4-hydroxybutyl)-1H-indol-3-yl]pyrrole-2,5-dione | ES($M^+$ + 1) 431.1 |
| 21 | 3-(Benzofur-7-yl)-4-(1H-indol-3-yl)pyrrole-2,5-dione | ES($M^+$ + 1) 329.1 |
| 22 | 3-(5-Methoxybenzofur-7-yl)-4-[1-(2-hydroxyethyl)-1H-indol-3-yl]pyrrole-2,5-dione | ES($M^+$ + 1) 402.9 |
| 23 | 3-(Benzofur-7-yl)-4-[7-(3-hydroxypropyl)-1H-indol-3-yl]pyrrole-2,5-dione | ES($M^+$ + 1) 387.2 |
| 24 | 3-(Benzofur-7-yl)-4-[7-(3-hydroxypropyl)-1-methyl-1H-indol-3-yl]pyrrole-2,5-dione | ES($M^+$ + 1) 401.2 |
| 25 | 3-(Benzofur-7-yl)-4-[5-(3-hydroxypropoxy)-1-isopropyl-1H-indol-3-yl]pyrrole-2,5-dione | ES($M^+$ + 1) 445.2 |
| 26 | 3-(Benzofur-7-yl)-4-[7-(3-hydroxypropyl)-1-isopropyl-1H-indol-3-yl]pyrrole-2,5-dione | ES($M^+$ + 1) 429.2 |
| 27 | 3-(Benzofur-7-yl)-4-[5-(4-hydroxybutoxy)-1-isopropyl-1H-indol-3-yl]pyrrole-2,5-dione | ES($M^+$ + 1) 459.2 |
| 28 | 3-(5-Fluorobenzofur-7-yl)-4-[5-(4-hydroxybutoxy)-1-isopropyl-1H-indol-3-yl]pyrrole-2,5-dione | ES($M^+$ + 1) 477.2 |
| 29 | 3-(Imidazo[1,2-a]pyridin-3-yl)-4-[5-(3-hydroxypropoxy)-1-isopropyl-1H-indol-3-yl]pyrrole-2,5-dione | ES($M^+$ + 1) 445.1 |
| 30 | 3-(Isoquinolin-5-yl)-4-[1-(3-hydroxypropyl)-1H-indol-3-yl]pyrrole-2,5-dione | ES($M^+$ + 1) 398.1 |
| 31 | 3-(Isoquinolin-5-yl)-4-(5-methoxy-2-methyl-1H-indol-3-yl)pyrrole-2,5-dione | ES($M^+$ + 1) 384.1 |
| 32 | 3-(Isoquinolin-5-yl)-4-[1-(piperidin-4-yl)-1H-indol-3-yl]pyrrole-2,5-dione | ES($M^+$ + 1) 423.4 |
| 33 | 3-(Benzofur-7-yl)-4-{1-[1-(tetrahydropyran-4-carbonyl)piperidin-4-yl]-1H-indol-3-yl}pyrrole-2,5-dione | ES($M^+$ + 1) 524.3 |
| 34 | 3-(Benzofur-7-yl)-4-{1-[1-(tetrahydropyran-4-ylmethyl)piperidin-4-yl]-1H-indol-3-yl}pyrrole-2,5-dione hydrochloride | ES($M^+$ + 1) 510.3 |
| 35 | 3-(Benzofur-7-yl)-4-[1-tetrahydropyran-4-yl)-1H-indol-3-yl]pyrrole-2,5-dione | ESMS m/z: 413.1 ($M^+$ + 1) |
| 36 | 3-(6-Fluorobenzofur-7-yl)-4-[1-(1-benzylpiperidin-3-yl)-1H-indol-3-yl]pyrrole-2,5-dione | HRMS($M^+$ + 1) 520.2036 |
| 37 | 3-(Furo[3,2-c]pyridin-7-yl)-4-[1-(piperidine-1-carboxylic acid tert-butyl ester)indol-3-yl]pyrrole-2,5-dione | ES($M^+$ + 1) 513.2 |
| 38 | 3-(Benzofur-7-yl)-4-{5,6-difluoro-7-[1-(carboxylic acid tert-butyl ester)-2-methylpiperazin-4-yl]-1-methyl-1H-indol-3-yl}pyrrole-2,5-dione | ES($M^+$+ 1) 577.2 |
| 39 | 3-(6-Fluorobenzofur-7-yl)-4-[1-(2,2,6,6-tetramethylpiperidin-4-yl)-1H-indol-3-yl]pyrrole-2,5-dione hydrochloride | ES($M^+$ + 1) 486.2 |
| 40 | 3-(Imidazo[1,2-a]pyridin-3-yl)-4-(1-isopropyl-1H-indol-3-yl)pyrrole-2,5-dione | ES($M^+$ + 1) 371.2 |

| EXAMPLE # | Product Name | Physical Data |
|---|---|---|
| 41 | 3-(Benzofur-7-yl)-4-[4-fluoro-1-(piperidin-4-yl)-1H-indol-3-yl]pyrrole-2,5-dione hydrochloride | ES(M$^+$ + 1) 430.2 |
| 42 | 3-(4-Chlorobenzofur-7-yl)-4-[1-(piperidin-4-yl)-1H-indol-3-yl]pyrrole-2,5-dione | HRMS(M + H) 446.1266 |
| 43 | 3-(5-Fluoro-4-propylbenzofur-7-yl)-4-[1-(piperidin-4-yl)-1H-indol-3-yl]pyrrole-2,5-dione | HRMS(M + H) 472.2034 |
| 44 | 3-(5-Chloro-4-fluorobenzofur-7-yl)-4-[1-(piperidin-4-yl)-1H-indol-3-yl]pyrrole-2,5-dione | HRMS(M + H) 464.1162 |
| 45 | 3-(4-Methylsulfanylbenzofur-7-yl)-4-[1-(piperidin-4-yl)-1H-indol-3-yl]pyrrole-2,5-dione | HRMS(M + H) 458.1552 |
| 46 | 3-(4,6-Difluorobenzofur-7-yl)-4-[1-(piperidin-4-yl)-1H-indol-3-yl]pyrrole-2,5-dione | HRMS(M + H) 448.1482 |
| 47 | 3-(5,6-Difluorobenzofur-7-yl)-4-[1-(piperidin-4-yl)-1H-indol-3-yl]pyrrole-2,5-dione hydrochloride | ESMS(M$^-$ − 1)m/z: 446.3 |
| 48 | 3-(4,5-Difluorobenzofur-7-yl)-4-[1-(piperidin-4-yl)-1H-indol-3-yl]pyrrole-2,5-dione hydrochloride | ESMS(M$^-$ − 1)m/z: 446.3 |
| 49 | 3-(6-Fluorobenzofur-7-yl)-4-[1-(piperidin-4-yl)-1H-indol-3-yl]pyrrole-2,5-dione hydrochloride | ES(M$^+$ + H) 430.0 |
| 50 | 3-(5-Chlorobenzofur-7-yl)-4-[1-(piperidin-4-yl)-1H-indol-3-yl]pyrrole-2,5-dione hydrochloride | ESMS(M$^+$ + H)m/z: 446.1 |
| 51 | 3-(6-Fluorobenzofur-7-yl)-4-[1-(2-methylpiperidin-4-yl)-1H-indol-3yl]pyrrole-2,5-dione hydrochloride | HRMS(M + 1): 444.1723 |
| 52 | 3-(6-Fluorobenzofur-7-yl)-4-[1-(2,6-dimethylpiperidin-4-yl)-1H-indol-3-yl]pyrrole-2,5-dione hydrochloride | ES(M$^+$ + H): 458.2 |
| 53 | 3-(6-Fluoro-2,3-dihydrobenzofour-7-yl)-4-[1-(7-aza-spiro[4.5]dec-10-yl)-1H-indol-3-yl]pyrrole-2,5-dione hydrochloride | ES(M$^+$ + H): 486.2 |
| 54 | 3-(6-Flourobenzofur-7-yl)-4-[1-(7-aza-spiro[4.5]dec-10-yl)-1H-indol-3-yl]pyrrole-2,5-dione hydrochloride | ES(M$^+$ + H): 484.2 |
| 55 | Cis 3-(Imidazo[1,2-a]pyridin-3-yl)-4-[1-(2-methylpiperidin-4-yl)-1H-indol-3-yl]pyrrole-2,5-dione hydrochloride | HRMS(M + 1): 426.1942 |
| 56 | Trans 3-(Imidazo[1,2-a]pyridin-3-yl)-4-[1-(2-methylpiperidin-4-yl)-1H-indol-3-yl]pyrrole-2,5-dione hydrochloride | HRMS(M + 1): 426.1936 |
| 57 | 3-(Imidazo[1,2-a]pyridin-3-yl)-4-[5-chloro-1-(3,3-dimethylpiperidin-4-yl)-1H-indol-3-yl]pyrrole-2,5-dione hydrochloride | HRMS(M + 1): 474.1704 |
| 58 | 3-(6-Fluorobenzofur-7-yl)-4-[5-Chloro-1-(3,3-dimethylpiperidin-4-yl)-1H-indol-3-yl]pyrrole-2,5-dione hydrochloride | ES(M$^+$ + H): 492.1 |
| 59 | 3-(6-Fluoro-2,3-dihydrobenzofur-7-yl)-4-[5-Chloro-1-(3,3-dimethylpiperidin-4-yl)-1H-indol-3-yl]pyrrole-2,5-dione hydrochloride | ES(M$^+$ + H): 494.1 |
| 60 | Cis 3-(6-Fluoro-2,3-dihydrobenzofur-7-yl)-4-[1-(2-methylpiperidin-4-yl)-1H-indol-3-yl]pyrrole-2,5-dione hydrochloride | ES(M$^+$ + H): 446.1 |
| 61 | 3-(6-Fluorobenzofur-7-yl)-4-[1-(3-hydroxymethylpiperidin-4-yl)-1H-indol-3-yl]pyrrole-2,5-dione hydrochloride | ES(M$^+$ + H): 412.2 |
| 62 | 3-(6-Fluorobenzofur-7-yl)-4-[7-(benzylamino-methyl)-1-(pyridin-4-yl)-1H-indol-3-yl]pyrrole-2,5-dione | MS(M + H) 543 |
| 63 | 3-(6-Fluoro-2,3-dihydrobenzofur-7-yl)-4-[7-(benzylaminomethyl)-1-(pyridin-4-yl)-1H-indol-3-yl]pyrrole-2,5-dione | MS(M + H) 545 |
| 64 | 3-(6-Fluoro-2,3-dihydrobenzofur-7-yl)-4-[7-methoxymethoxymethyl-1-(piperidin-4-yl)-1H-indol-3-yl]pyrrole-2,5-dione | MS(M + H) 506 |
| 65 | 3-(6-Fluoro-2,3-dihydrobenzofur-7-yl)-4-[7-hydroxymethyl-1-(piperidin-4-yl)-1H-indol-3-yl]pyrrole-2,5-dione | MS(M + H) 462 |
| 66 | 3-(Imidazo[1,2-a]pyridin-3-yl)-4-((1-(1-tert-butoxycarbonyl)piperidin-4-yl)-6-chloroindol-3-yl)pyrrole-2,5-dione | MS(M + H) 546.2 |

EXAMPLE 67

3-(Benzofur-7-yl)-4-{1-[1-(2-alaninyl)piperidin-4-yl]-1H-indol-3-yl}pyrrole-2,5-dione Dissolve (2-{4-[3-(4-(benzofur-7-yl)-2,5-dioxo-2,5-dihydro-1H-pyrrol-3-yl)indol-1-yl]piperidin-1-yl}-1-methyl-2-oxoethyl)carbamic acid tert-butyl ester (0.21 g, 0.36 mmol) in dichloromethane (30 mL) and add hydrochloric acid in dioxane (4N, 10 mL) while under nitrogen. After 3 hours, dilute with diethyl ether and filter off the orange precipitate to give 0.123 g (66%) of the title compound. High Res. Mass Spec (m/z): Calcd 483.2032 Found 483.2040.

The following compounds may be prepared in a similar manner as EXAMPLE 67:

| Example # | Product Name | Physical Data |
|---|---|---|
| 68 | 3-(Benzofur-7-yl)-4-[1-isopropyl-5-(piperidin-4-ylmethoxy)-1H-indol-3-yl]pyrrole-2,5-dione | ES(M$^+$ + H) 484.2 |
| 69 | 3-(5,6-Difluorobenzofur-7-yl)-4-[1-(2-methylpiperidin-4-yl)-1H-indol-3-yl]pyrrole-2,5-dione hydrochloride | ES(M$^+$ + H): 462.2 |
| 70 | 3-(5,6-Difluorobenzofur-7-yl)-4-[1-(2-methylpiperidin-4-yl)-1H-indol-3-yl]pyrrole-2,5-dione hydrochloride | ES(M$^+$ + H): 462.2 |
| 71 | 3-(6-Fluorobenzofur-7-yl)-4-[1-(3-methylpiperidin-4-yl)-1H-indol-3-yl]pyrrole-2,5-dione | ES(M$^+$ + H): 444.2 |
| 72 | 3-(6-Fluorobenzofur-7-yl)-4-[1-(2-methylpiperidin-4-yl)-1H-indol-3-yl]pyrrole-2,5-dione hydrochloride | ES(M$^+$ + H): 444.2 |
| 73 | 3-(6-Fluorobenzofur-7-yl)-4-[1-(2-methylpiperidin-4-yl)-1H-indol-3-yl]pyrrole-2,5-dione hydrochloride | ES(M$^+$ + H): 444.2 |
| 74 | 3-(Furo[3,2-c]pyridin-7-yl)-4-[1-(piperidin-4-yl)-1H-indol-3-yl]pyrrole-2,5-dione hydrochloride | ES(M$^+$ + H) 413.2 |
| 75 | 3-(Benzofur-7-yl)-4-[5,6-difluoro-1-methyl-7-(3-methylpiperazin-1-yl)-1H-indol-3-yl]pyrrole-2,5-dione hydrochloride | ES(M$^+$ + H) 477.2 |
| 76 | 3-(6-Fluorobenzofur-7-yl)-4-[6-chloro-1-(piperidin-4-yl)-1H-indol-3-yl]pyrrole-2,5-dione hydrochloride | ES(M$^+$ + H) 464.1 |
| 77 | 3-(6-Fluorobenzofur-7-yl)-4-[5-chloro-1-(piperidin-4-yl)-1H-indol-3-yl]pyrrole-2,5-dione hydrochloride | ES(M$^+$ + H) 464.1 |
| 78 | 3-(6-Fluorobenzofur-7-yl)-4-[5-methyl-1-(piperidin-4-yl)-1H-indol-3-yl]pyrrole-2,5-dione hydrochloride | ES(M$^+$ + H) 444.2 |
| 79 | 3-(6-Fluorobenzofur-7-yl)-4-[6-methyl-1-(piperidin-4-yl)-1H-indol-3-yl]pyrrole-2,5-dione hydrochloride | ES(M$^+$ + H) 444.2 |
| 80 | 3-(6-Fluorobenzofur-7-yl)-4-[1-(piperidin-4-yl)-5-trifluoromethyl-1H-indol-3-yl)pyrrole-2,5-dione hydrochloride | HRMS 498.1446 |
| 81 | 3-(6-Fluorobenzofur-7-yl)-4-[5-chloro-1-(2-methylpiperidin-4-yl)-1H-indol-3-yl]pyrrole-2,5-dione hydrochloride | ES(M$^+$ + H) 478.1 |
| 82 | 3-(6-Fluorobenzofur-7-yl)-4-[5-chloro-1-(2-methylpiperidin-4-yl)-1H-indol-3-yl]pyrrole-2,5-dione hydrochloride | ES(M$^+$ + H) 478.1 |
| 83 | 3-(Imidazo[1,2-a]pyridin-3-yl)-4-[5-chloro-1-(piperidin-4-yl)-1H-indol-3-yl]pyrrole-2,5-dione hydrochloride | ES(M$^+$ + H) 446.1 |
| 84 | 3-(2,2-Difluorobenzo[1,3]dioxol-4-yl)-4-[1-(piperidin-4-yl)-1H-indol-3-yl]pyrrole-2,5-dione hydrochloride | ES(M$^+$ + H) 452.1 |
| 85 | 3-(Benzo[1,3]dioxol-4-yl)-4-[1-(piperidin-4-yl)-1H-indol-3-yl]pyrrole-2,5-dione hydrochloride | ES(M$^+$ + H) 416.1 |
| 86 | 3-(6-Fluoro-2,3-dihydrobenzofur-7-yl)-4-[1-(piperidin-4-yl)-1H-indol-3-yl]pyrrole-2,5-dione hydrochloride | ES(M$^+$ + H) 432.1 |
| 87 | 3-(6-Fluorobenzofur-7-yl)-4-[5-methoxy-1-(piperidin-4-yl)-1H-indol-3-yl]pyrrole-2,5-dione hydrochloride | ES(M$^+$ + H) 460.1 |
| 88 | 3-(2,3-Dihydro-6-fluorobenzofur-7-yl)-4-[5-chloro-1-(piperidin-4-yl)-1H-indol-3-yl]pyrrole-2,5-dione hydrochloride | ES(M$^+$ + H) 466.1 |
| 89 | 3-(2,3-Dihydrobenzofur-7-yl)-4-[1-(piperidin-4-yl)-1H-indol-3-yl]pyrrole-2,5-dione hydrochloride | ES(M$^+$ + H) 414.1 |
| 90 | 3-(2,3-Dihydro-6-fluorobenzofur-7-yl)-4-[5-(3-hydroxyprop-1-yl)-1-(isopropyl)-1H-indol-3-yl]pyrrole-2,5-dione hydrochloride | ES(M$^+$ + H) 465.1 |
| 91 | 3-(2,3-Dihydro-5,6-difluorobenzofur-7-yl)-4-[1-(piperidin-4-yl)-1H-indol-3-yl]pyrrole-2,5-dione hydrochloride | ES(M$^+$ + H) 450.1 |
| 92 | 3-(2,3-Dihydro-3-methyl-6-fluorobenzofur-7-yl)-4-[1-(piperidin-4-yl)-1H-indol-3-yl]pyrrole-2,5-dione hydrochloride | ES(M$^+$ + H) 446.1 |
| 93 | 3-(2,3-Dihydro-6-fluorobenzofur-7-yl)-4-[1-(3,3-dimethylpiperidin-4-yl)-1H-indol-3-yl]pyrrole-2,5-dione hydrochloride | ES(M$^+$ + H) 460.1 |
| 94 | 3-(2,3-Dihydro-4-methoxybenzofur-7-yl)-4-[1-(piperidin-4-yl)-1H-indol-3-yl]pyrrole-2,5-dione hydrochloride | ES(M$^+$ + H) 444.1 |

| Example # | Product Name | Physical Data |
|---|---|---|
| 95 | 3-(2,3-Dihydro-4-methoxybenzofur-7-yl)-4-[1-(3,3-dimethylpiperidin-4-yl)-1H-indol-3-yl]pyrrole-2,5-dione hydrochloride | ES(M$^+$ + H) 442.2 |
| 96 | 3-(Furo[3,2-c]pyridin-7-yl)-4-[1-(3,3-dimethyl-piperidin-4-yl)-1H-indol-3-yl]pyrrole-2,5-dione hydrochloride | ES(M$^+$ + H) 441.1 |
| 97 | 3-(2,3-Dihydro-6-fluorobenzofur-7-yl)-4-[1-(piperidin-4-yl)-7-methyl-1H-indol-3-yl]pyrrole-2,5-dione hydrochloride | ES(M$^+$ + H) 446.2 |

EXAMPLE 98

3-(5-Methoxybenzofur-7-yl)-4-[1-(3-dimethylaminopropyl)-1H-indol-3-yl]pyrrole-2,5-dione Dissolve 3-(5-methoxybenzofur-7-yl)-4-[1-(3-hydroxypropyl)-1H-indol-3-yl]pyrrole-2,5-dione (0.058 g, 0.118 mmol) in 10 mL dichloromethane. Add carbon tetrabromide (0.077 g, 1 equivalent) and triphenyl phosphine (0.061 g, 1 equivalent). Stir for 10 min, add another equivalent of both reagents. Stir 10 min then dilute with dichloromethane and wash with water followed by brine. Dry over magnesium sulfate then filter and concentrate. Purification by column chromatography (2% methanol:dichloromethane) affords the 3-(5-methoxybenzofur-7-yl)-4-[1-(3-bromopropyl)-1H-indol-3-yl]pyrrole-2,5-dione. 3-(5-Methoxybenzofur-7-yl)-4-[1-(3-bromopropyl)-1H-indol-3-yl]pyrrole-2,5-dione is dissolved in 1.5 mL 1-methyl-2-pyrrolidinone and add dimethylamine (2M solution in tetrahydrofuran, 0.3 mL, 5 equivalents). Heat to 60° C. for 16 hrs. Extract with ethyl acetate versus water, concentrate organic layer. Redissolve in a minimal amount of methanol and load onto an SCX™ Varian column (pretreated with a 5% acetic acid: methanol solution). Wash with methanol and ethyl acetate to remove impurities, flush with 2M ammonia methanol to recover product. ES(M$^+$+H)444.0.

The following compounds are prepared in similar manner as described above.

| Example # | Product | Physical Data |
|---|---|---|
| 99 | 3-(5-Methoxybenzofur-7-yl)-4-[1-(2-dimethylaminoethyl)-1H-indol-3-yl]pyrrole-2,5-dione | ES(M$^+$ + H) 430.0 |
| 100 | 3-(5-Methoxybenzofur-7-yl)-4-{1-[2-(4-methylpiperazin-1-yl)ethyl]-1H-indol-3-yl}pyrrole-2,5-dione | ES(M$^+$ + H) 485.0 |
| 101 | 3-(Benzofur-7-yl)-4-[7-(3-diethylaminopropyl)-1H-indol-3-yl]pyrrole-2,5-dione | ES(M$^+$ + H) 442.2 |
| 102 | 3-(Benzofur-7-yl)-4-[7-(3-diethylaminopropyl)-1-methyl-1H-indol-3-yl]pyrrole-2,5-dione | ES(M$^+$ + H) 456.3 |
| 103 | 3-(Benzofur-7-yl)-4-[5-(3-diethylaminopropoxy)-1-isopropyl-1H-indol-3-yl]pyrrole-2,5-dione | ES(M$^+$ + H) 500.2 |
| 104 | 3-(Benzofur-7-yl)-4-{1-isopropyl-5-[3-(piperidin-1-yl)propoxy]-1H-indol-3-yl}pyrrole-2,5-dione | ES(M$^+$ + H) 512.3 |
| 105 | 3-(Benzofur-7-yl)-4-{5-[3-(4-hydroxypiperidin-1-yl)propoxy]-1-isopropyl-1H-indol-3-yl}pyrrole-2,5-dione | ES(M$^+$ + H) 528.2 |
| 106 | 3-(Benzofur-7-yl)-4-[5-(4-diethylaminobutoxy)-1-isopropyl-1H-indol-3-yl]pyrrole-2,5-dione | ES(M$^+$ + H) 514.2 |
| 107 | 3-(Benzofur-7-yl)-4-[7-(3-diethylaminopropyl)-1-isopropyl-1H-indol-3-yl]pyrrole-2,5-dione | ES(M$^+$ + H) 484.2 |
| 108 | 3-(5-Fluorobenzofur-7-yl)-4-[5-(4-diethylaminobutoxy)-1-isopropyl-1H-indol-3-yl]pyrrole-2,5-dione | ES(M$^+$ + H) 532.3 |
| 109 | 3-(5,6-Difluorobenzofur-7-yl)-4-[5-(4-diethylaminobutoxy)-1-isopropyl-1H-indol-3-yl]pyrrole-2,5-dione hydrochloride | ES(M$^+$ + H) 550.2 |
| 110 | 3-(6-Fluorobenzofur-7-yl)-4-[5-(4-diethylaminobutoxy)-1-isopropyl-1H-indol-3-yl]pyrrole-2,5-dione hydrochloride | ES(M$^+$ + H) 532.2 |
| 111 | 3-(Imidazo[1,2-a]pyridin-3-yl)-4-[5-(3-diethylaminopropoxy)-1-isopropyl-1H-indol-3-yl]pyrrole-2,5-dione | ES(M$^+$ + H) 500.2 |
| 112 | 3-[4-(3-Dimethylaminopropoxy)benzofur-7-yl]-4-(1-methyl-1H-indol-3-yl)pyrrole-2,5-dione hydrochloride | ESMS (M$^+$ + H)m/z: 444.2 |
| 113 | 3-[5-(2-Morpholin-4-ylethoxy)benzofur-7-yl]-4-(1-methyl-1H-indol-3-yl)pyrrole-2,5-dione hydrochloride | HRMS(M + H) 472.1880 |
| 114 | 3-(5-Fluorobenzofur-7-yl)-4-[5-(3-diethylaminopropoxy)-1-isopropyl-1H-indol-3-yl]pyrrole-2,5-dione hydrochloride | ES(M$^+$ + H) 518.3 |
| 115 | 3-(Furo[3,2-c]pyridin-7-yl)-4-[7-(3-diethylaminopropyl)-1-isopropyl-1H-indol-3-yl]pyrrole-2,5-dione hydrochloride | ES(M$^+$ + H) 485.3 |
| 116 | 3-(Furo[3,2-c]pyridin-7-yl)-4-[5-(3-diethylaminopropoxy)-1-isopropyl-1H-indol-3-yl]pyrrole-2,5-dione hydrochloride | ES(M$^+$ + H) 501.3 |
| 117 | 3-(Benzofur-7-yl)-4-{5-[3-(4-acetylpiperazin-1-yl)propoxy]-1-isopropyl-1H-indol-3-yl}pyrrole-2,5-dione hydrochloride | ES(M$^+$ + H) 555.2 |

-continued

| Example # | Product | Physical Data |
|---|---|---|
| 118 | 3-(4-Methoxybenzofur-7-yl)-4-[1-(3-dimethylaminopropyl)-1H-indol-3-yl]pyrrole-2,5-dione | HRMS(m/z): 458.2078 |
| 119 | 3-(Benzofur-7-yl)-4-{5-[2-(cyclopropylmethylamino)ethoxy]-1-methyl-1H-indol-3-yl}pyrrole-2,5-dione hydrochloride | ES($M^+$ + 1) 456 |
| 120 | 3-(Benzofur-7-yl)-4-[5-(2-ethylaminoethoxy)-1-methyl-1H-indol-3-yl]pyrrole-2,5-dione hydrochloride | ES($M^+$ + 1) 430 |
| 121 | 3-(Benzofur-7-yl)-4-[5-(2-benzylaminoethoxy)-1-methyl-1H-indol-3-yl]pyrrole-2,5-dione hydrochloride | ES($M^+$ + 1) 492 |
| 122 | 3-(Benzofur-7-yl)-4-[5-(2-diethylaminoethoxy)-1-methyl-1H-indol-3-yl]pyrrole-2,5-dione hydrochloride | ES($M^+$ + 1) 458 |
| 123 | 3-(Benzofur-7-yl)-4-[1-methyl-5-(2-piperazin-1-ylethoxy)-1H-indol-3-yl]pyrrole-2,5-dione dihydrochloride | ES($M^+$ + 1) 471 |
| 124 | 3-(5-Fluorobenzofur-7-yl)-4-[7-(3-diethylaminopropyl)-1-isopropyl-1H-indol-3-yl]pyrrole-2,5-dione | ES($M^+$ + H) 502.3 |
| 125 | 3-(5-Hydroxybenzofur-7-yl)-4-[1-(3-pyrrolidin-1-ylpropyl)-1H-indol-3-yl]pyrrole-2,5-dione hydrochloride | HRMS(M + H) 492.1625 |

EXAMPLE 126

3-[5-(carbamic acid methyl ester)benzofur-7-yl]-4-[1-methyl-1H-indol-3-yl]pyrrole-2,5-dione Cool a solution of 3-(5-aminobenzofur-7-yl)-4-(1-methyl-1H-indol-3-yl)furo-2,5-dione (30 mg, 0.084 mmol) in dichloromethane (1 ml) to a −78° C., add triethylamine (0.035 ml, 0.25 mmol) and methyl chloroformate (0.013 ml, 0.17 mmol) dropwise. Stir the reaction for 10 minutes, warm to 20° C. Diluted with ethyl acetate, wash with water, brine, dry over magnesium sulfate, filter and concentrate to an orange solid. Dissolve crude solid in N,N-dimethylformamide (1 ml), methanol (0.1 ml), add 1,1,1,3,3,3-hexamethyl-disilazane (0.2 ml). Heat the reaction to 80° C. for 5 hours, dilute with ethyl acetate, wash with water, 0.1N hydrochloric acid, brine, dry over magnesium sulfate, filter and concentrate to an orange film. Flash chromatography over silica gel (40% ethyl acetate:hexanes) affords the title compound (6 mg) as an orange solid.
HRMS (M+H) 416.1248

EXAMPLE 127

3-(5-(N-methanesulfonamide)benzofur-7-yl)-4-[1-methyl-1H-indol-3-yl]pyrrole-2,5-dione Follow similar procedure as in Example 96, starting with 3-(5-aminobenzofur-7-yl)-4-(1-methyl-1H-indol-3-yl)furo-2,5-dione (20 mg, 0.056 mmol) and methanesulfonyl chloride (0.004 ml, 0.056 mmol). Flash chromatography over silica gel (40% ethyl acetate:hexanes) affords the title compound (8 mg) as an orange solid.
HRMS (M+H) 436.0939.

EXAMPLE 128

3-(6-Fluorobenzofur-7-yl)-4-{1-[1-(2-glycyl)piperidin-4-yl]-1H-indol-3-yl}pyrrole-2,5-dione Combine 3-(6-fluorobenzofur-7-yl)-4-[1-(piperidin-4-yl]-1H-indol-3-yl]pyrrole-2,5-dione (90 mg, 0.22 mmol), tert-butoxycarbonylamino-acetic acid (40 mg, 0.22 mmol), 4-N,N-dimethylaminopyridine (10 mg), triethylamine (0.091 ml, 0.66 mmol) and 1-(3-dimethylaminopropyl)-3-ethylcarbodiimide hydrochloride (63 mg, 0.33 mmol) in dichloromethane (5 ml) and stir at room temperature overnight. Purify the crude reaction mixture by a 10 gram SCX™ Varian column, wash column with methanol, and then wash the product off with 2.0M ammonia in methanol solution. Concentrate the product fractions to a yellow solid, triturate with ether to give the title compound as a yellow solid. HRMS (ES+): 487.1779.

Using the method described in Example 128, the following compounds may be made in a substantially similar manner:

| EXAMPLE # | Product | Physical Data |
|---|---|---|
| 129 | 3-(6-Fluorobenzofur-7-yl)-4-{1-[1-(2-methylamino-acetyl)piperidin-4-yl]-1H-indol-3-yl}pyrrole-2,5-dione | HRMS(M + H) 501.1948 |
| 130 | 3-(Imidazo[1,2-a]pyridin-3-yl)-4-{1-[1-(piperidine-4-carbonyl)piperidin-4-yl]-1H-indol-3-yl}pyrrole-2,5-dione hydrochloride | HRMS(M + H) 501.1948 |

EXAMPLE 131

3-(4-Hydroxybenzofur-7-yl)-4-[1-(3-hydroxypropyl)-1H-indol-3-yl]pyrrole-2,5-dione Dissolve 3-(4-methoxybenzofur-7-yl)-4-[1-(3-hydroxypropyl)-1H-indol-3-yl]pyrrole-2,5-dione (0.1 g, 0.24 mmol) in 2.5 mL dichloromethane under nitrogen at −78° C. Add boron tribromide (0.11 mL, 1.16 mmol, 5 equiv) dropwise and stir at −78° C. for 1 hr, warm to room temperature and stir for 1 hr. Quench the reaction with ice and then extract with ethyl acetate. Washed the organics with brine, dry over sodium sulfate, filter, and concentrate in vacuo. Purification by column chromatography (25% ethyl acetate: hexanes to 50% ethyl acetate: hexanes) afforded 0.050 g (52%) of the title product. High Res. Mass Spec (m/z): Calcd 403.1301 Found 403.1294.

The following compounds may be prepared in a similar manner as in EXAMPLE 131:

| EXAMPLE # | Product | Physical Data |
|---|---|---|
| 132 | 3-(5-Hydroxybenzofur-7-yl)-4-(1-methyl-1H-indol-3-yl)pyrrole-2,5-dione | ES(M⁺ + H) 359.1 |
| 133 | 3-(4-Hydroxybenzofur-7-yl)-4-(1H-indol-3-yl)pyrrole-2,5-dione | ES(M⁺ + H) 345.0 |
| 134 | 3-(4-Hydroxybenzofur-7-yl)-4-[1-(4-hydroxybutyl)1H-indol-3-yl]pyrrole-2,5-dione | ES(M⁺ + H) 417.0 |
| 135 | 3-(4-Hydroxybenzofur-7-yl)-4-(1-methyl-1H-indol-3-yl)pyrrole-2,5-dione | ES(M⁺ + H) 359.1 |

EXAMPLE 136

3-(5-Hydroxybenzofur-7-yl)-4-[1-(piperidin-4-yl)-1H-indol-3-yl]pyrrole-2,5-dione Combine 3-(5-methoxybenzofur-7-yl)-4-[1-(piperidin-4-yl)-1H-indol-3-yl]pyrrole-2,5-dione (0.125 g, 0.24 mmol) and pyridine hydrochloride (2.2 g, 18-fold excess by weight) under nitrogen. Attach a heating mantle and heat to 190° C. for 45 min. Let cool to 20° C., then extract with ethyl acetate versus water. Wash with brine, dry organic layer over magnesium sulfate, filter and concentrate. Purification by column chromatography (5% methanol: dichloromethane) gives 0.085 g (70%) product. High Res. Mass Spec (m/z): Calcd 518.2080 found 518.2080.

EXAMPLE 137

3-[5-(Piperidin-4-yloxy)benzofur-7-yl]4-(1-methyl-1H-indol-3-yl)pyrrole-2,5-one

Dissolve 3-[5-(1-benzylpiperidin-4-yloxy)benzofur-7-yl]-4-(1-methyl-1H-indol-3-yl)pyrrole-2,5-dione (0.050 g, 0.094 mmol) in 1,2-dichloroethane (10 mL) under nitrogen and add 1-chloroethyl chloroformate (61 μL). Heat to reflux for 4 hours, then add methanol (20 mL) and heat for an additional 1.5 hours. Cool to 20° C., then concentrate and redissolve in 1 mL N,N-dimethylformamide. Purification by reverse phase affords 0.018 g of the title product as the hydrochloride salt. High Res. Mass Spec (m/z): Calcd 442.1767 Found 442.1762.

The following compounds may be prepared in a similar manner as EXAMPLE 137:

EXAMPLE 146

3-(Benzofur-7-yl)-4-[N-(endo-8-azabicyclo[3.2.1]octan-3-yl)-1H-indol-3-yl]pyrrole-2,5-dione hydrochloride Add 3-(benzofur-7-yl)-4-[N-(endo-8-carbethoxy-8-azabicyclo[3.2.1]octan-3-yl)-1H-indol-3-yl]pyrrole-2,5-dione (220 mg, 0.43 mmol) with pyridine HCl (1 g, 8.65 mmol) and heat to 160° C. in an argon atmosphere for 2 h. Cool the reaction mixture and pour into water (100 ml). After addition of sodium hydroxide (1 g, 25 mmol), extract the aqueous solution with dichloromethane. Evaporate the organic layer and stir the remaining solid with 10% HCl in dioxane (3 mL). Filter the resulting solid and dry in vacuo to afford 160 mg of the title compound as red crystals. ES(M⁺+H): 438.2.

EXAMPLE 147

3-(4-Hydroxybenzofur-7-yl)-4-(2-chloro-1-methyl-1H-indol-3-yl)pyrrole-2,5-dione

Dissolve 3-(4-hydroxybenzofur-7-yl)-4-(1-methyl-1H-indol-3-yl)pyrrole-2,5-dione (0.25 g, 0.70 mmol) in 50 mL chloroform under nitrogen. Add 0.093 g (0.70 mmol, 1 equiv) N-chloro succinimide and attach a reflux condenser. Heat to 50° C. and let go overnight. Let cool to room temperature, then extract with ethyl acetate versus water. Wash with brine, then dry over sodium sulfate. Filter and concentrate in vacuo. Purification by column chromatography (20% ethyl acetate: hexanes) yields 0.034 g (12%) product. High Res. Mass Spec (m/z): Calcd 393.0655 Found 393.0642.

EXAMPLE 148

3-(Benzofur-7-yl)-4-[1-(4-oxocyclohexyl)-1H-indol-3-yl]pyrrole-2,5-dione

Dissolve 3-(Benzofur-7-yl)-4-[1-(1,4-dioxa-spiro[4.5]dec-8-yl)-4-fluoro-1H-indol-3-yl]pyrrole-2,5-dione (1.40 g, 2.88 mmol) in tetrahydrofuran (20 mL) and stir at room temperature. Add 1N hydrochloric acid (20 mL) and heat the reaction to reflux for 24 h. Upon completion, Filter the product, rinse with cold water, and dry under vaccuum. The orange solid is used without further purification, 1.1 g (87%). MS (ES, m/z): 443.18(M⁺+1), 441.13(M⁺−1).

| EXAMPLE # | Product | Physical Data |
|---|---|---|
| 138 | 3-(Imidazo[1,2-a]pyridin-3-yl)-4-[1-(3,3-dimethylpiperidin-4-yl)-1H-indol-3-yl]pyrrole-2,5-dione hydrochloride | HRMS(M + 1): 442.1762 |
| 139 | 3-(Benzofur-7-yl)-4-[1-(piperidin-4-yl)-1H-indol-3-yl]pyrrole-2,5-dione | ES(M⁺ + H) 412.2 |
| 140 | (R)-3-[5-(Pyrrolidin-3-yloxy)benzofur-7-yl]-4-(1-methyl-1H-indol-3-yl)pyrrole-2,5-dione hydrochloride | ESMS(M⁺ + H) m/z 428.1 |
| 141 | 3-(5-Fluorobenzofur-7-yl)-4-[1-(piperidin-3-yl)-1H-indol-3-yl]pyrrole-2,5-dione hydrochloride | HRMS(M + 1): 430.1567 |
| 142 | 3-(6-Fluorobenzofur-7-yl)-4-[1-(piperidin-3-yl)-1H-indol-3-yl]pyrrole-2,5-dione hydrochloride | HRMS(M + 1): 430.1567 |
| 143 | 3-(6-Fluorobenzofur-7-yl)-4-[7-methyl-1-(piperidin-4-yl)-1H-indol-3-yl]pyrrole-2,5-dione hydrochloride | ES(M⁺ + H) 444.1 |
| 144 | 3-(4-Methoxybenzofur-7-yl)-4-[1-(piperidin-4-yl)-1H-indol-3-yl]pyrrole-2,5-dione | HRMS(m/z): 442.1767 |
| 145 | 3-(5-Hydroxybenzofur-7-yl)-4-[1-(3-hyroxypropyl)-1H-indol-3-yl]pyrrole-2,5-dione | ES(M⁺ + H) 403.19 |

The following compound may be prepared as described in EXAMPLE 148:

| EXAMPLE # | Product Name | Physical Data |
|---|---|---|
| 149 | 3-(6-Fluorobenzofur-7-yl)-4-[1-(4-oxocyclohexyl)-1H-indol-3-yl]pyrrole-2,5-dione | ES(M$^+$ + H): 443.2 |

EXAMPLE 150

3-(Benzofur-7-yl)-4-[4-fluoro-1-(4-trans-isobutylaminocyclohexyl)-1H-indol-3-yl]pyrrole-2,5-dione hydrochloride Add to a suspension of 3-(benzofur-7-yl)-4-[4-fluoro-1-(4-oxocyclohexyl)-1H-indol-3-yl]pyrrole-2,5-dione (1.26 mmol, 0.678 g) in anhydrous tetrahydrofuran (3 mL), isobutylamine (12.6 mmol) and a drop of glacial acetic acid, stir at room temperature under nitrogen for several hours. Add sodium triacetoxyborohydride (2.52 mmol, 0.534 g) in two portions, and stir at room temperature overnight. Upon completion by TLC (use 1:1 ethyl acetate/hexanes with 10% triethyl amine), dilute the reaction with ethyl acetate (300 mL) and wash with saturated sodium bicarbonate solution (100 mL). Separate the two phases, wash the organic layer with water (50 mL), brine (50 mL), dry over anhydrous sodium sulfate, and concentrate. Purify the residue by flash column chromatography (ethyl acetate/hexanes with 10% triethyl amine) to isolate the free amine product. Dissolve the amine (0.556 mmol) in methanol (3 mL) and concentrate hydrochloric acid is added (0.030 g, 0.600 mmol), heat the reaction to 45° C. under nitrogen for 30 min. Cool to room temperature, then in an ice bath. Filter the hydrochloride crystals and dry to yield the title compound.

MS(ES,m/z):C30H30FN3O3.ClH: 500.38 (M$^+$+1), 498.11 (M$^+$−1).

The following compounds are prepared as EXAMPLE 150:

EXAMPLE 156

Cis and Trans 3-(6-Fluorobenzofur-7-yl)-4-[1-(4-hydroxycyclohexyl)-1H-indol-3-yl]pyrrole-2,5-dione Cool a solution of 3-(6-fluorobenzofur-7-yl)-4-[1-(4-oxocyclohexyl)-1H-indol-3-yl]pyrrole-2,5-dione (395 mg, 0.89 mmol) in tetrahydrofuran (20 ml) in an ice bath. Add sodium borohydride (10 mg, 0.27 mmol) in one portion and stir for 5 minutes. Add another portion of sodium borohydride (10 mg, 0.27 mmol) and stir for 10 minutes in the ice bath. Quench the reaction is with water, then dilute with ethyl acetate, wash with water, 1N HCl, brine, dry over magnesium sulfate, filter, concentrate to a red foam. Purification by flash chromatography separates cis and trans isomers to give cis 3-(6-fluorobenzofur-7-yl)-4-[1-(4-hydroxycyclohexyl)-1H-indol-3-yl]pyrrole-2,5-dione and trans 3-(6-fluorobenzofur-7-yl)-4-[1-(4-hydroxycyclohexyl)-1H-indol-3-yl]pyrrole-2,5-dione as red solids. ES(M$^+$+H): 445.1.

EXAMPLE 157

3-[5-(2-Diethylaminoethoxy)benzofur-7-yl]-4-(1-methyl-1H-indol-3-yl)pyrrole-2,5-dione hydrochloride Add to a stirred solution of 3-[5-(2-diethylaminoethoxy)benzofur-7-yl]4-(1-methyl-1H-indol-3-yl)furo-2,5-dione (490 mg, 1.07 mmol) in N,N-dimethylformamide (20 ml), methanol (0.2 ml) and 1,1,1,3,3,3-hexamethyl-disilazane (2.25 ml, 10.7 mmol). Heat the reaction to 60° C. overnight. Reaction is continued over the following two nights, along with further additions of 1,1,1,3,3,3-hexamethyl-disilazane (3×1 ml), until reaction is complete. Diluted with ethyl acetate, wash with water, brine, dry over sodium sulfate, filter and concentrate to a red oil. Reversed phase chromatography (acetonitrile: 0.1% hydrochloric acid/H$_2$O) affords the product as an orange solid. Trituration from 5% methanol:dichloromethane with diethyl ether, then filtration, gives the title compound (230 mg, 43%) as an orange solid. HRMS: calculated 458.2080 found 458.2069.

Using the method described above, the following compounds are made in a substantially similar manner:

| EXAMPLE # | Product Name | Physical Data |
|---|---|---|
| 151 | 3-(Benzofur-7-yl)-4-[4-fluoro-1-(4-cis-isobutylaminocyclohexyl)-1H-indol-3-yl]pyrrole-2,5-dione hydrochloride | MS(ES, m/z) (M$^+$ + H) 500.42 |
| 152 | 3-(Benzofur-7-yl)-4-[1-(4-cis-pyrrolidin-1-ylcyclohexyl)-1H-indol-3-yl]pyrrole-2,5-dione hydrochloride | MS(ES, m/z) 480.41 (M$^+$ + 1), 478.51 (M+ − 1). |
| 153 | 3-(Benzofur-7-yl)-4-[1-(4-trans-pyrrolidin-1-ylcyclohexyl)-1H-indol-3-yl]pyrrole-2,5-dione hydrochloride | MS(ES, m/z) 480.42 (M$^+$ + 1), 478.53 (M$^+$ − 1). |
| 154 | 3-(6-Fluorobenzofur-7-yl)-4-[1-(1-isopropylpiperidin-4-yl)-1H-indol-3-yl]pyrrole-2,5-dione | ES(M$^+$ + H): 472.2 |
| 155 | 3-(Benzofur-7-yl)-4-[1-(4-trans-sec-butylaminocyclohexyl)-4-fluoro-1H-indol-3-yl]pyrrole-2,5-dione hydrochloride | MS(ES, m/z) 500.31 (M$^+$ + 1), 498.46 (M$^+$ − 1). |

| EXAMPLE # | Product | Physical Data |
|---|---|---|
| 158 | 3-[4-(2-Diethylaminoethoxy)benzofur-7-yl]-4-(1-iso-propyl-1H-indol-3-yl)pyrrole-2,5-dione hydrochloride | HRMS(M + 1): 486.2408 |
| 159 | 3-[4-(2-Diethylaminopropoxy)benzofur-7-yl]-4-(1-iso-propyl-1H-indol-3-yl)pyrrole-2,5-dione hydrochloride | HRMS(M + 1): 500.2552 |
| 160 | 3-(5-Aminobenzofur-7-yl)-4-(1-methyl-1H-indol-3-yl)pyrrole-2,5-dione | HRMS(M + 1): 358.1196. |
| 161 | 3-[4-(N-acetamide)benzofur-7-yl]-4-(1-methyl-1H-indol-3-yl)pyrrole-2,5-dione | ES(M+ + 1) 400.1 |

EXAMPLE 162

3-Imidazo[1,2-a]pyridin-3-yl)-4-{1-[1-(N,N-dimethylacetamide)piperidin-4-yl]indol-3-yl}pyrrole-2,5-dione Dissolve 3-imidazo[1,2-a]pyridin-3-yl-4-[1-(piperidin-4-yl)-1H-indol-3-yl]pyrrole-2,5-dione hydrochloride (200 mg, 0.45 mmol) in methanol (2 ml). Add triethylamine (0.19 ml, 1.34 mmol), followed by N,N-dimethyl carbamyl chloride (0.06 ml, 0.67 mmol) and stir under nitrogen atmosphere for one hour. Concentrate to a red oil. Purification by flash chromatography (ethyl acetate) yields 180 mg (83%) of the title compound as an orange solid. ES($M^{+1}$): 483.2

The following compounds may be prepared essentially as described above:

| EXAMPLE # | Product Name | Physical Data |
|---|---|---|
| 163 | 3-(Imidazo[1,2-a]pyridin-3-yl)-4-{5-chloro-1-[3,3-dimethyl-1-(N,N-dimethylacetamide)piperidin-4-yl]indol-3-yl}pyrrole-2,5-dione | ES(M ++ H): 545.1 |
| 164 | 3-(6-Fluoro-2,3-dihydrobenzofur-7-yl)-4-{1-[1-(2-dimethylamino-1-oxoethyl)piperidin-4-yl]-1H-indol-3-yl}pyrrole-2,5-dione | MS 517(M + H) |
| 165 | 3-(6-Fluoro-2,3-dihydrobenzofur-7-yl)-4-{1-[1-(N,N-dimethylacetamide)piperidin-4-yl]-1H-indol-3-yl}pyrrole-2,5-dione | MS(M + H) 503 |

EXAMPLE 166

3-(Imidazo[1,2-a]pyridin-3-yl)-4-[1-(1-propionylpiperidin-4-yl)-1H-indol-3-yl]pyrrole-2,5-dione Dissolve 3-(imidazo[1,2-a]pyridin-3-yl)-4-[1-(piperidin-4-yl)-1H-indol-3-yl]-pyrrole-2,5-dione hydrochloride (90 mg, 0.22 mmol) and 1.0 M hydrochloric acid in 10 mL 8:2 methanol:distilled water. Add propionic anhydride (0.1 mL, 0.078 mmol) immediately followed by triethylamine (0.3 mL, 2.1 mmol). Stir the reaction at 20° C. for 30 minutes, filter the solid, rinse with cold methanol and dry at 70° C. under reduced pressure vacuum to provide the title compound. ES(M++H): 468.2.

EXAMPLE 167

3-(6-Fluoro-2,3-dihydrobenzofur-7-yl)-4-{1-[1-(1-carboxylic acid 2-methoxyethyl ester)piperidin-4-yl]-1H-indol-3-yl-}-pyrrole-2,5-dione Add triethyl amine (0.1 mL, 0.7 mmol) and chloroformic acid 2-methoxyethyl ester (50 μM, 0.46 mmol) to a solution of 3-(6-fluoro-2,3-dihydrobenzofur-7-yl)-4-[1-(piperidin-4-yl)-1H-indol-3-yl]-pyrrole-2,5-dione (100 mg, 0.23 mmol) in methanol (3 mL). Stir the reaction mixture at ambient temperature for 2 hours. Dilute with ethyl acetate and wash the organic layer with water, dry (MgSO$_4$), concentrate, and chromatograph (silica gel; hexane/EtOAc, 1:1 to 0:1). An orange solid is isolated (55 mg, 45%). MS (ESI) m/z 534 (M+H)$^+$.

The following compounds may be prepared essentially as described above:

| EXAMPLE # | Product Name | Physical Data |
|---|---|---|
| 168 | 3-(Imidazo[1,2-a]pyridin-3-yl)-4-{1-[1-(1-carboxylic acid 2-propyl)piperidin-4-yl]-1H-indol-3-yl}pyrrole-2,5-dione | MS(M + H) 498 |
| 169 | 3-(Imidazo[1,2-a]pyridin-3-yl)-4-{1-[1-(1-carboxylic acid 2-isopropyl)piperidin-4-yl]-1H-indol-3-yl}pyrrole-2,5-dione | MS(M + H) 498 |

EXAMPLE 170

3-(6-Fluoro-2,3-dihydrobenzofur-7-yl)-4-{1-[1-(pyrazine-2-carbonyl)piperidin-4-yl]-1H-indol-3-yl}pyrrole-2,5-dione Mix 3-(6-Fluoro-2,3-dihydrobenzofur-7-yl)-4-[1-(piperidin-4-yl]-1H-indol-3-yl)pyrrole-2,5-dione (180 mg, 0.42 mmol) in dimethylformamide with triethyl amine (0.2 mL, 1.4 mmol), 2-pyrazinecarboxylic acid (57 mg, 0.46 mmol), N-(3-dimethylaminopropyl)-N'-ethylcarbodiimid hydrochloride (106 mg, 0.55 mmol), and 1-hydroxybenzotriazole (74 mg, 0.55 mmol). Stir the reaction mixture at ambient temperature for 18 hours. Dilute with ethyl acetate, and wash the organic layer with water/brine (×4). Dry over magnesium sulfate and concentrate. Purify by chromatography (silica gel; hexane/EtOAc; 1:1 to 0:1) to give an orange solid (105 mg, 49%). MS (MSI) m/z 538 (M+H)$^+$.

The following compounds are prepared essentially as described above:

The catalysis of the reaction:
KRREILSRRP(pS)YR+AT$^{33}$P→KRREIL($^{33}$pS)RRP(pS)YR [measured]+ADP by GSK-3β is measured in a reaction mixture comprised of the following: 50 mM MOPS (4-morpholinepropanesulfonic acid) pH 7.0; 50 μM phosphoCREB peptide; 50 μM ATP; 0.5 μCi ATP[γ-$^{33}$P]; 12.5 mM MgCl$_2$; 0.03% Triton-X; 4% DMSO; and 1 nM recombinant human GSK-3β. The reaction is initiated by the addition of enzyme. The final reaction volume is 100 μL. The reaction is allowed to proceed for 60 minutes at room temperature and is stopped by the addition of 75 μL of 10% phosphoric acid. To capture KRREIL($^{33}$pS)RRP(pS)YR formed in the reaction and to remove unreacted AT$^{33}$P, 160 μL of the stopped reaction mixture is transferred to a pre-wetted (0.75% phosphoric acid) phosphocellulose microfiltration plate [Millipore Cat.# MAPH NOB 50] and after 90 minutes incubation on the plate, the stopped reaction mixture is passed through the filter using a Titertek Map Extractor. The filter containing the trapped KRREIL($^{33}$pS)RRP(pS)YR is washed with 220 μL of 0.75% phosphoric acid. Filter plates are blotted to remove droplets

| EXAMPLE # | Product Name | Physical Data |
|---|---|---|
| 171 | 3-(6-Fluoro-2,3-dihydrobenzofur-7-yl)-4-{1-[1-(pyridine-2-carbonyl)piperidin-4-yl]-1H-indol-3-yl}pyrrole-2,5-dione | MS(M + H) 537 |
| 172 | 3-(6-Fluoro-2,3-dihydrobenzofur-7-yl)-4-{1-[1-(pyridine-3-carbonyl)piperidin-4-yl]-1H-indol-3-yl}pyrrole-2,5-dione | MS(M + H) 537 |
| 173 | 3-(6-Fluoro-2,3-dihydrobenzofur-7-yl)-4-{1-[1-(pyrimidine-5-carbonyl)piperidin-4-yl]-1H-indol-3-yl}pyrrole-2,5-dione | MS(M + H) 538 |
| 174 | 3-(6-Fluoro-2,3-dihydrobenzofur-7-yl)-4-{1-[1-(pyridine-4-carbonyl)piperidin-4-yl]-1H-indol-3-yl}pyrrole-2,5-dione | MS(M + H) 537 |

EXAMPLE 175

3-(6-Fluoro-2,3-dihydrobenzofur-7-yl)-4-[1-(1-methylpiperidin-4-yl)-1H-indol-3-yl]pyrrole-2,5-dione Beginning with 3-(6-fluoro-2,3-dihydrobenzofur-7-yl)-4-{1-[1-(Boc)piperidin-4-yl]-1H-indol-3-yl}pyrrole-2,5-dione, the title compound is prepared essentially as described in Preparation 134. MS(M+H)=446.

EXAMPLE 176

3-(Imidazo[1,2-a]pyridin-3-yl)-4-[1-(1-isopropylpiperidin-4-yl)-1H-indol-3-yl]pyrrole-2,5-dione Beginning with 3-(imidazo[1,2-a]pyridin-3-yl)-4-{1-[1-(Boc)piperidin-4-yl]-1H-indol-3-yl}pyrrole-2,5-dione, the title compound is prepared essentially as described in Preparation 134. MS(M+H)=454.

Kinase Inhibition Assay

An important in vitro test is the ability of the compound to inhibit the activity of the GSK-3β enzyme. This test is done according to a standard protocol. (See Fiol, et al, A Secondary Phosphorylation of CREB$^{341}$ at Ser$^{129}$ Is Required for the cAMP-Mediated Control of Gene Expression: A Role for Glycogen Synthase Kinase-3 in the Control of Gene Expression, J. Biol. Chem., 269, 32187-32193 (1994)).

from the underdrain. The underdrain is removed from the filter and the filter is placed into a clear plate liner (Wallac, Inc.). Added to each well is 100 μL of Microscint 20 (Packard).

After standing at least six hours (preferably overnight), the plates are counted in a Trilux scintillation counter (Wallac, Inc.). The ability of a compound to inhibit GSK-3β is determined by including various concentrations of the compound in the reaction mixture and comparing the signal produced to the signal produced in a reaction mixture without the compound.

The test yields the molar concentration of the test compound that produces a 50% inhibition of the GSK-3β enzyme activity. The lower the value in this test, the more active the test compound is. The exemplified compounds exhibit IC50≦1 μM.

In the present invention, inhibitors that demonstrate 50% effective concentrations (IC$_{50}$) of about 200 nM or less are preferred. Furthermore, also preferred are those which show 50% effective concentrations of 50 nM or less, more preferably those which show 50% effective concentrations of 20 nM or less, and most preferably those which show 50% effective concentrations of 10 nM or less in the protocol described by FIOL, Carol J., et al., J. Biol. Chem., 269, 32187-32193 (1994). It is also preferred, in the practice of the present invention, that the GSK-3 inhibitor achieve plasma exposures >1000 ng*hr/mL. Additionally, those GSK-3 inhibitors exhibiting a low IC$_{50}$ value, such as below 10 nm, and plasma exposures <1000 ng*hr/mL represent a further preferred embodiment of the present invention.

Representative examples are shown in Table II.

TABLE II

| Ex. # | GSK-3β IC50 (μM) |
|---|---|
| 1 | 0.1757 |
| 100 | 0.14341 |
| 102 | 0.1253 |
| 114 | 0.1327 |
| 118 | 0.07019 |
| 119 | 0.0095 |
| 135 | 0.0552 |
| 139 | 0.00574 |
| 150 | 0.0106 |

Glycogen Synthesis Assay

This test measures the increase in the production of glycogen both in the absence and in the presence of insulin in the cells. This test is done according to standard protocols. (See Berger and Hayes, A High-Capacity assay for Activators of Glucose Incorporation into Glycogen in L6 Muscle Cells, *Analytical Biochemistry*, 261, 159-163 (1998).)

Briefly, 3T3-L1 adipocytes are plated and differentiated in a 96-well plate at 25,000 cells/well. The plate is serum-starved overnight. The serum-starvation media is removed just prior to assay, and the plate is washed with 100 μl/well Krebs-Ringer-Hepes buffer (KRBH). The KRBH is removed and 50 μl of compound (twice the amount of the final concentration) is added to the assay plate. Next, 50 μl of $^{14}$C-labeled glucose is added to the assay plate at 0.1 μCi/well. The plate is then incubated at 37° C. for 2 hours.

The plate is washed with 100 μL/well of PBS, and the cells are lysed with 75 μl/well of 1N NaOH. The plate is heated at 70° C. for 20 minutes. An aliquot (50 μl) of the supernatant is transferred from the assay plate to a Millipore FC filter plate containing 120 μl/well of ice-cold ethanol. The plate is allowed to stand for 2 hours at 4° C. to facilitate precipitation. The ethanol is removed from the filter plate via a vacuum manifold, and the plate is washed with 100 μL/well of ice-cold 70% ethanol. The plate was allowed to dry overnight, and 75 μl/well of Microscint-20 was added to the filter plate. The plate was then counted on a Packard Topcount.

Glucose Lowering Assay

This test measures the effect of the test compound on blood glucose and triglycerides relative to insulin. (See Eldar-Finkleman, et al, Expression and Characterization of Glycogen Synthase Kinase-3 Mutants and Their Effect on Glycogen Synthase Activity in Intact Cells, *Proc. Nat. Acad. Sci.*, 93, 10228-10233 (1996).)

ZDF rats (Charles River, Inc.) at six weeks of age are housed individually with free access to food and water. Rats are dosed with drug once daily by oral gavage, with the compound prepared as a suspension in 1% caboxymethylcellulosolve/0.25% Tween 80 (CMC-Tween). Vehicle controls are dosed with CMC-Tween only. The duration of study varied according to the protocol used, with acute dosing studies lasting one day and dose escalation studies lasting seven days. Body weights and food consumption measurements are also performed once a week for seven-day studies. For measurement of blood glucose and triglycerides, blood samples of 600 μl are collected by the tail snip method. (The tail snip for blood sampling is as follows: 1-2 mm of the tail is snipped with a sharp blade. After collection of blood, a scab forms at the site of wound. This scab is removed and the tail is gently massaged for other subsequent bleedings.) Glucose and triglyceride determinations are performed on a Hitachi 912 metabolic analyzer, with a kit utilizing the Trinder method. On termination of study, specific tissues (e.g., heart, pancreas, adipose tissues, and liver) are excised to evaluate the effect of these drugs on their metabolic functions.

Ex Vivo Brain Assay

This assay assesses the GSK-3β kinase activity of the test compound in brain cortex tissue. It is performed according to standard protocols (Wang, et al., *Anal. Biochem.*, 220, 397402 (1994)).

The ex vivo GSK-3β kinase activity of a compound is assayed following oral dosing of 2 to 3 month old PDAPP or CD-1 mice. After a 20 mg/kg, 24 hour dose, followed by an additional three-hour dose, brain cortex tissue is dissected and homogenized in freshly prepared lysis buffer (10 mM $K_2HPO_4$ pH 7.2, 1 mM EDTA, 5 mM EGTA, 10 mM $MgCl_2$, 50 mM β-Glycerophosphate, 1 mM $Na_3VO_4$, 2 mM DTT, 1 μM Microcystin, COMPLETE protease inhibitor tablet, no detergent). Following a thirty-minute incubation on ice, cortex homogenate samples are centrifuged (100,000 G) for 30 minutes at 4° C. The total protein concentration of homogenate is determined using the BCA method (Pierce). GSK-3β activity in cytosolic homogenate from vehicle- and compound-treated mice is then assayed. The kinase reaction occurs in a 50 μl total volume containing 20 mM MOPS pH 7.4, 25 mM β-glycerol phosphate, 5 mM EGTA, 1 mM $NA_3VO_4$, 1 mM DTT, 15 mM $MgCl_2$, 100 μM cold ATP, 200 μM CREB peptide, 10 μL cytosolic cortex brain homogenate, and 5 μCi γ-$^{33}$P-ATP. The reactions are incubated for thirty minutes at 30° C. using a Costar round-96 polypropylene plate. Reactions are then stopped with, the addition of 10% $H_3PO_4$ and transferred to a Millipore MAPH-NOB 96-well phosphocellulose plate. Next, the reaction is incubated at room temperature for 1.5 hours, filtered and washed with 320 μl 0.75% $H_3PO_4$, and filtered and washed with 160 μl $H_3PO_4$ at the same concentration using a vacuum manifold. The filter plate is then placed in a carrier plate, and 100 μl of Microscint 20 is added to each well. The plate is sealed with sealing tape and incubated overnight at room temperature. The following day, the filter plate is read for $^{33}$P on Top Count (Packard). Finally, CPM is normalized to CPM per μg of total protein.

β-Catenin Protection Assay

This test measures the fold induction over basal β-catenin and is performed according to standard protocols (Hedgepeth, C. M., *Dev. Biol.* 185, 82-91 (1997); Chen, G., et al., *J. Neurochem.*, 72, 1327-1330 (1999); Hong, M., et al., *J. Biol. Chem.*, 272, 25326-25332 (1997)).

The human familial Alzheimer's disease (FAD) presenilin-1 AG04160C lymphoblast cell line (Coriell Cell Repository, Camden, N.J.) is maintained as a suspension culture in RPMI 1640 (with L-Glutamine) supplemented with 10% fetal bovine serum and 1% penicillin-streptomycin in an atmosphere of 37° C. and 5% $CO_2$. The AG04160C FAD lymphoblast cells are seeded in T-25 $cm^2$ flasks at 2.5 to $5.0×10^5$ cells/ml in a total volume of 10 ml. Following 16-18 hours of growth, cells are treated with compound at concentrations of 0.1 μM, 1.0 μM, and 10 μM, and are incubated for an additional 24 hours. At the completion of the 24-hour incubation, cells are harvested, washed with PBS, and lysed in freshly prepared lysis buffer (10 mM $K_2HPO_4$ pH 7.2, 1 mM EDTA, 5 mM EGTA, 10 mM $MgCl_2$, 50 mM β-Glycerophosphate, 1 mM $Na_3VO_4$, 2 mM DTT, 1 μM Microcystin, 1 mM PMSF, 10 µg/ml leupeptin, 1 µg/ml pepstatin, 1 µg/ml aprotinin, 1% Triton X-100). After a thirty-minute incubation on ice, cells are centrifuged (14,000 rpm) for 30 minutes at 4° C., and resulting supernatants are used as whole cell lysates. The total protein concentration in whole cell lysate samples is determined using the BCA method (Pierce). Next, 15 µg of sample is loaded on a 10% Bis-Tris NuPage gel and transferred to a pure nitrocellulose membrane followed by β-catenin immunoblot analysis using a β-catenin specific antibody (Transduction Labs). The β-catenin accumulation/stability is then quantified following densitometry analysis of protein bands. Final results are reported as fold induction over basal β-catenin.

Representative examples are shown in Table III.

TABLE III

| Ex. # | GSK-3β IC50 (µM)) | Glycogen Synthesis (fold increase at 1 µM) | Glucose Lowering (percent increase vs. effect of insulin) | β-Catenin (fold increase) |
|---|---|---|---|---|
| 119 | 0.0095 | 2.82× in absence of insulin | | 4.9× |
| | | 2.13× in presence of insulin | | |
| 150 | 0.0106 | 2.97× in absence of insulin | 58% | |
| | | 3.92× in presence of insulin | | |

Ovariectomized Rat Assay

Six-month-old virgin Sprague-Dawley rats are maintained on a 12-hour light, 12-hour dark cycle at 22° C. with ad libitum access to food (TD89222 with 0.5% calcium and 0.4% phosphate, Teklad, Madison, Wis.) and water. Bilateral or sham ovariectomies are performed on the rats and they are allowed to lose bone for 1 month. When the rats are 7 months old, sham and ovariectomized (Ovx) controls (7 animals per group) are orally administered vehicle (1% carboxymethyl cellulose/0.25% Tween 80) and a second group of 7 Ovx animals is orally administered the test compound in vehicle. Dosing is done once a day for 2 months. At the end of 2 months, rats are euthanized using $CO_2$ anesthesia and left femur and vertebra are removed, cleaned of soft tissue and stored in 50% ethanol/saline. Bones are analyzed by QCT as described previously (Sato M., Comparative x-ray densitometry of bones from ovariectomized rats. *Bone* 17:157S:162S (1995); Sato M., Kim J., Short L. L., Slemenda C. W, Bryant H. U., Longitudinal and cross-sectional analysis of raloxifene effects on tibiae from ovariectomized aged rats. *J Pharmacol Exp Ther* 272:1252-1259 (1995)).

Compounds of Formula I may be administered by the oral, transdermal, percutaneous, intravenous, intramuscular, intranasal or intrarectal route, in particular circumstances. The route of administration may be varied in any way, limited by the physical properties of the drugs, the convenience of the patient and the caregiver, and other relevant circumstances (See *Remington's Pharmaceutical Sciences*, 18th Ed., Mack Publishing Co. (1990).)

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solutions, suspensions, or the like.

The compounds of the present invention may be administered orally, for example, with an inert diluent or capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention may be determined by a person skilled in the art.

The tablets, pills, capsules, troches, and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials that modify the physical form of the dosage unit, for example, as coatings. Thus, tablets or pills may be coated with sugar, shellac, or other coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations typically contain at least 0.1% of a compound of the invention, but may be varied to be between 0.1 and about 90% of the weight thereof. The amount of the compound of Formula I present in such compositions is such that a suitable dosage will be obtained. The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Preferred compositions and preparations are able to be determined by one skilled in the art.

The compounds of the present invention may also be administered topically, and when done so the carrier may suitably comprise a solution, ointment, or gel base. The base, for example, may comprise one or more of the following: petrolatum, lanolin, polyethylene glycols, bees wax, mineral oil, diluents such as water and alcohol, and emulsifiers, and stabilizers. Topical formulations may contain a concentration of the Formula I, or its pharmaceutical salt, from about 0.1 to about 10% w/v (weight per unit volume).

The compounds of Formula I are generally effective over a wide dosage range. For example, dosages per day normally fall within the range of about 0.0001 to about 30 mg/kg of body weight. In some instances dosage levels below the lower limit of the aforesaid range may be more than adequate, while in other cases still larger doses may be employed without causing any harmful side effect, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

We claim:

1. A compound of Formula I

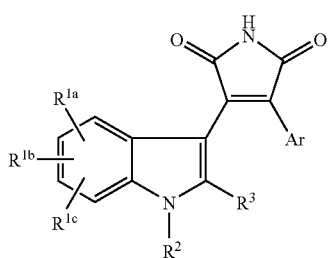

I where:
Ar is benzofur-7-yl optionally substituted in the phenyl ring with $R^8$ and $R^9$, or 2,3-dihydrobenzofur-7-yl optionally substituted in the phenyl ring with $R^8$ and $R^9$ and in the dihydrofuryl ring with $C_1$-$C_4$ alkyl;
G is independently at each occurrence hydroxy, $NR^{11}R^{12}$, or piperidin-4-yl;
$R^2$ is hydrogen, $C_1$-$C_4$ alkyl, —$(CH_2)_m$-G, tetrahydropyran-4-yl, 4-($NR^4R^5$)cyclo-hex-1-yl, 4-hydroxycyclohex-1-yl, 2-azabicyclo[3.2.1]oct-5-yl, the moiety

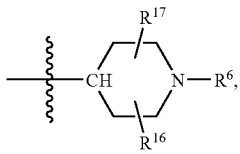

the moiety

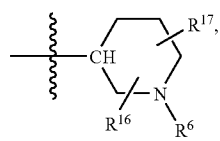

cyclohexan-1-on-4-yl, pyridin-4-yl; and $R^3$ is hydrogen, halo, $C_1$-$C_4$ alkyl, or cyclopropyl;
$R^4$ hydrogen and $R^5$ is hydrogen or $C_1$-$C_4$ alkyl, or $R^4$ and $R^5$ taken together with nitrogen to which they are attached form a pyrrolidine ring;
$R^6$ is hydrogen, benzyl, —$CO_2(C1$-$C_4$ alkyl), —C(O)—$(C_1$-$C_4$ alkyl$)_n$-$NR^{14}R^{15}$, —C(O)tetrahydropyran-4-yl, —C(O)morpholin-4-yl, —$CH_2$-tetrahydropyran-4-yl, an amino acid residue, —C(O)pyridin-2-yl, —C(O)pyridin-3-yl, —C(O)pyridin-4-yl, —C(O)pyrimidin-5-yl, $C_1$-$C_4$ alkyl, —C(O)pyrazin-2-yl, or —$CO_2$—($C_1$-$C_4$ alkyl)-($C_1$-$C_4$ alkoxy);
$R^8$ is —$NHCO_2(C_1$-$C_4$ alkyl), —$NHSO_2(C_1$-$C_4$ alkyl), halo, amino, —O—$(CH_2)_m$-G, —NHC(O)($C_1$-$C_4$ alkyl), $C_1$-$C_4$ alkoxy, hydroxy, —O—$R^{10}$, $C_1$-$C_4$ alkyl, $C_1$-$C_4$ alkylthio, or —$(CH_2)_m$-G;
$R^9$ is halo;
$R^{10}$ is piperidin-3-yl, piperidin-4-yl, or pyrrolidin-3-yl;
$R^{11}$ and $R^{12}$ are independently selected from the group consisting of hydrogen, $C_1$-$C_4$ alkyl, cyclopropylmethyl, benzyl, or, taken together with the nitrogen to which they are attached form a piperidine, 4-hydroxypiperidine, 4-($C_1$-$C_4$ alkyl)piperidine, N—($R^{13}$)-piperazine, or morpholine ring;
$R^{13}$ is hydrogen, C(O)—($C_1$-$C_4$ alkyl), or $C_1$-$C_4$ alkyl;
$R^{14}$ and $R^{15}$ are independently hydrogen or $C_1$-$C_4$ alkyl;
$R^{16}$ is independently at each occurrence hydrogen, geminal dimethyl, geminal diethyl, a spiro-fused $C_3$-$C_6$ cycloalkyl, or $C_1$-$C_4$ alkyl optionally substituted with hydroxy; and $R^{17}$ represents hydrogen, $C_1$-$C_4$ alkyl, or geminal dimethyl, provided that the total number of carbon atoms between $R^{16}$ and $R^{17}$ does not exceed five;
m is independently at each occurrence 2, 3, 4, or 5;
n is independently at each occurrence 0 or 1; or a pharmaceutically acceptable salt thereof, subject to the following provisos:
i) when G is hydroxy, no more than two of $R^{1a}$, $R^2$, or $R^8$ may be —$(CH_2)_m$-G, or —O—$(CH_2)_m$-G; and
ii) when G is $NR^{11}R^{12}$, no more than one of $R^{1a}$, $R^2$, or $R^8$ may be —$(CH_2)_m$-G, or —O—$(CH_2)_m$-G.

2. A compound of claim 1 where Ar is benzofur-7-yl optionally substituted in the phenyl ring with $R^8$ and $R^9$.

3. A compound of claim 1 where Ar is 2,3-dihydrobenzofur-7-yl optionally substituted in the phenyl ring with $R^8$ and $R^9$.

4. A compound of claim 3 where $R^2$ is

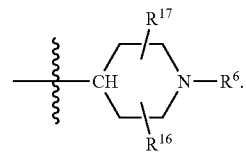

5. A method of treating diabetes in a mammal comprising administering to a mammal in need of such treatment an effective amount of a compound of claim 1.

6. A pharmaceutical formulation comprising a compound of claim 1 in combination with a pharmaceutically acceptable carrier, diluent, or excipient.

7. A compound of claim 3 where $R^2$ is piperidin-4-yl.

8. A compound of claim 7 where $R^8$ is halo and $R^9$ is fluoro.

9. The compound 3-(2,3-dihydro-5,6-difluorobenzofur-7-yl)-4-[1-(piperidin-4-yl)-1H-indol-3-yl]pyrrole-2,5-dione or a pharmaceutically acceptable salt thereof.

* * * * *